United States Patent
Belagali et al.

(10) Patent No.: US 10,076,340 B2
(45) Date of Patent: Sep. 18, 2018

(54) SURGICAL TOOL SYSTEM WITH A TOOL UNIT THAT INCLUDES A POWER GENERATING UNIT AND A BATTERY AND CONTROL MODULE THAT IS RELEASABLY ATTACHED TO THE TOOL UNIT FOR ENERGIZING AND CONTROLLING THE POWER GENERATING UNIT

(71) Applicant: Stryker Corporation, Kalamazoo, MI (US)

(72) Inventors: Krishnamurthy Belagali, Portage, MI (US); William L. Hassler, Jr., Portage, MI (US); David Hershberger, Kalamazoo, MI (US); Michael Irvine, Byron Center, MI (US)

(73) Assignee: Stryker Corporation, Kalamazoo, MI (US)

( * ) Notice: Subject to any disclaimer, the term of this patent is extended or adjusted under 35 U.S.C. 154(b) by 18 days.

(21) Appl. No.: 14/548,713

(22) Filed: Nov. 20, 2014

(65) Prior Publication Data
US 2015/0182230 A1 Jul. 2, 2015

Related U.S. Application Data

(63) Continuation of application No. PCT/US2013/042464, filed on May 23, 2013.
(Continued)

(51) Int. Cl.
*A61B 17/14* (2006.01)
*A61B 17/16* (2006.01)
(Continued)

(52) U.S. Cl.
CPC ............ *A61B 17/14* (2013.01); *A61B 17/142* (2016.11); *A61B 17/1626* (2013.01);
(Continued)

(58) Field of Classification Search
CPC ............... A61B 17/14; A61B 17/1613; A61B 17/1626; A61B 17/1628;
(Continued)

(56) References Cited

U.S. PATENT DOCUMENTS 3,294,183 A    12/1966  Riley, Jr. et al.
3,321,650 A *   5/1967  Pedone, Jr. ............ H02K 7/145
                                                        310/112
(Continued)

FOREIGN PATENT DOCUMENTS

CN         1661878 A     8/2005
CN       101011279 A     8/2007
(Continued)

OTHER PUBLICATIONS

Machine translation of description of Broghammer (EP 1788597).*
(Continued)

*Primary Examiner* — Matthew Lawson
*Assistant Examiner* — Amy Sipp
(74) *Attorney, Agent, or Firm* — Howard & Howard Attorneys PLLC

(57) ABSTRACT

A battery and control module to which a powered surgical tool is releasably attached. Internal to the module there is: a cell for energizing the tool; a sensor for monitoring an operational state of the tool; a sensor for monitoring a trigger external to the module; and a control circuit. Based on the signals output by the sensors, the control circuit selectively applies energization signals from the cell to the power generating unit internal to the surgical tool. In some versions of the invention, the trigger is attached to the module.

24 Claims, 69 Drawing Sheets

Related U.S. Application Data

(60) Provisional application No. 61/650,732, filed on May 23, 2012.

(51) Int. Cl.
 B25F 5/02 (2006.01)
 A61B 90/00 (2016.01)
 A61B 17/00 (2006.01)

(52) U.S. Cl.
 CPC .......... A61B 17/1628 (2013.01); A61B 90/03 (2016.02); B25F 5/02 (2013.01); *A61B 2017/00022* (2013.01); *A61B 2017/00221* (2013.01); *A61B 2017/00734* (2013.01)

(58) Field of Classification Search
 CPC ........... A61B 2017/00022; A61B 2017/00734; A61B 2017/00221; B25F 5/00; B25F 5/02
 USPC ..................................... 173/217; 310/47, 50
 See application file for complete search history.

(56) References Cited

U.S. PATENT DOCUMENTS

| | | | |
|---|---|---|---|
| 3,734,207 A * | 5/1973 | Fishbein | A61B 17/1622 173/217 |
| 4,050,528 A | 9/1977 | Foltz et al. | |
| 4,091,880 A * | 5/1978 | Troutner | A61B 17/1628 173/170 |
| 4,728,876 A * | 3/1988 | Mongeon | A61B 17/1624 310/50 |
| 5,268,622 A * | 12/1993 | Philipp | A61B 17/1626 318/400.08 |
| 5,490,860 A * | 2/1996 | Middle | A61B 17/32002 604/22 |
| 6,013,991 A | 1/2000 | Philipp | |
| 6,018,227 A | 1/2000 | Kumar et al. | |
| 6,059,806 A * | 5/2000 | Hoegerle | A61B 17/1628 606/180 |
| 6,104,162 A | 8/2000 | Sainsbury et al. | |
| 6,338,731 B1 | 1/2002 | Laufer et al. | |
| 6,536,536 B1 * | 3/2003 | Gass | B23B 31/123 173/171 |
| 7,422,582 B2 | 9/2008 | Malackowski et al. | |
| 7,638,958 B2 | 12/2009 | Philipp et al. | |
| 7,721,934 B2 | 5/2010 | Shelton, IV et al. | |
| 7,833,241 B2 | 11/2010 | Gant | |
| 8,029,510 B2 | 10/2011 | Hoegerle | |
| 8,328,802 B2 | 12/2012 | Deville et al. | |
| 2003/0011245 A1 | 1/2003 | Fiebig | |
| 2004/0188119 A1 * | 9/2004 | Chen | B25F 5/02 173/217 |
| 2005/0194935 A1 | 9/2005 | Kubota et al. | |
| 2006/0087286 A1 | 4/2006 | Phillips et al. | |
| 2006/0206100 A1 | 9/2006 | Eskridge et al. | |
| 2007/0090788 A1 | 4/2007 | Hansford et al. | |
| 2007/0244471 A1 | 10/2007 | Malackowski | |
| 2008/0042861 A1 | 2/2008 | Dacquay et al. | |
| 2008/0077149 A1 | 3/2008 | Hoegerle | |
| 2009/0108048 A1 | 4/2009 | Zemlok et al. | |
| 2010/0084150 A1 | 4/2010 | Suzuki et al. | |
| 2014/0266057 A1 | 9/2014 | Woods | |
| 2015/0182230 A1 | 7/2015 | Belagali et al. | |
| 2016/0287265 A1 | 10/2016 | Macdonald et al. | |

FOREIGN PATENT DOCUMENTS

| | | | |
|---|---|---|---|
| EP | 1788597 A1 * | 5/2007 | ................ B25F 5/02 |
| EP | 2392269 A1 | 12/2011 | |
| JP | 2002538880 A | 11/2002 | |
| WO | 2012061649 A1 | 5/2012 | |
| WO | 2015112686 A1 | 7/2015 | |
| WO | 2015143104 A1 | 9/2015 | |

OTHER PUBLICATIONS

PCT "International Search Report and Written Opinion" for PCT/US2013/042464, dated Dec. 16, 2013.
Infineon Technologies AG, "XMC4500—Microcontroller Series for Industrial Applications—XMC4000 Family—ARM Cortex-M4 32-Bit Processor Core Data Sheet", vol. 1.0, Jan. 2013, pp. 1-112.
Wikipedia, "H Bridge", downloaded from https://en.wikipedia.org/wiki/H_bridge on Jun. 30, 2017, 5 pages.
English language abstract for CN 1661878 extracted from espacenet.com database on Nov. 29, 2017, 2 pages.
English language abstract for CN 101011279 extracted from espacenet.com database on Nov. 29, 2017, 2 pages.
English language abstract for JP 2002-538880 extracted from espacenet.com database on Nov. 29, 2017, 2 pages.

\* cited by examiner

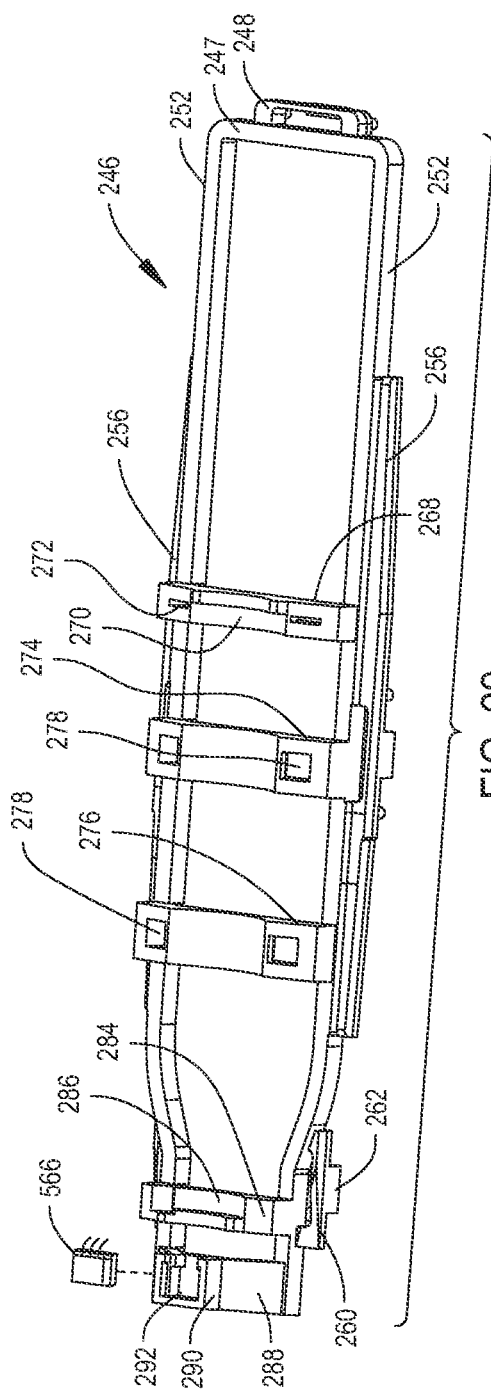
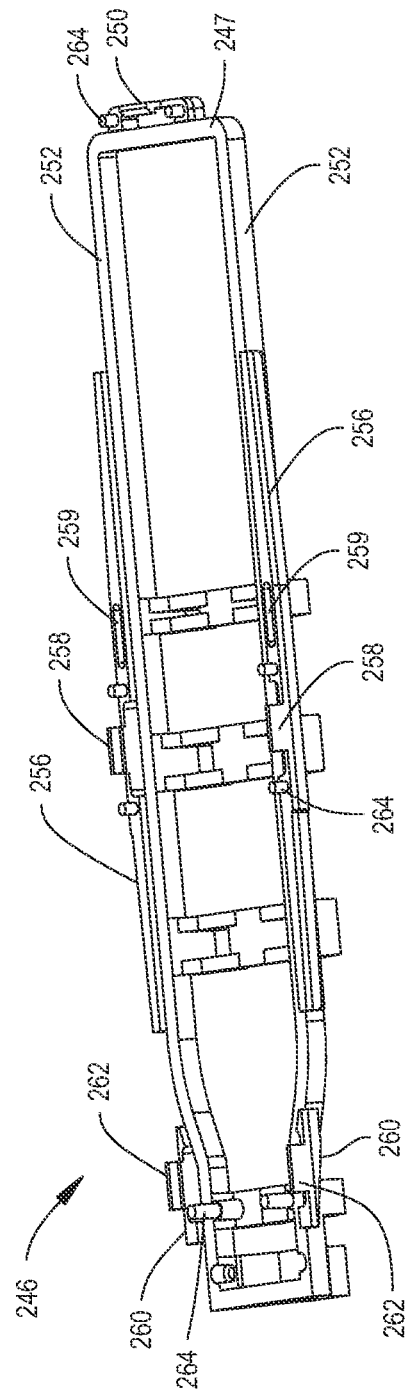
FIG. 29
FIG. 30

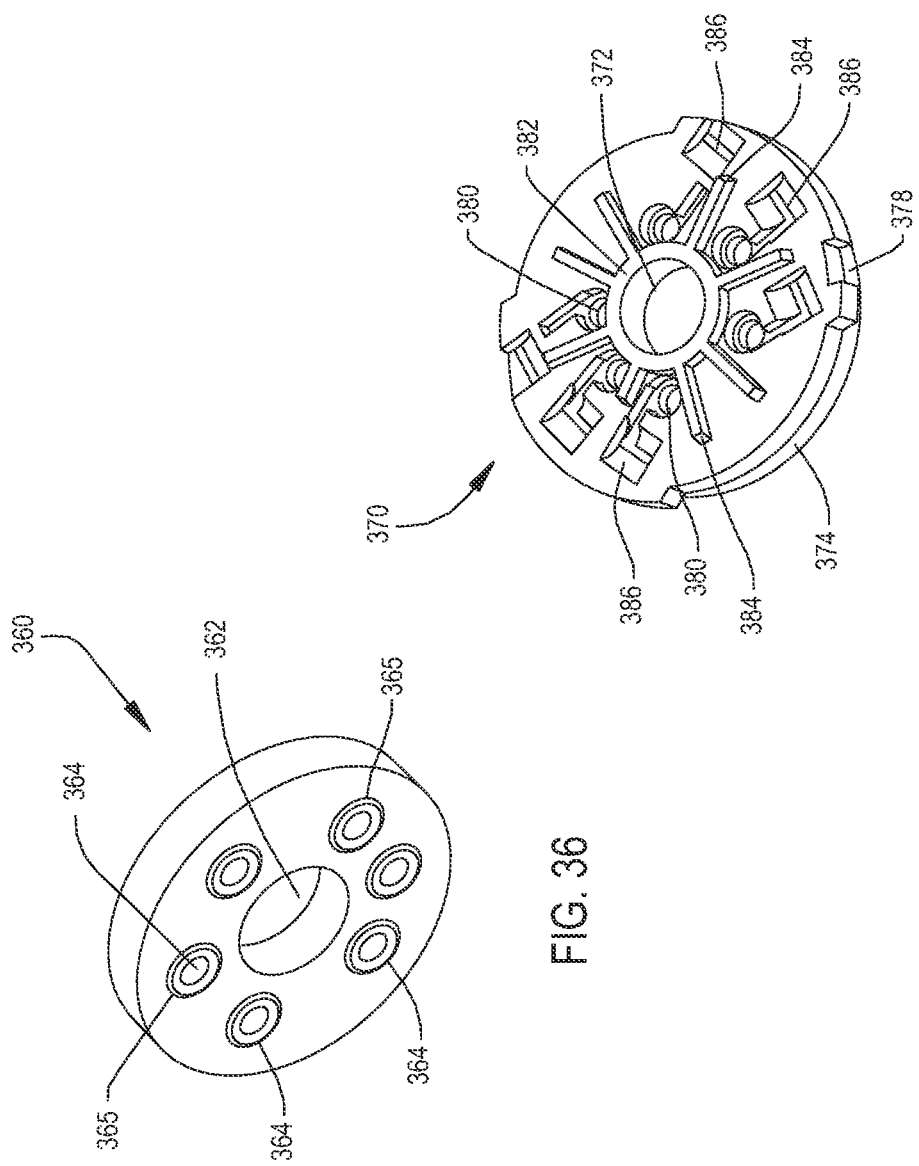

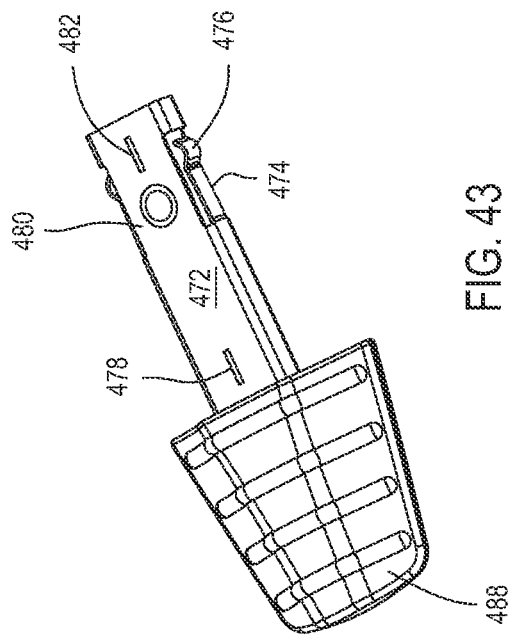
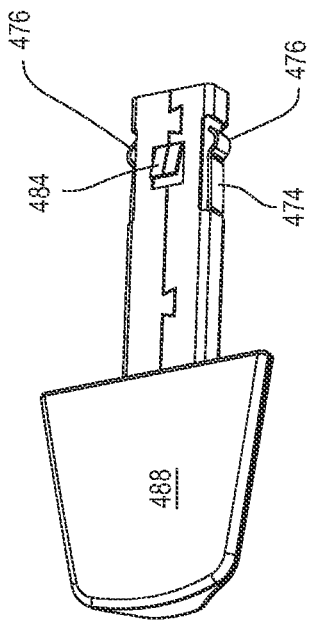
FIG. 43
FIG. 44

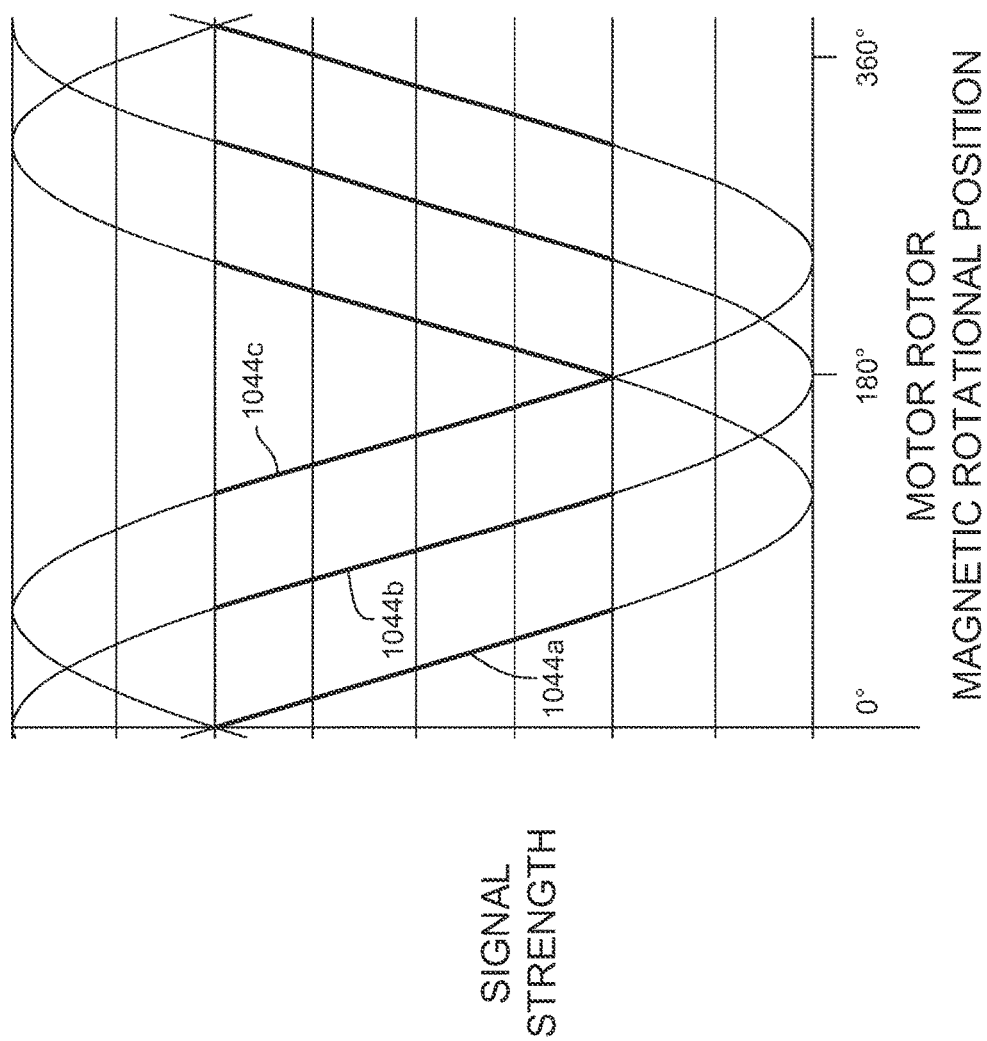

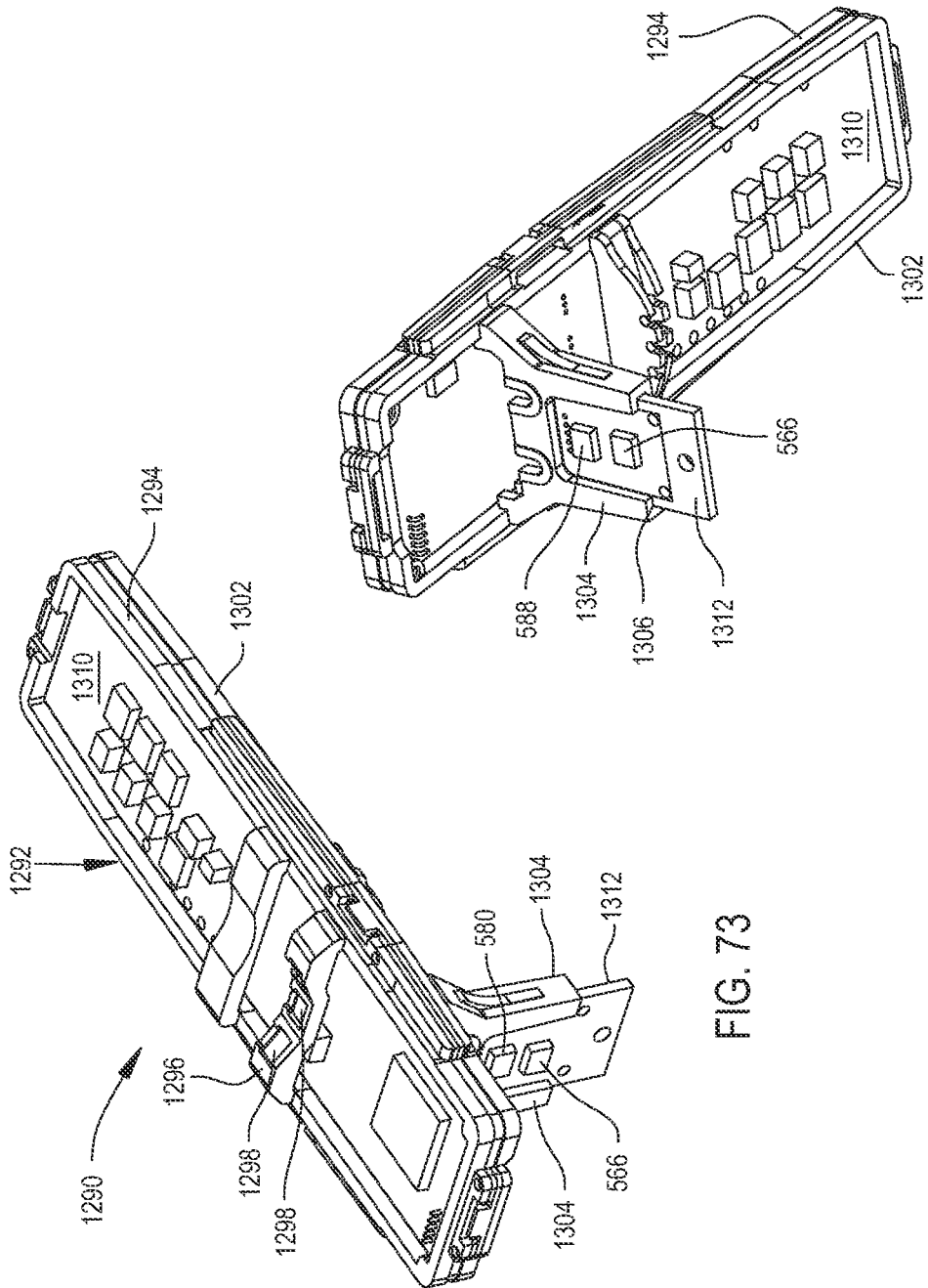

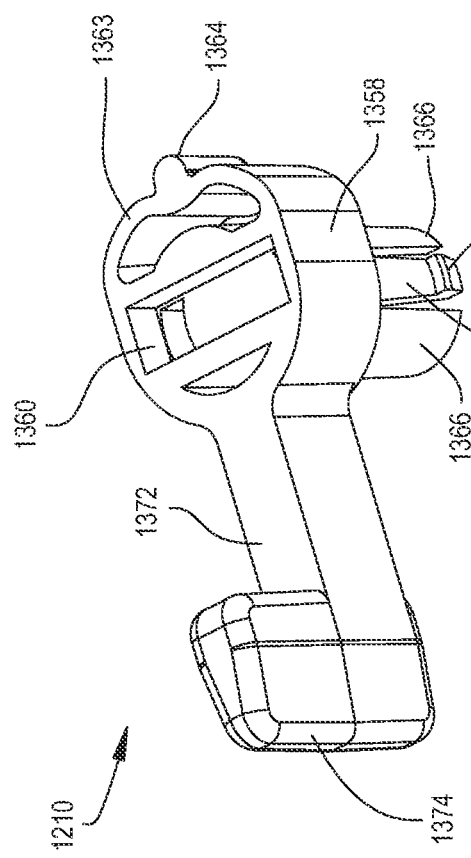
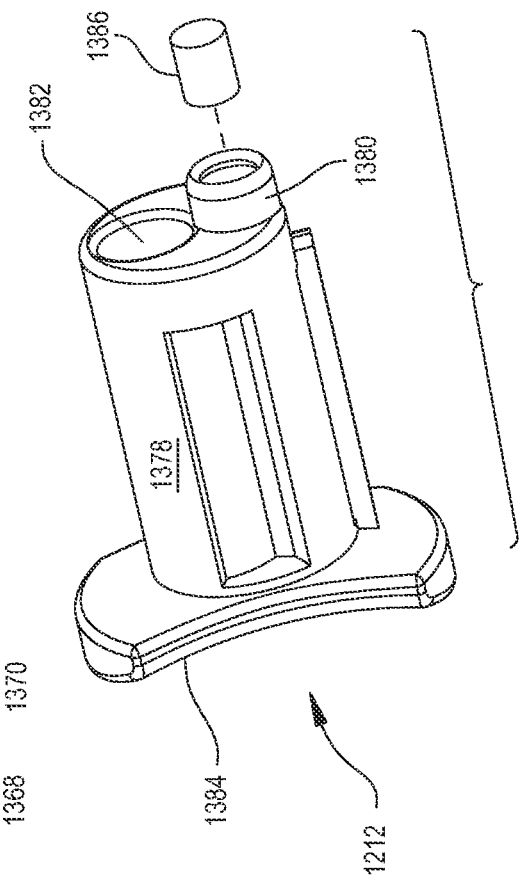

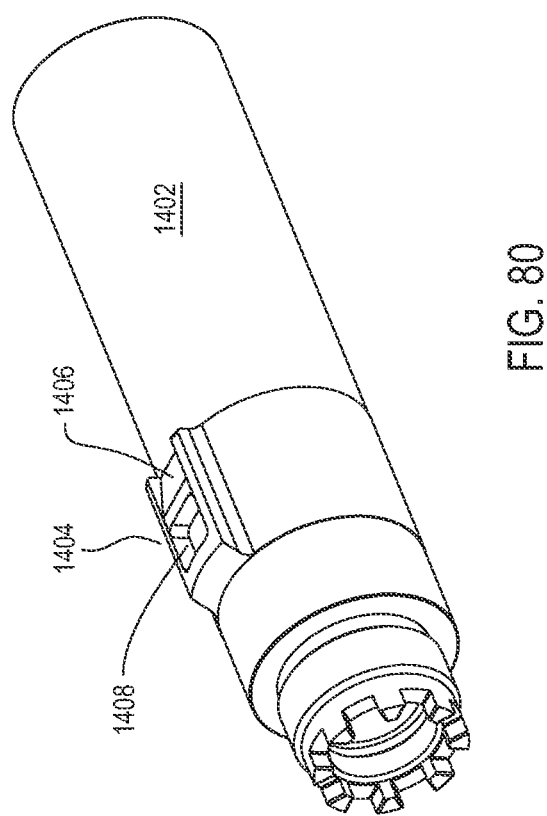

SURGICAL TOOL SYSTEM WITH A TOOL UNIT THAT INCLUDES A POWER GENERATING UNIT AND A BATTERY AND CONTROL MODULE THAT IS RELEASABLY ATTACHED TO THE TOOL UNIT FOR ENERGIZING AND CONTROLLING THE POWER GENERATING UNIT

RELATIONSHIP TO EARLIER FILED APPLICATIONS

This application is a continuation of PCT Pat. App. No. PCT/US2013/042464 filed 23 May 2013. PCT Pat. App. No. PCT/US2013/042464 is a non-provisional of U.S. Prov. Pat. App. No. 61/650,732 filed 23 May 2012. The contents of the above-listed priority applications are incorporated herein by reference.

FIELD OF THE INVENTION

The invention is related generally to a surgical instrument. More particularly, the invention is related to a powered surgical instrument having a tool unit and a separate battery and control module connectable to the tool unit to energize and control the tool unit.

BACKGROUND OF THE INVENTION

Powered surgical instruments are often used in surgical procedures such as orthopedic surgery. The surgical instruments can be of many types such as a rotary drill, reamer, wire driver, sagittal saw, oscillating saw, reciprocating saw, ultrasonic device, etc. Typically, the surgical instrument includes a housing or a shell. The housing holds the tool power generating components that outputs the energy applied to the surgical site. The tool may be a drill bit, bur, saw, ultrasonic cutting or cauterizing tip, etc. An energy application, such as a drill bit, a saw blade, a bur, an electrode or ultrasonic tip extends forward from the housing.

Some powered surgical tools are energized by a battery that is attached to the housing. Typically the battery includes its own case or housing. One or more rechargeable cells are disposed in the battery housing. A battery for charging this type of tool is disclosed in the Applicant's PCT App. No. PCT/US2012/064764 published as US Pat. Pub. No. 2014/0266057, the contents of which are explicitly incorporated herein by reference.

The use of a battery eliminates the need to provide a power cord connected to an external power source. The elimination of the power cord offers several benefits over corded surgical instruments. Surgical personnel using this type of instrument do not have to concern themselves with either sterilizing a cord so that it can be brought into the sterile surgical field surrounding the patient or ensuring that, during surgery, an unsterilized cord is not inadvertently introduced into the surgical field. Moreover, the elimination of the cord results in the like elimination of the tripping and tangling hazard, physical clutter, and field-of-view blockage that the cord otherwise brings to a surgical procedure. Specifically, when pulled or tangled during the surgical procedure, the cord can become unsterilized, can be pulled from the hands of the user, and can be fully or partially disconnected from a power socket thereby ceasing operation of the instrument and/or creating a potential for electrically shocking the patient. Also, the cord is prone to increased failure relative to other components of the instrument when subjected to steam sterilization, such as with an autoclave.

A powered surgical tool also includes a manually actuated switch or trigger. The practitioner using the tool actuates this switch to control both the on/off state and the operating state of the tool. The state of the trigger is monitored by a control circuit. If the tool is battery powered, this control circuit is typically in the tool housing. It is however known at least in the field of non-surgical tools to place this controller in the battery housing. Based on the state of the trigger this control circuit selectively applies energization signals from the cells integral with the battery to the tool power generating circuit. The control circuit thus controls the energization of the tool power generating circuit. The inventors' Assignee's U.S. Pat. No. 7,638,958, the contents of which are incorporated herein by reference discloses one such battery powered surgical tool.

The battery powered motorized surgical tools used today are relatively large in mass, 1.3 kg or more including the battery. The motors internal to these tools tend to output a minimum of 125 Watts of power. These tools are used for applications where significant amounts of power are required. These applications include large bone resection and removal procedures as part of knee or hip replacement procedure. These tools are also used for drilling and reaming bores into large bone such as femur.

Available battery powered surgical tools generally work well for the purposes for which they are intended. However, to date, it has proven difficult to provide a motorized battery powered motorized surgical tool that outputs power in the range of 25 to 125 Watts. These tools are used for such applications where a relatively small application of power is required in order to perform a delicate task. These types of procedures include osteotimies and fracture fixations. Typically these tools weight 150 grams or less. Many of these tools being small in size are elongated in structure, shaped like an oversized pen or pencil. This allows the practitioner holding the tools to hold the tool like pencil. This allows the practitioner to by moving the thumb and forefinger, precisely position the tools so that the tool can perform the desired task.

One reason that it is difficult to provide this type of battery powered tool is that it has proven difficult to provide package the components forming the tool as well as the attached battery, in a unit the practitioner can, with minimal strain hold between the thumb and forefinger.

SUMMARY OF THE INVENTION AND ADVANTAGES

This invention is related to a new and useful powered surgical tool assembly. The tool assembly of this comprises both a tool and battery unit that are relatively light in weight and that are designed to minimize ergonomic stress of the practitioner using the tool.

This invention consists of an assembly that includes a tool unit and a battery and control module. The tool unit is removably attached to the battery and control and module. The tool unit includes a power generating unit, a unit that converts electrical energy into a form in which the energy can be applied to a site on living tissue in order to perform a desired medical/surgical task. Typically the energy is applied through an applicator that is attached to or part of the tool unit. Often the tool unit includes a coupling assembly that both releasably holds the energy applicator to the tool unit and releasably connects the applicator to the power generating unit.

The battery and control module (BCM) includes one or more cells for hold charge that is applied to the tool power generating unit. Also internal to the BCM a tool unit controller that regulates the application of power to the tool unit. The BCM also includes either a trigger assembly or a tool sensor. The trigger includes a manually operated member the practitioner manipulates to control the actuation of the tool. The tool sensor even though not internal to the tool generates signals representative of the operating state of the tool. Based on the state of the trigger and/or the output from the tool sensor, the tool unit controller regulates the outputting of current from the cells to the tool power generating unit.

In many but not all versions of the invention the BCM includes both a trigger and the tool sensor.

It is a further feature of this invention that when the tool unit and BCM are assembled together, the assembly imposes minimal physical strain on the person using the assembly. This is accomplished in some versions of the invention by forming the tool unit so that tool unit has an elongated pencil like shape and by providing a BCM that when attached to the tool includes at least one battery that is located rearward of the proximal end of the tool.

It is a further feature of this invention that both the tool unit and BCM are able to withstand the harsh environment of autoclave sterilization. Specifically exposure to an atmosphere saturated with steam (water vapor) at temperatures in excess of 125° C. at pressures of 2 bar. This is accomplished in part by providing compliant seals around the electrical pins that project out from the BCM.

In many but not all versions of this invention, the tool unit motor functions as the tool power generating unit. In these versions of the invention, the BCM includes sensors that provide data regarding the magnetic rotational position of the motor rotor. Plural sensors are provided. The tool unit controller internal to the BCM selectively employs these sensor signals to provide a highly accurate indication of the rotational position of the rotor. Based on these position data, the tool unit controller is able to precisely regulate the sourcing of current by the cells to the windings of the motor.

The cell or cells internal to the BCM is/are rechargeable. The BCM is further designed so that BCM pins over which charge is outputted from the cell/cells to the tool power generating unit also function as the pins over which charging current is applied to the cell/cells for storage.

A further feature of the assembly of this invention is that when the charger to which the BCM is coupled performs more tasks that just the charging of the cells. Specifically, the charger is further able to test the tool unit controller internal to the BCM. This testing ensures that, when the BCM is attached to a new tool unit, the tool unit controller is correctly sourcing current.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 26 is a perspective view looking into the void space internal to the battery and control module of FIG. 23;

FIG. 29 is an exploded view of the upwardly directed portion of the upper frame of the chassis as well as the sensor attached to the frame;

FIG. 30 is perspective view of the downwardly directed portion of the chassis upper frame of FIG. 29;

FIG. 36 is a perspective view of the connector seal internal to the battery and control module;

FIG. 37 depicts the cap disposed over the connector seal;

FIG. 43 is a perspective view of the top surface of the finger tab and attached beam of the trigger switch;

FIG. 44 is a perspective of the undersurface of the finger tab and beam of FIG. 43;

FIG. 63 is a plot of the relative strengths of the signals emitted by the battery and control module tool unit power generating unit sensors as a function of the position of the rotor monitored by the sensors;

FIG. 73 is a perspective view of the top of the tool unit controller mounted to the chassis of the battery and control module of FIG. 64;

FIG. 74 is a perspective view of the bottom of the tool unit controller of FIG. 71;

FIG. 77 is a perspective view of the operating mode control switch of the switch assembly of FIG. 75;

FIG. 78 depicts the on/off control switch of the switch assembly of FIG. 75;

FIG. 80 is a perspective view of the main tube of a tool unit designed to be used with battery and control module of FIG. 64.

DETAILED DESCRIPTION OF THE INVENTION

I. First Embodiment

Figure 1:
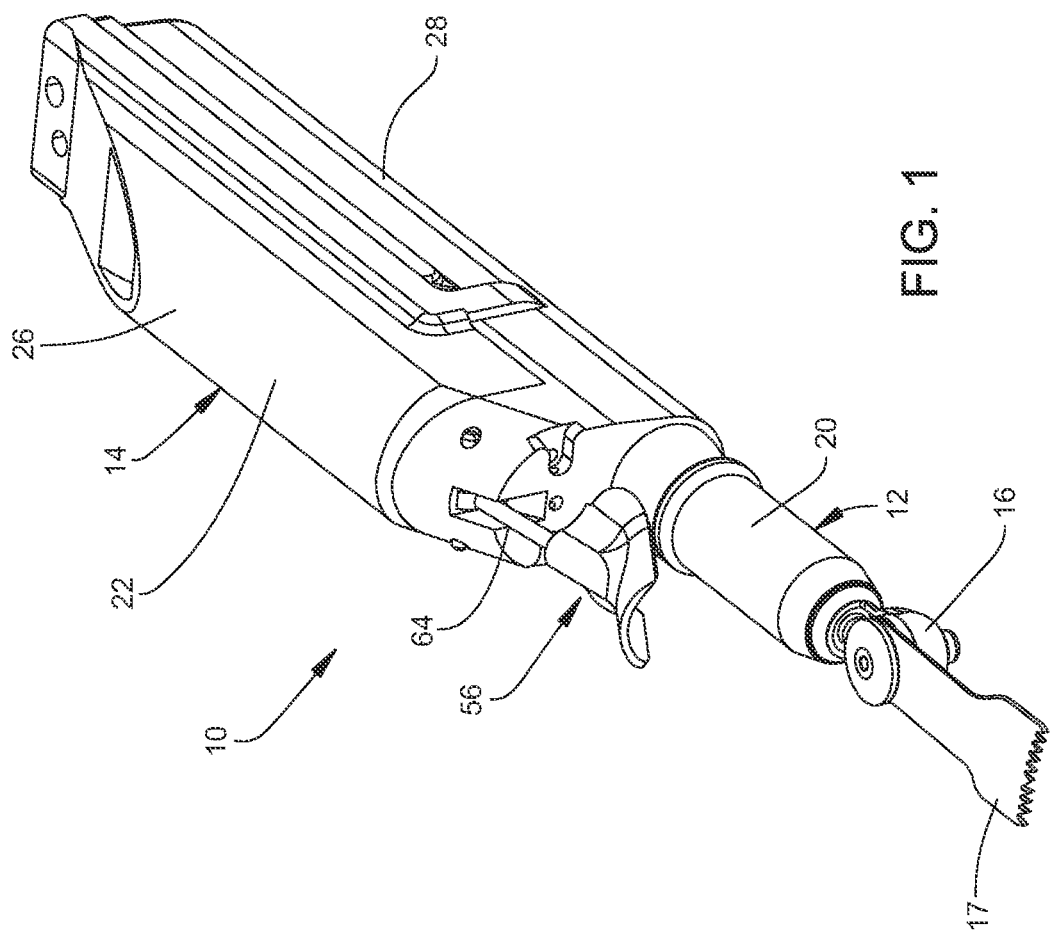
FIG. 1 is a perspective view of a surgical instrument including a tool unit and a battery and control module.
Figure 2:
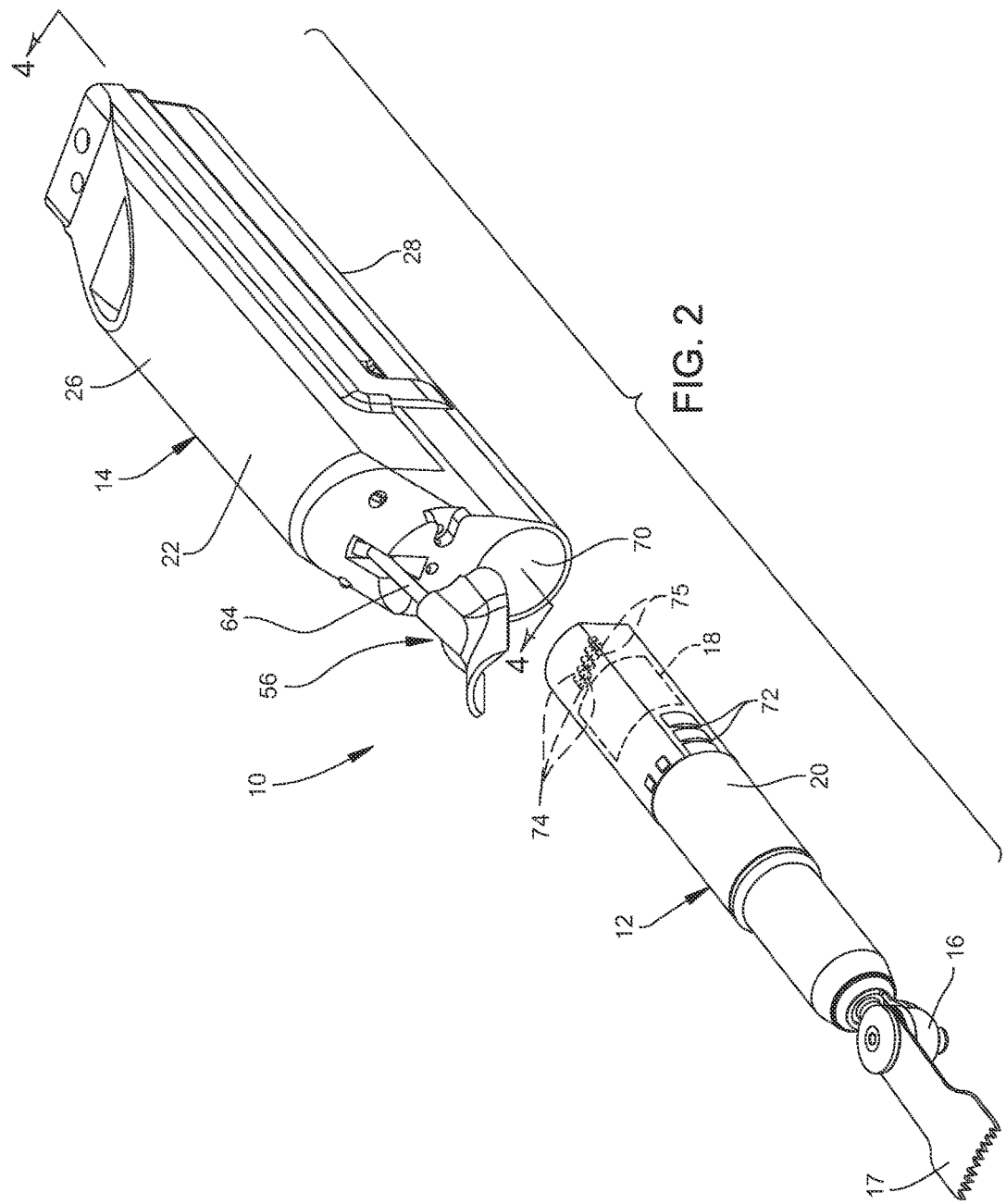
FIG. 2 is a perspective view of the surgical instrument with the tool unit disengaged from the battery and control module.

Referring to the Figures, wherein like numerals indicate like parts throughout the several views, a powered surgical tool assembly 10 is generally shown for use in surgical procedures such as orthopedic surgery. In certain embodiments, the surgical tool assembly has a pencil-grip configuration to allow a user to hold and grip the surgical tool assembly like a pencil. With reference to FIGS. 1 and 2, the surgical tool assembly 10 includes a tool unit 12 and a battery and control module 14. Battery and control module (BCM) 14 releasably engages the tool unit 12. The BCM 14 provides the power that energizes the tool unit 12. Battery and control module 14 also controls the application of the energization signals to the tool unit 14.

The representative tool unit 12 shown in FIGS. 1 and 2 is a sagittal saw configured to hold and drive an energy applicator 17. Here energy applicator 17 is a sagittal saw blade for cutting bone, ligaments, or other tissue. The saw blade can be used to cut small bones, such as bones in a hand or foot. Generally the device component integral with the tool unit that is applied to the medical/surgical site is known as an energy applicator.

In other embodiments, tool unit 12 may be a rotary drill, reamer, wire driver, oscillating or reciprocating saw, ultrasonic device or photonic device. Likewise, the energy applicator may be a drill bit, bur, saw, reamer, grinding disc, ultrasonic cutting or catheterization tip, laser, etc. The type of tool used is not intended to limit the present invention.

With continued reference to FIGS. 1 and 2, in the embodiment shown, the tool unit 12 includes a head 16 for supporting the energy applicator 17. The head 16 may be like that shown in U.S. Pat. No. 7,833,241 to Gant, entitled, "Surgical Saw Blade Coupler," hereby incorporated by reference. As disclosed therein, the head 16 is moveable between an open position in which the saw blade may be removed, exchanged or inserted, and a closed position. In other embodiments, the head 16 may be a collet for receiving a drill bit or bur, or another energy applicator.

A power generating unit 18 (shown as a dashed component in FIG. 2) is operatively coupled to the energy applicator 17 to actuate the energy applicator 17. In the depicted version of the invention, power generating unit 18 is a motor. The power generating unit 18 can rotate the energy applicator 17, oscillate the energy applicator 17 or reciprocate the energy applicator 17. In other embodiments, the power generating unit 18 may be a piezoelectric power generating unit, laser, an RF generator, or device electrical energy into signals that heat or vibrate the energy applicator 17.

Figure 3:
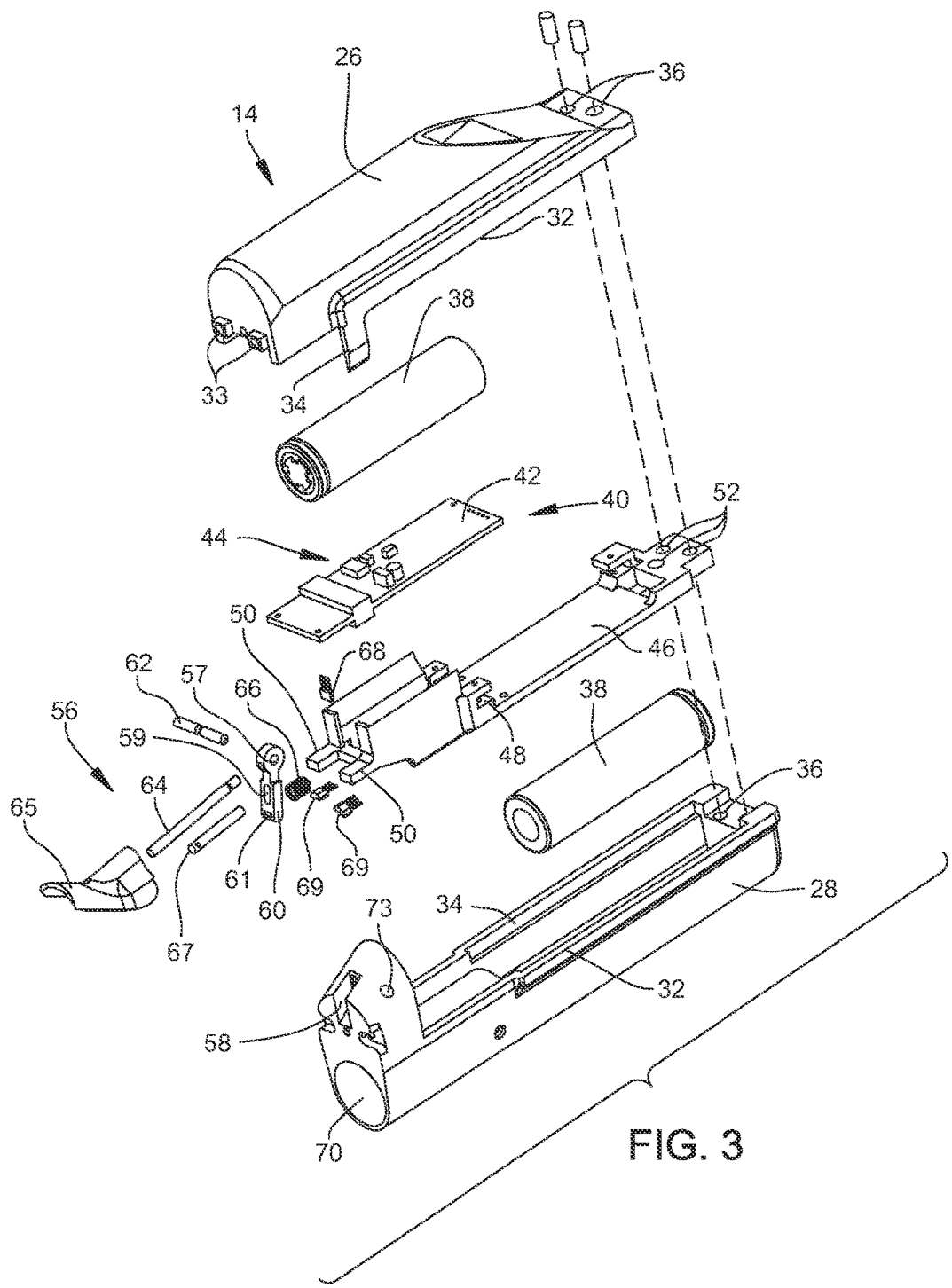
FIG. 3 is an exploded view of the battery and control module.
Figure 4:
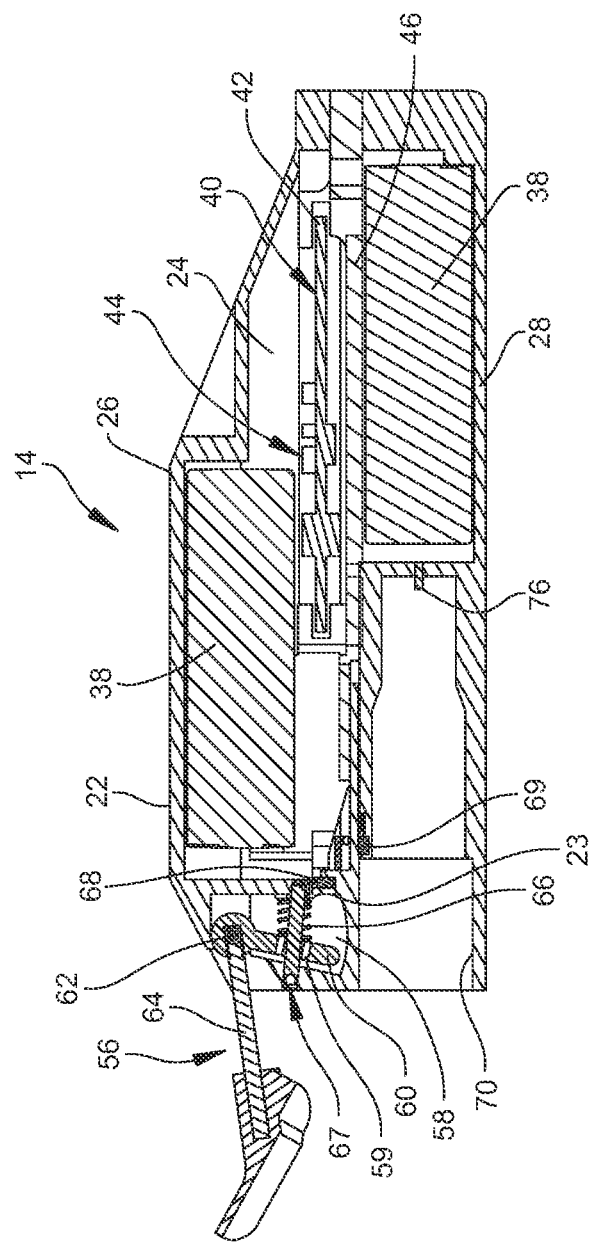
FIG. 4 is a cross-sectional view of the battery and control module along line 4 of FIG. 2.

With reference to FIGS. 2-4, a casing 20 sealingly encloses the power generating unit 18 and supports the head 16. The casing 20 is formed of metal or alternatively is formed of medical grade plastic such as, for example, polyether ether ketone (PEEK) or polyphenylsulfone. The tool unit 12 is configured to remain operational after multiple cycles of sterilization. Accordingly, the head 16, power generating unit 18, and casing 20 are formed of materials able to withstand repeated sterilization. As used herein, types of sterilization can include steam (such as with the use of an autoclave), gas plasma, ethylene oxide (ETO), hydrogen peroxide, and/or high pH solutions.

Battery and control module 14 includes a housing 22. The housing 22 defines a void space 24 (see cross-section of FIG. 4). The housing 22 isolates the void space 24 from the physical environment external to the housing 22. As the BCM 14 is subjected to the same sterilization process/processes to which the tool unit 12 is subjected without adversely affecting the components internal to the BCM.

Figure 16:
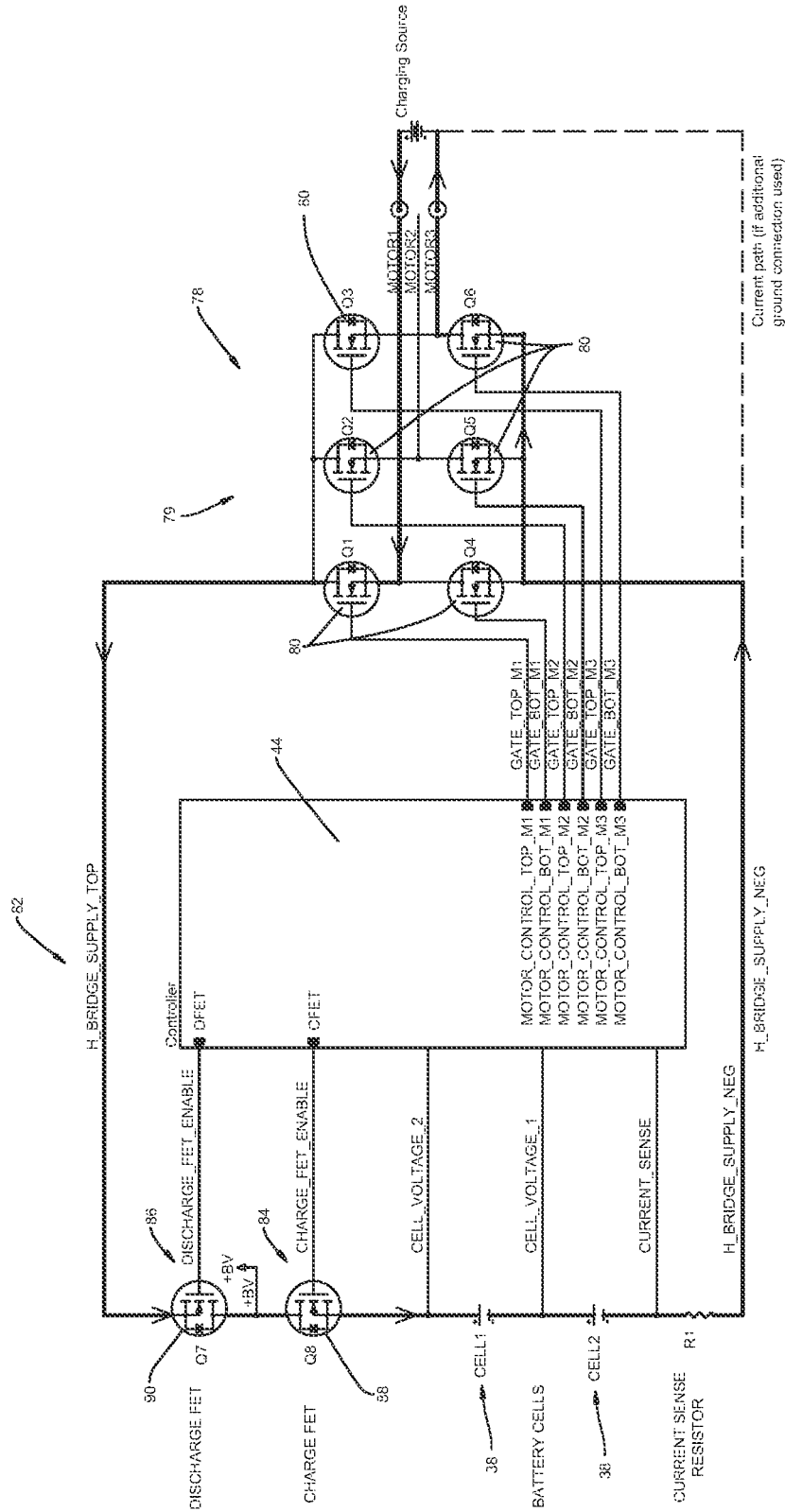
FIG. 16 is a schematic of a charging circuit of a control system of the battery and control module

At least one rechargeable cell 38 is disposed in the void space 24 of the BCM 14. Cell 38 is typically a lithium ion, nickel cadmium, or nickel-metal hydride cell. The rechargeable cell may be a capacitor or a micro fuel cell. Rechargeable cell 38 powers the power generating unit 18. In the depicted version of the invention the BCM has two cells 38. As seen in FIG. 16, cells 38 are series connected together.

A tool unit controller 40 is disposed in the void space 24 of the housing 22. Tool unit controller 40 is powered by the rechargeable cells 38. Tool unit controller 40 regulates the application of energization signals from the rechargeable cells 38 to the tool power generating unit 38. The tool unit controller 40 thus regulates the actuation of tool unit 12. As set forth further below, the energization signals are sourced through and return over BCM contacts 76, 77, e.g., male contacts shown in FIG. 7, and tool unit contacts 74, 75, e.g., female contacts shown in FIG. 2, as set forth further below. Specifically, as set forth further below, the BCM 14 includes three BCM contacts 76 that connect with three tool unit contacts 74, respectively, on the tool unit 12 to transmit power from the BCM 14 to the tool unit 12. The BCM 14 includes two BCM contacts 77 that connect with two tool unit contacts 75, respectively, on the tool unit to exchange other types of signals. These other signals are data and command signals. It should be appreciated that the tool unit 12 can include any number of tool unit contacts 74, 75 and the BCM 14 can include any number of BCM contacts 76, 77, respectively.

Tool unit controller 40 includes a circuit board 42. A controller 44 (FIG. 16) is mounted on the circuit board 42. The controller 44 includes a processor (not identified) and memory (not numbered) such as non-volatile random access memory (NOVRAM). As set forth further below, the controller 44 can also include one or more of a plurality of sensors. For example, the sensors can sense conditions of the rechargeable cell 38, position and/or state of the power generating unit 18, temperature of components, engagement of the tool unit 12 with the BCM 14, and/or status of a user-actuated switch 56.

Switch 56 is attached to BCM housing 22. Switch 56 is actuated by the practitioner to control operation of tool unit power generating unit 18. In the embodiment shown, switch 56 is a trigger that moves relative to the housing 22. In this embodiment, the trigger pivots relative to the housing 22.

Figure 5:
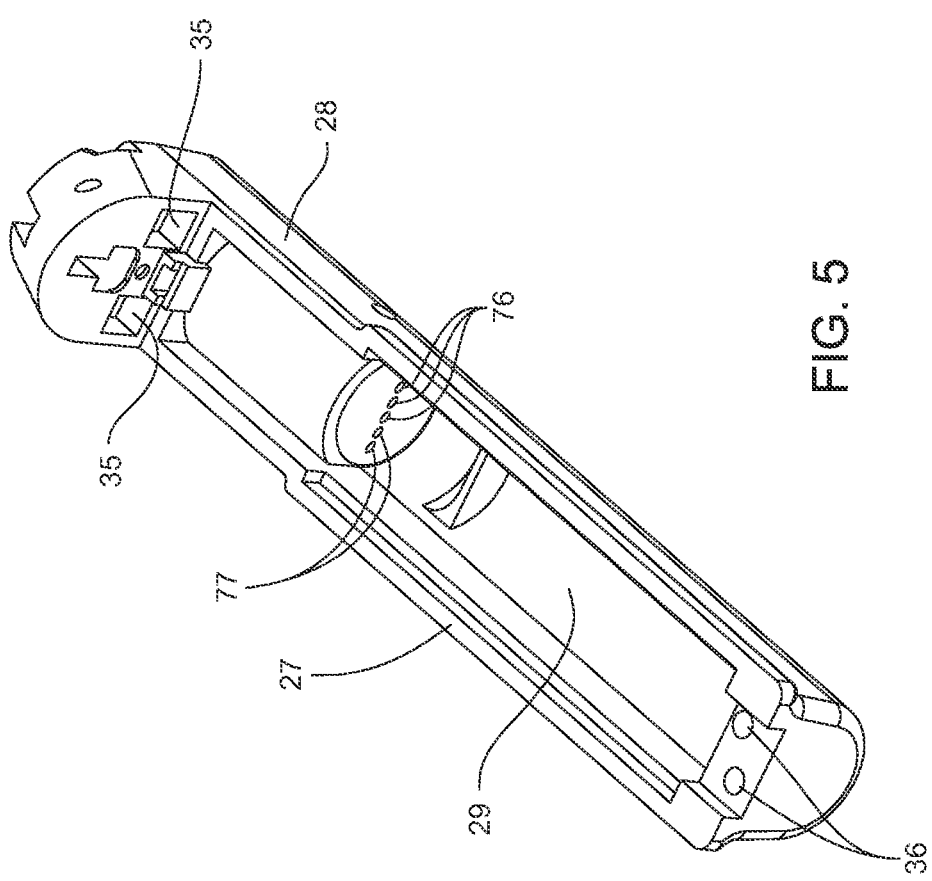
FIG. 5 is a perspective view of a lower section of a housing of the battery and control module.

Housing 22 includes upper shell 26 and lower shell 28 sealed together to form the void space 24 therebetween. Upper shell 26 and lower shell 28 are typically sealed together by laser or ultrasonic welding, but it is appreciated that the housing 22 can include any number of sections sealed together using other methods such as adhesive bonding, solvent fusing, welding, etc. With reference to FIG. 5, a portion of the void space 24 includes cavities 29 defined by the upper shell 26 and the lower shell 28.

Lower shell 28, as shown in FIGS. 5-8, is formed to have an upwardly directed surface 27. Upper shell 26, as shown in FIGS. 9-12, present corresponding downwardly directed surfaces 30. When the BCM 14 is assembled shells 26 and 28 are placed together so that surfaces 27 and 30 abut. Shells 26 and 28 are welded or otherwise secured together along the interface between surfaces 27 and 30. In the embodiment shown in the Figures, the upper shell 26 and the lower shell 28 are sealed directly to each other, i.e., in direct contact, except along the chassis 46, as shown in FIG. 4 for example, in which case the upper shell 26 and the lower shell 28 are both sealed along the chassis 46. In other words, along this portion, the upper shell 26 and the lower shell 28 are sealed to each other by sealing to the intermediately disposed chassis 46. Upper shell 26 and/or lower shell 28 can also include interlocking projections 34 and/or can include aligned holes 36 for being fastened, heat-staked, etc., to lock the upper shell 26 and the lower shell 28 together.

Figure 6:
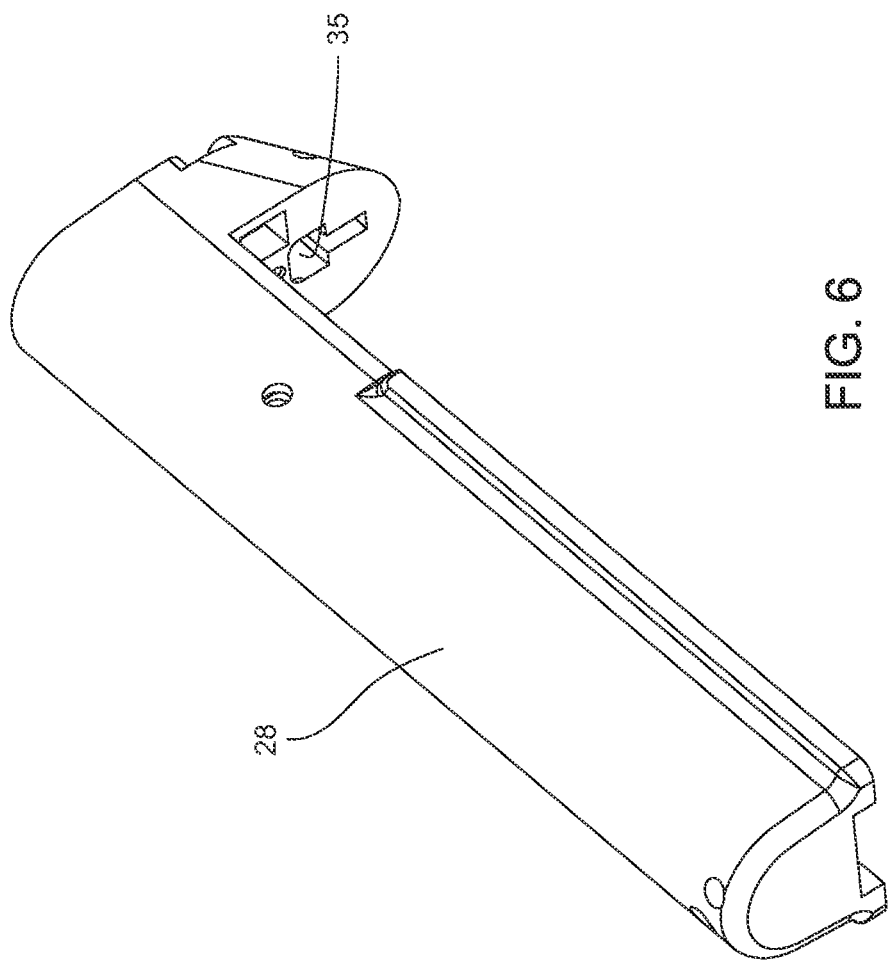
FIG. 6 is another perspective view of the lower section of the housing of the battery and control module.
Figure 9:
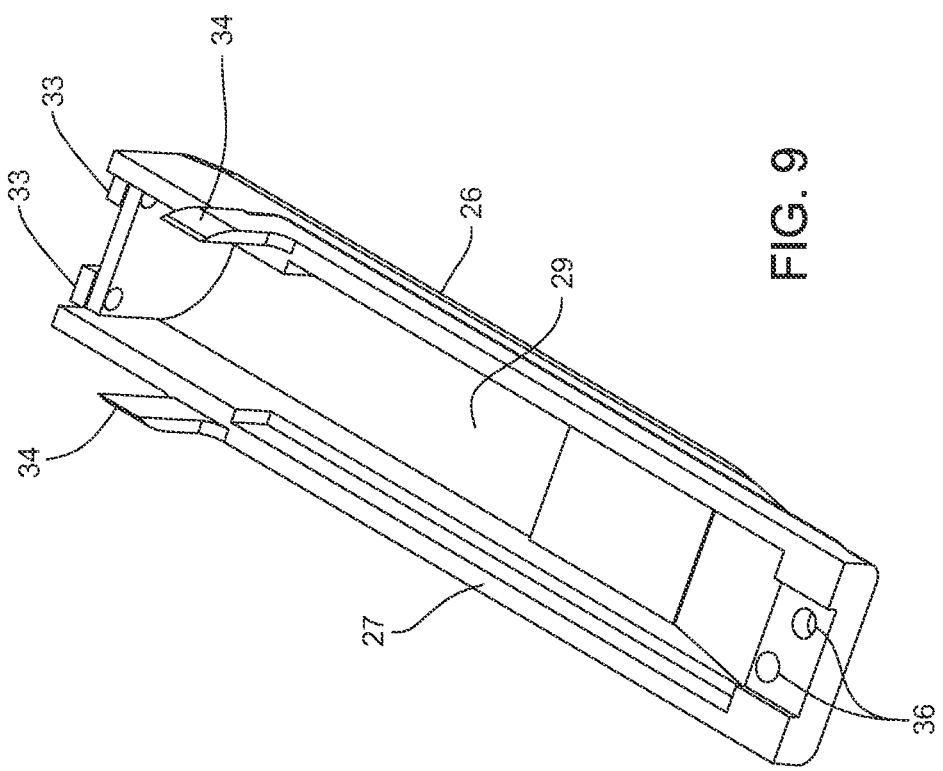
FIG. 9 is a perspective view of an upper section of the housing of the battery and control module.
Figure 10:
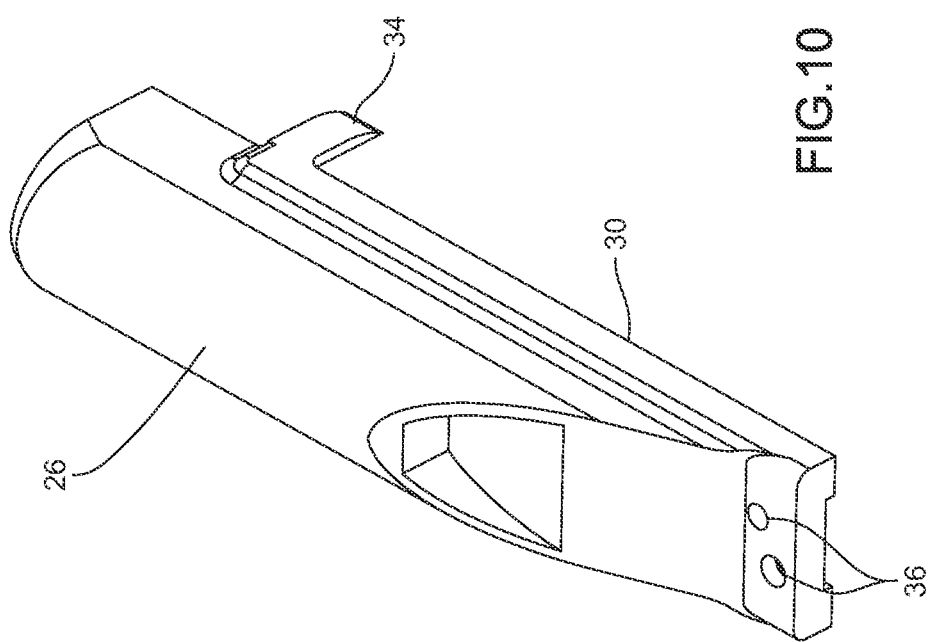
FIG. 10 is another perspective view of the upper section of the housing of the battery and control module.
Figure 11:
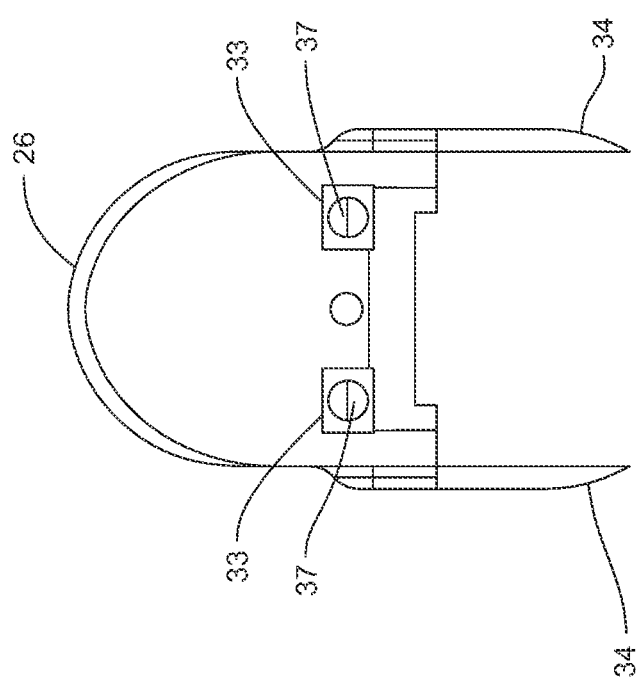
FIG. 11 is an end view of the upper section of the housing of the battery and control module.
Figure 12:
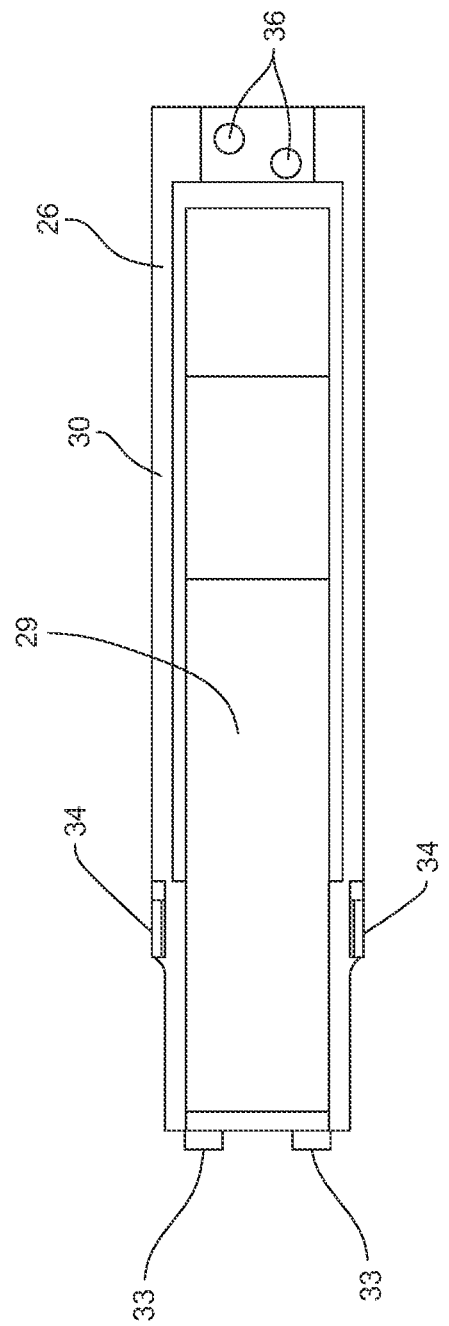
FIG. 12 is a plan view of the upper section of the housing of the battery and control module.

As best shown in FIGS. 3 and 9, the upper shell 26 includes blocks 33. As best shown in FIGS. 5 and 6, the lower shell 28 includes cutouts 35 receiving the blocks 33, respectively. Fasteners 37 extend through holes 39 in the lower shell 28 and engage the upper shell 26.

Shells 26, 28 are formed of medical grade plastic such as, for example, polyether ether ketone (PEEK) or polyphenylsulfone, or alternatively are formed of metal. However, it is appreciated that the housing 22 can be formed of any type of suitable material without departing from the nature of the present invention. The BCM 14 is also configured to remain operational after multiple cycles of sterilization and cleaning and thus is configured to withstand repeated sterilization.

Housing 22 permanently encloses the rechargeable cell 38 in the void space 24. In other words, once assembled to form the void space 24, the housing 22 is configured to retain the rechargeable cell 38 for the useful life of the BCM 14. Power source 38 is configured to be recharged while retained in the void space 24, i.e., without removing the rechargeable cell 38 from the housing 22.

Data identifying tool unit 12 is read from a memory module (not shown), such as NOVRAM, disposed on the tool unit 12. The memory module is configured to be read by the controller 44 when the tool unit 12 engages the BCM 14 through one or more battery and control module contacts 77, e.g., male contacts, and tool unit contacts 75, e.g., female contacts, as set forth further below. This can be accomplished through a separate channel or electrical connection, e.g., direct electrical communication or wireless communication, established when the tool unit 12 engages the BCM 14. The tool identification data is transmitted over this channel to the controller 44. The controller 44 then accesses the corresponding operating parameters from memory and operates the power generating unit 18 accordingly.

BCM 14 is designed to receive different types of tool units 12. These tool units include units designed to drive a rotary drill, a reamer, wire, reciprocating saw, an oscillating saw or a sagittal saw. The data controller 44 reads from the tool unit memory is used by the tool unit controller 40 to configure the BCM 14 specifically for that tool unit 12.

The tool unit controller 40 includes components (not illustrated) for providing input in addition to the input received from switch 56. For example, the tool unit controller 40 can include a radiofrequency transceiver for receiving a radiofrequency signal to control the speed of the power generating unit 18. The radiofrequency signal can be generated as a function of the depression of a foot pedal (not shown). This foot pedal is depressed by the practitioner to, for example, control the operation of tool unit 12. Tool unit controller 40 can include a piezoelectric pickup for voice activation by the user of the surgical tool assembly. The tool unit controller 40 can also communicate with a hospital information network.

Figure 13:
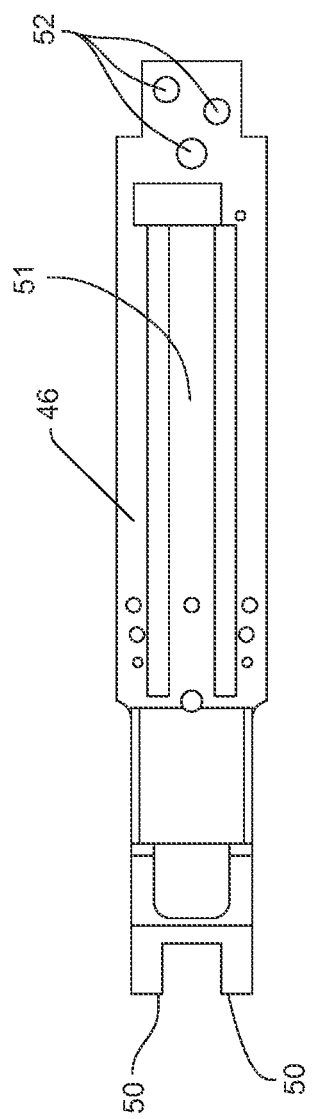
FIG. 13 is a plan view of a chassis of the battery and control module.
Figure 14:
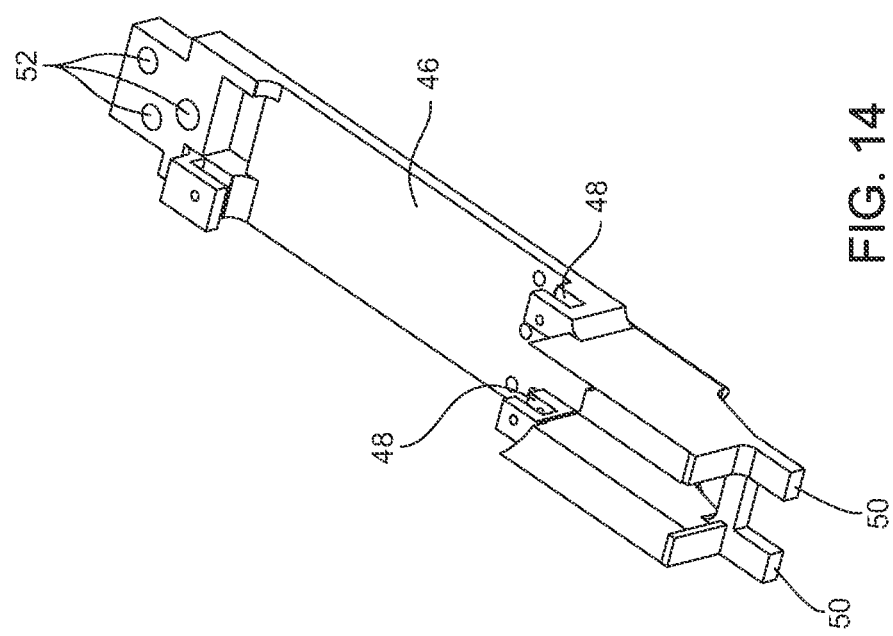
FIG. 14 is a perspective view of the chassis of the battery and control module.
Figure 15:
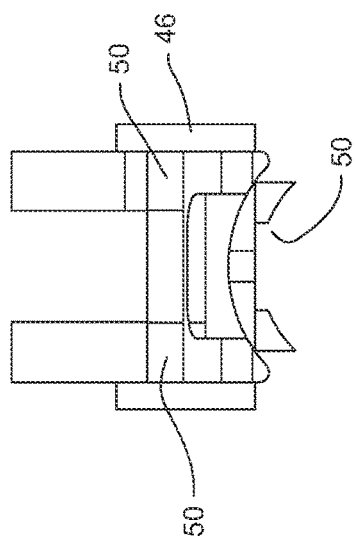
FIG. 15 is an end view of the chassis of the battery and control module.

The depicted BCM 14, as shown in FIGS. 3-4, includes a chassis 46. Chassis 46 supports the circuit board 42. Chassis 46 is mounted to the housing 22. In this version of the invention, the outer perimeter of chassis 46 is sandwiched between the upper 26 and lower 28 shells. Chassis 46 is formed with notches 48 that receive the circuit board 42. Protrusions 50 on the chassis 46 engage the housing 22. Specifically, the protrusions 50 are seated in cutouts 35 formed in the lower shell 28. Additionally, the chassis 46 and shells define aligned holes 52 for being fastened, heat-staked, etc., to interlock the upper shell 26, chassis 46, and lower shell 28 together. As shown in FIG. 13, the chassis 46 can define a cutout 51 for fitting around the rechargeable cell 38.

Tool unit controller 40 includes at least one sensor 69, shown in FIGS. 3 and 4, for measuring a condition associated with an operating state of the power generating unit 18 of the tool unit 12. For example, in versions of the invention in which the tool power generating unit is a motor, sensor 69 monitors and generates output signals representative of the rotational position of the tool rotor. One such sensor capable of generating signals representative of this rotor rotational position is a Hall effect sensor. A Hall effect sensor generates signals that vary with the sensed magnetic field. The magnetic field adjacent a motor rotor is a function of the rotational position of the rotor. Other sensors may generate sensor signals as a function of the operating rate of the power generating unit; the temperature of a component of the tool generating unit; the voltage applied across or the current applied to the power generating unit. The sensors may also measure a specific spectrum of light that the tool unit 12 emits as a function of the operating state of the power generating unit.

The tool unit controller 40 of FIG. 3 includes two sensors 69. Each of these sensors is a Hall effect sensor that outputs an analog signal of the magnetic field sensed by the sensor. Two sensors are provided because the output signals from plural Hall effect sensors is typically what is needed to provide an accurate representation of motor rotor position. Sensors 69 are disposed within housing void space 24 of the housing 22 so as to be isolated from the external environment. Sensors 69 thus measure the operating state of the power generating unit 18 through the casing 20 of the tool unit 12 and the housing 22 of the BCM 14.

As best shown in FIGS. 3 and 4, in the depicted version of the invention switch 56 is pivotally mounted to the housing 22. The lower shell 28 of the BCM 14 defines a pocket 58. Switch 56 includes is mounted to BCM housing 22 by a connector 60. While not specifically identified it can be seen that the connector has a ring-shaped head. A rectangular shaped body, also not identified, extends downwardly from the head. Connector 60 is further shaped so that head and body lie in planes that are perpendicular to each other. The connector 60 is seated in lower shell pocket 58. Connector 60 is formed so that a notch 57 extends side to side through the major faces of the connector head. A pin 62 extends through notch 57 in the connector 60. The opposed ends of pin 62 seat in opposed bores 73 formed in the lower shell 28 (one bore 73 identified). Bores 73 extend into notch 57. Connector 60 is thus pivotally connected to the lower shell 28.

Switch 56 includes a lever 64. The proximal end of lever 64 is seated in a closed end bore formed in connector 60. (Here "proximal" is understood to mean towards the practitioner holding the tool assembly 10, away from the site to which the energy applicator 17 is applied. "Distal" is understood to means away from the practitioner holding the tool assembly 10, towards the site to which the energy applicator is applied.) The bore in the connector (not identified) extends inwardly from the outer circumferential surface of the head of the connector 60. Connector 60 is mounted to the lower shell 28 so the bore extends distally forward. A finger pad 65 is fixed to the opposing distal end of the lever 64. The finger pad 65 is configured to receive a finger of the practitioner. Depression of the finger pad 65 exerts rotational force on the lever 64 and connector 60.

A spring 66, such as a coil spring, is disposed in notch 58. Spring 66 is disposed about a pin 67. Pin 67 is fixed at the proximal end into a bore that opens into the distally directed face of the lower shell 28. The distal portion of pin 67 extends through an elongated slots slot 59 formed in the body of connector 60. Spring 66 is thus compressed at one end between the distally directed face of shell and at the opposed end between the proximally directed surface of the body of connector 60. The force spring 66 imposes on connector 60 urges the connector body away from lower shell 28. This force is transferred through the connector 60 so as that, in the absence of the application of an overriding manual force, the switch finger pad 65 is normally pivoted away from the underlying tool unit 12. It should be appreciated that switch 56 is physically isolated from void space 24 internal to the BCM 14. In other words, no portion of the input device 56 extends into the void space 24.

Internal to the BCM 14 there is at least one sensor 68 that monitors the state, the position, of switch 56. In some versions of the invention sensor 68 a sensor sensitive to local magnetic fields. One specific type of sensor that may be employed is a Hall sensor. In these versions of the invention, a magnet is mounted to one of the moving components of the switch 56. In the depicted version of the invention a magnet 61 is mounted to the end of the connector 60 spaced from the connector head. Sensor 68 measures the relative position of the body of the connector 60 according to any suitable method, such as measuring magnetic field strength or direction between the sensor 68 and the connector 60 as the switch is depressed. It should be appreciated that the material forming the shells 26 and 28 is material through which the magnetic fields are able to flow with attenuation and distortion levels that do not affect the ability of the sensor 68 to output signals representative of switch position.

The signal output by sensor 68 is applied to tool unit controller 60. The tool unit controller, uses the signal from sensor 68 to determine the practitioner-desired operating state for tool assembly 10. In the embodiment shown, the magnetic field is sensed through cowl portion of the la wall of the upper shell 26 without requiring any mechanical penetration through the wall. Alternatively, the sensor 68 may measure the position of the connector 60 relative to the housing 22 in any suitable fashion.

As best shown in FIG. 3, sensor 68 and sensors 69 are mounted on the chassis 46 in the housing 22. The sensor 68 and sensors 69 are disposed entirely within the void space 24 of the housing 22 such that the sensor 68 and sensors 69 are completely isolated from the environment external to the housing 22.

It is appreciated that the BCM 14 can include more than one input device. For example, in such a situation, one input device can control the head 16 in a forward direction and the other input device can control the head 16 in a reverse direction. As another example, one input device can control speed of the head 16 and the other input device can control direction of the head 16. When the BCM 14 includes more than one input device, the tool unit controller 40 can include at least one sensor 68 for each input device. It is also appreciated that, while the input device 56 is shown in the figures as a trigger, the input device 56 can be any type of input device such as buttons, dials, etc., that communicate with the controller 44.

As set forth above, housing 22 sealingly encloses the rechargeable cell 38 and the tool unit controller 40 in the void space 24. Housing 22 also supports the input device 56 external to the void space 24 with respect to sensor 68 and sensors 69. This configuration allows the BCM 14 to remain operational after multiple cycles of sterilization with high temperature and pressurized steam with the use of an autoclave.

Battery and control module housing 12 is designed to releasably receive the tool unit 12. As seen in FIGS. 2-4, the BCM lower shell 28 is shaped to define a cavity 70 configured to receive the casing 20 of the tool unit 12. The casing 20 of the tool unit 12 and/or the housing 22 of the BCM 14 include locking features 72 for releasably engaging the holding the casing in the cavity. The locking features 72 can be releasable detents that interact with corresponding detent pockets, snap-lock features, and the like. The locking features 72 can also include one or more buttons (not shown) for releasing the casing 20 from the cavity 70.

Figure 7:
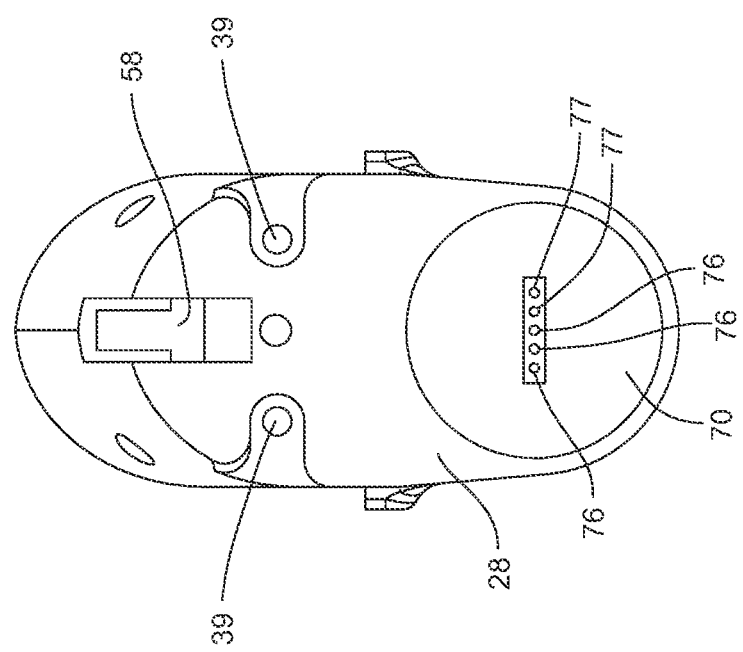
FIG. 7 is an end view of the lower section of the housing of the battery and control module.
Figure 8:
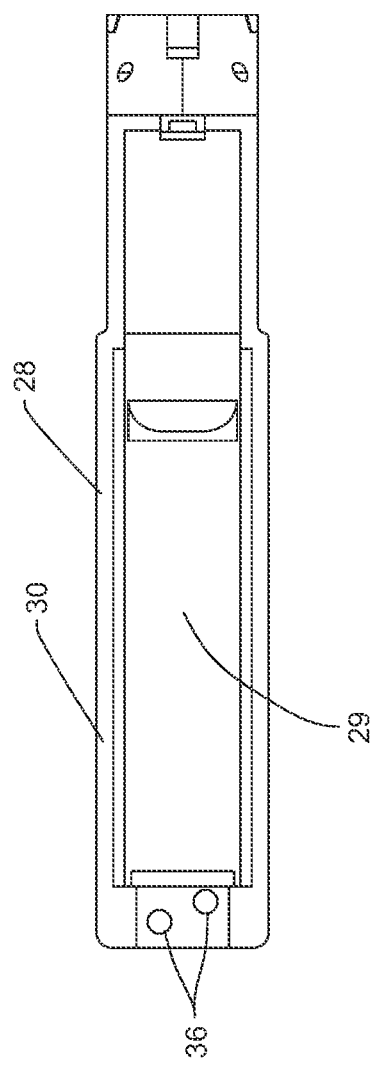
FIG. 8 is a plan view of the lower section of the housing of the battery and control module.

Tool unit 12 and BCM 14 are configured to be in electrical communication with each other when the tool unit 12 is engaged with the BCM 14 in the cavity 70. Accordingly, tool unit 12 includes tool unit contacts 74, as shown in FIG. 2, and BCM 14 includes BCM contacts 76, as shown in FIG. 7. When the tool unit 12 is engaged with the BCM 14 in the cavity 70, the tool unit contacts 74 and the BCM contacts 76 are aligned such that the tool unit contacts 74 are in contact with and communicate with the BCM contacts 76, respectively. The tool unit contacts 74 are typically female contacts and the BCM contacts 76 are typically male contacts that engage the female contacts when the tool unit 12 is engaged with the BCM 14. For example, the tool unit contacts 74 can be sockets and BCM contacts 76 can be pins that are engageable with the sockets. However, it should be appreciated that the tool unit contacts 74 and the BCM contacts 76 can be any type of corresponding contacts without departing from the nature of the present invention.

From FIGS. 1 and 4 it should be understood that when the tool unit 12 is attached to BCM 14, the proximal section of tool unit 12 is disposed under one of the cells 38. As a result of this design feature of tool assembly 10 an appreciable portion of the mass of the assembly 10 is located approximately 3 to 5 cm proximally from finger pad 65. This facilitates the use and manipulation of the tool assembly like a pencil, paint brush or other elongated implement. More particularly the tool can be held so that the distal end of the tool unit rests on the side surface of the middle finger while the section of the assembly in which the assembly center of gravity is located rests either on the web between the thumb or the forefinger or immediately behind this portion of the hand. Given this location of the center of gravity of the tool assembly 10, the practitioner does not have to exert appreciable effort to, with the thumb and middle finger, hold the assembly in the desired position.

Contributing to the ergonomic ease of using the tool is that finger pad 65 is located a short distance forward of the center of gravity. This makes it possible to with minimal ergonomic effort use the forefinger to control the actuation of switch 56. It should likewise be appreciated that with the tool unit, not including the energy applicator 17, extends approximately 6 to 9 cm forward of the BCM housing 22. This means that the portion of the tool the practitioner manipulates with the thumb and forefinger are small in volume, at least in comparison to the proximal portion of the assembly 10.

It is appreciated that the tool unit 12 and the BCM 14 shown in the Figures include a total of five tool unit contacts 74, 75 and five corresponding battery and control module contacts 76, 77, respectively. As set forth above, in such a configuration, for example, three of the tool unit contacts 74 and a corresponding three of the BCM contacts 76 are the contacts over which energization signals are sourced to and returned from the tool power generating unit. The other two of the tool unit contacts 75 and the other two of the BCM contacts 77 are the contacts over which the controller 44 reads data from the tool unit memory. In an alternative embodiment, the tool unit 12 and the BCM 16 can each include a sixth corresponding BCM contact used as a logic power connection (e.g., 3.3 V), which would allow for a bidirectional data line. It is appreciated that the tool unit 12 and the BCM 14 can include any number of tool unit contacts 74 and BCM contacts 76, respectively, without departing from the nature of the present invention.

Tool unit contacts 74, 75 extend through the casing 20 and are in communication with the power generating unit 18. Battery and control module contacts 76, 77 are in communication with the rechargeable cell 38, through the controller 44. The BCM contacts 76, 77 extend through the housing 22. Battery and control module contacts 76, 77 are in electrical contact with the tool unit contacts 74, 75 when the tool unit 12 is received by the housing 22 of the BCM 14. This electrical contact allows the BCM 14 to energize the power generating unit 18 of the tool unit 12.

The BCM contacts 76, 77 are sealed to the housing 22. Specifically, seals (not shown) are typically disposed between the BCM contacts 76, 77 and the housing 22. The seals can be, for example, O-rings, energized seals, gaskets, elastomeric compound, etc. These seals are configured to maintain sealing capability after multiple cycles of sterilization.

The BCM housing 22 encloses the void space 24 except for the area through which the BCM contacts 76 extend. As set forth above, seals are disposed between the BCM contact 76, 77 and the housing 22.

As shown in FIG. 4, the BCM contacts 76, 77 are disposed in the cavity 70 and, more specifically, are disposed at an end of the cavity 70. Tool unit contacts 74, 75 are disposed at a corresponding end of the tool unit 12 to align with the BCM contacts 76, 77 when the tool unit 12 is engaged with the BCM 14 in the cavity 70.

Battery and control module 14 can be interchangeably used with multiple types of tool units 12. For example, the BCM 14 can be interchangeably used with separate tool units 12 having different types of heads 16 or that hold different types of tools. Similarly, the tool unit 12 can be interchangeably used with similar BCMs 14. For example, one BCM 14 that has a rechargeable cell 38 that requires recharging, e.g., a drained rechargeable battery, can be replaced with another BCM 14 that has charged rechargeable cell 38.

Battery and control module contacts 76 are configured to couple with a recharging unit (not shown) to recharge the rechargeable cell 38. Specifically, the cavity 70 can receive the recharging unit when the cavity 70 is unoccupied by a tool unit 12. The recharging unit is configured to be received in the cavity 70 and engage the BCM contacts 76. In other words, the recharging unit includes recharging contacts oriented to engage the BCM contacts 76 when the recharging unit is received in the cavity 70. Specifically, the recharging unit engages at least two of the BCM contacts 76 that communicate with the power generating unit 18 when the tool unit 12 is engaged with the BCM 14.

A charger, not illustrated and not part of this invention, is used to charge cells 38 internal to the BCM 14. Chargers that can be used to charge the cells are versions of the charges disclosed in Applicant's Assignee's U.S. Pat. No. 6,018,227 and its US Pat. Pub. No. US 2007/0090788 each of which is incorporated herein by reference. To charge the BCM of this invention, the BCM is fitted to a module attached to the charger. The module contains contacts similar to those integral with the tool unit 14. The BCM contacts 76 and 77 connect to the charger module contacts.

As described above, tool unit controller 40 controls the sourcing of energization signals to the tool unit power generating unit 18 based on input from switch state sensor 68. The tool unit controller of FIG. 16 includes a switch circuit 78 that selectively connects cells 38 to the BCM contacts 76. In the depicted version of the invention, this switch circuit is an H-bridge. The H-bridge consists of three pairs of series connected n-channel MOSFETs 80. The drains of the upper MOSFET of each pair of MOSFETs receive the positive voltage from the cells 38. The sources of bottom MOSFET 80 of each pair of MOSFETs is tied to ground. Each contact 76 is connected to the junction of a separate one of the pairs of series connected MOSFETs. It should further be understood that the body diodes of MOSFETs 80 are each forward biased from the ground line to the high voltage bus.

Tool unit controller further includes two n-channel MOSFETs 88 and 90 that are series connected together. MOSFETs 88 and 90 are located between the cathode of the series connected cells 38 and the high voltage bus connected to the drains of top located MOSFETs 80. The drains of MOSFETs 88 are 90 are tied together. MOSFET 88 is thus arranged so that the body diode of MOSFET 88 is forward biased from the cathode of cells 38 to the high voltage bus. MOSFET 90 is arranged so that the body diode of MOSFET 90 is reverse biased from the cathode of the cells 38 to the high voltage line. MOSFETs 88 and 90 are both gated by signals asserted from controller 44.

Controller 44 output control signals to the gates of MOSFETs 80. Controller 44 is able to output the signals to the MOSFETs so that energization signals are able to sourced to and sunk (returned) from the tool power generating unit over the tool unit contacts 74 and the BCM contacts 76. As described above some tool units of this invention include motors as their power generating units 18. Controller 44 is able to causes the sources of energization signals to a three phase motor.

As also seen in FIG. 16, the signals output from switch state sensor 68 and tool state sensors 69 are applied to controller 44. As discussed controller 44 employs these signals as input signals to regulate the outputting of energization signals by the BCM 14 to the tool unit 14. For example, when the tool unit power generating unit 18 is a motor, the signal from sensor 68 is the sensor signal representative of both the use desired on/off state of the motor as well as the user desired speed. The signals from sensors 69 are the signals representative of the rotational position of the rotor internal to the motor. Based on these signals the tool unit controller 44 gates the MOSFETs 80 so as to cause sequencing of the application of commutation currents to the windings as well as the appropriate pulsing or this current.

During times when the BCM 14 is employed to source power to the tool unit 12, controller 44 turns MOSFET 90 on. Owing to the body diode of MOSFET 88 being forward biased, there is typically no requirement to also turn on MOSFET 88.

When the BCM 14 is attached to the charger current can be sourced through one of the contacts 76. A second contact 76 serves as the connection through which a ground connection, a return connection, is established between the components internal to the BCM, including the cells 38, and the charger. Current is therefore sourced through the MOSFET 80 labeled Q1. In the illustrated version of the invention MOSFET 80 labeled Q8 functions as the MOSFET through which the ground a ground connection is made. Since the body diodes of MOSFETs 80 are forward biased, there is now need to, when attaching the BCM to the charger, turn on the MOSFETs 80.

Alternatively, in such an embodiment, a charge contact may pass through a ground contact (identified with a dashed line in FIG. 16 labeled "Current path (if additional ground connection is used)"). In this case, the ground contact serves as a reference voltage connection for both the charging circuit 82 and a communication circuit. It is to be appreciated that the drive circuit 78 may be included as part of the charging circuit 82.

In other words, at least one of the three BCM contacts 76 serves a dual purpose of 1) connecting the charging circuit 82 to the recharging unit when the recharging unit is coupled to the BCM 14 and 2) connecting the drive circuit 78 to the tool unit 12 when the tool unit 12 is coupled to the BCM 14. Said differently, at least one of the BCM contacts 76 that connects to a tool unit contact 74 during operation of the tool unit 12 also connects to the recharging unit during recharging. Since at least one of the BCM contacts 76 serves two purposes, the overall number of BCM contacts 76 is held to a minimum. This arrangement advantageously reduces cost, increases reliability, and decreases the area required to support the BCM contacts 76.

Tool unit controller 40 is configured to protect the cells 38 when the BCM 14 is being charged. recharging unit is engaged with the BCM 14. As mentioned above, the controller 44 is operatively coupled to the rechargeable cell 38. Controller 44 monitors voltages of the cell 38 to determine their charge state, for overcharge or discharge conditions (connections and components not shown). During charging, assuming the cells are in a state in which they can be charged, controller 44 turns on MOSFET 86 so the charging current can be sourced to the cells 38. Tool unit controller 40 include overcharge circuit 84 and/or a discharge circuit 86 both shown as block units.

When the BCM 14 is coupled to the charger, overcharge circuit 84 by monitoring the voltage present on the high voltage bus, monitors the voltage of the rechargeable cell 38 for overcharge conditions. The overcharge circuit and controller collectively, by turning on and off MOSFET 88 prevent excess current from being applied to cells 38

When the tool unit 12 is coupled to the BCM 14, the discharge circuit 86 is configured to monitor voltage of the rechargeable cell 38 for discharge conditions and regulate/toggle the electrical current passing through the rechargeable cell 38 to the extent necessary to enable the flow of current out of the rechargeable cell 38 to the system. Upon detection of voltage indicative of a discharge condition, the controller 44 may communicate with the discharge circuit 86. The controller may be configured to vary electrical current to the FET 90 of the discharging circuit 86. In turn, MOSFET 90 regulates the electrical current through the rechargeable cell 38 to allow for the discharge condition.

Tool unit controller 40 is further configured to detect fault conditions with respect to the rechargeable cell 38 when the recharging unit is engaged with the BCM 14. Advantageously, detection of fault conditions is possible while the BCM 14 is coupled to the recharging unit because the tool unit controller 40 and the rechargeable cell 38 are disposed within the BCM 14. The tool unit controller 40 may detect faults in the drive circuit 78, the charging circuit 82, the overcharge circuit 84, the discharge circuit 86, the controller 44, circuitry of the power generating unit 18, or any sensors. Accordingly, detection of fault conditions during charging is more efficient, convenient, and safe than detection of faults just before or during surgery.

II. Second Embodiment

A. Overview

Figure 17:
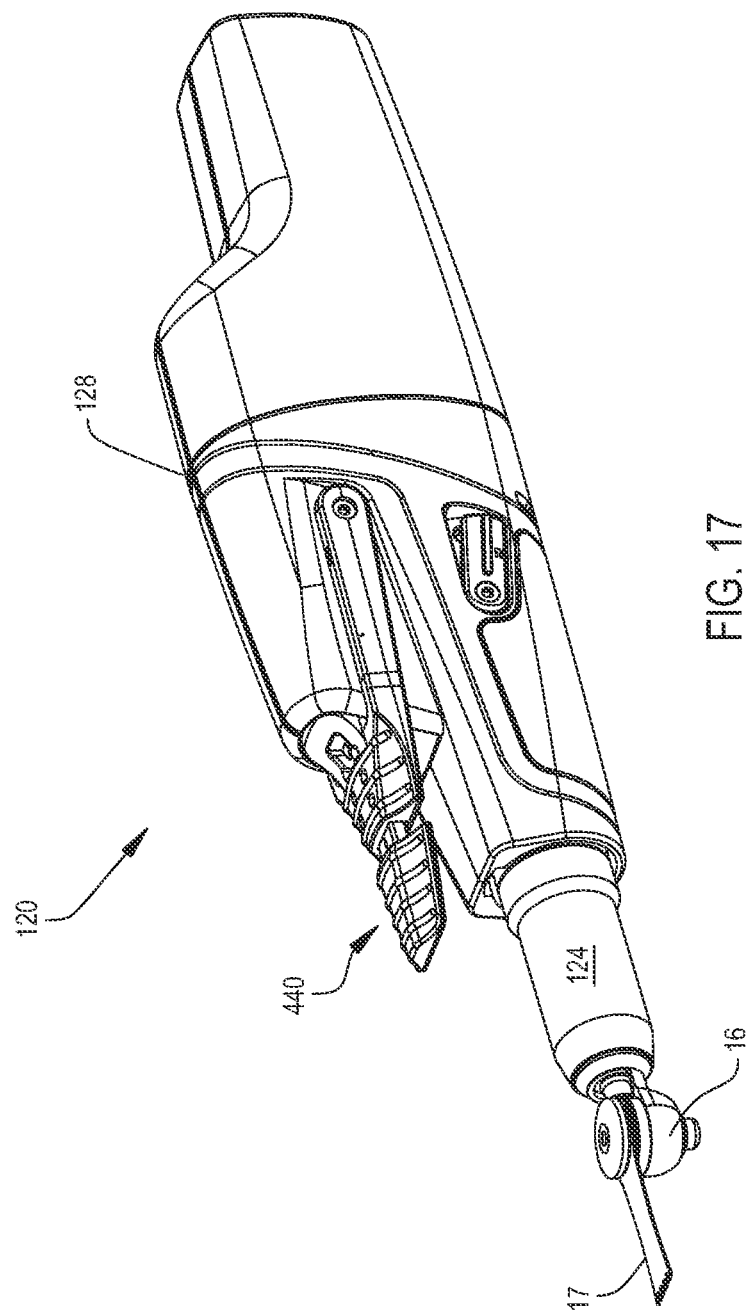
FIG. 17 is a perspective view of an alternative surgical tool assembly of this invention.
Figure 18:
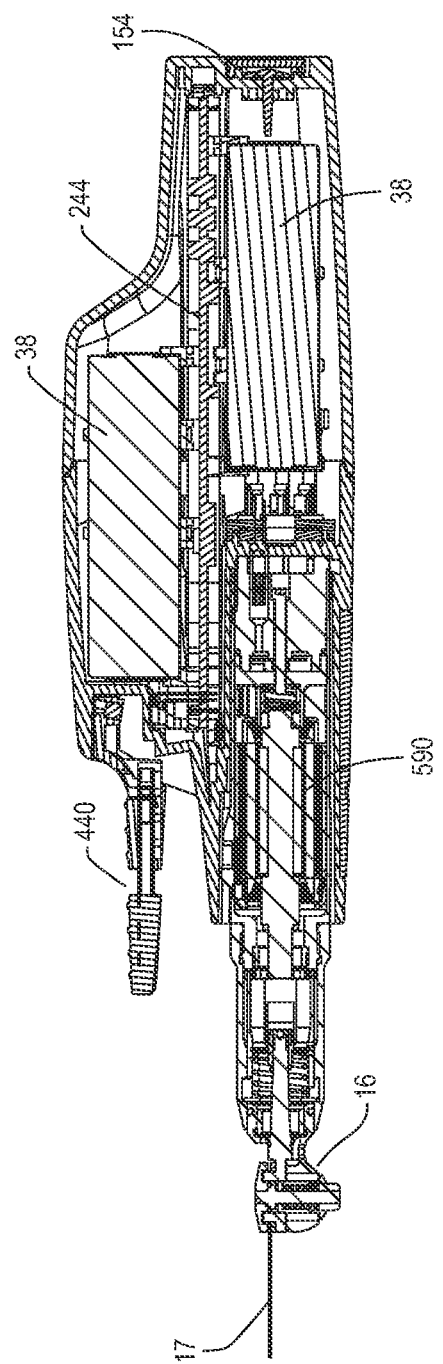
FIG. 18 is a cross sectional view of the powered surgical tool assembly of FIG. 17.
Figure 45:
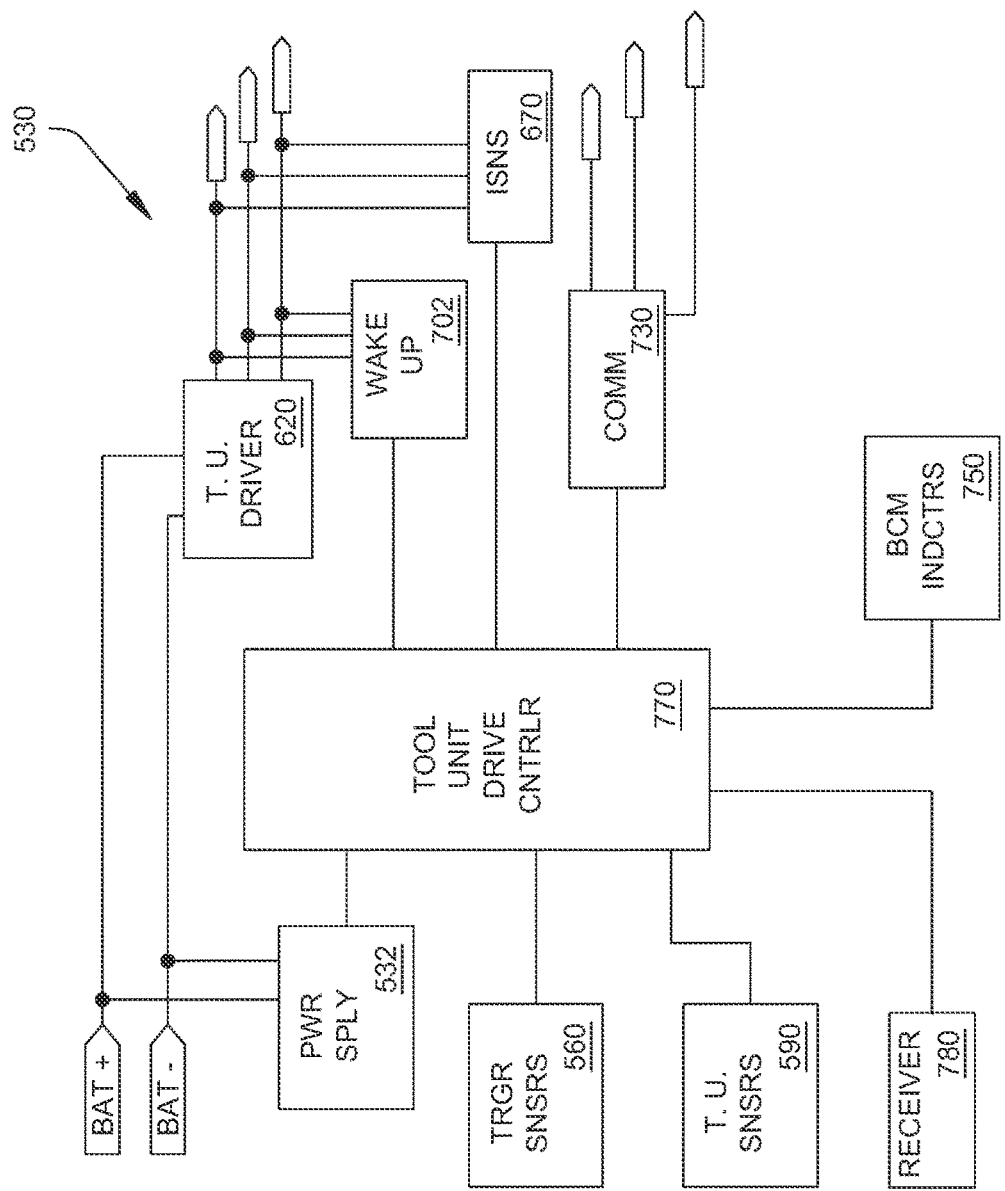
FIG. 45 is a block diagram of the major circuits forming the tool unit controller internal to the battery and control module.

An alternative powered surgical tool assembly 120 of this invention is now generally described by reference to FIGS. 17-19. Powered surgical tool assembly 120 includes a tool unit 124 that is removably attached to a battery and control module 128. The illustrated tool unit 124 includes a motor 950 as a power generating unit. The particular tool unit is designed to oscillate a sagittal saw blade 17. Internal to BCM 128 are two rechargeable cells 38. Cells 38 provide the power for energizing the tool unit motor 950. Also internal to the tool unit 128 is a tool unit controller 530 (FIG. 45). The tool unit controller 530 regulates the application of energization signals from cells 38 to the tool unit motor 950. A switch 440 is moveably mounted to the BCM 128. Tool unit controller 530 includes a sensor that monitors the manual actuation of switch 440. In part, in response to the actuation of the switch 440, the tool unit controller controls the application of energization signals to the tool unit 124. The tool unit controller 530 is further capable of monitoring the operating state of the power generating unit internal to tool unit 124. Tool unit controller 530 further controls the sourcing of energization signals based on the sensed operating state of the power generating unit.

B. Battery and Control Module

The BCM 128 includes a proximal shell 132 and a distal shell 162. Shells 132 and 162 are sealed together to form the housing or body of the BCM 128. Shells 132 and 162 are formed from a plastic such as polyphenylsulfone or polyetheretherketone or other material able to withstand the rigors of autoclave sterilization.

Further, the material forming the BCM housing should, at least adjacent the below described sensor 566, is a material through which the signal monitored by the sensor 566 can pass without being distorted or attenuated to a level that appreciably affects the ability of the sensor 566 to detect the characteristics of the signal. Similarly, at least the material forming the BCM housing adjacent the below described sensors 594 is a material through which the type of signal monitored by these sensors 594 can pass without being distorted or attenuated to a level that appreciably affects the ability of the sensors 594 to detect the energy level. Here "adversely affects" is understood to mean a distortion or attenuation of the signal that result in the sensors not being able to output signals that, with the required degree of accuracy for this invention, that reflect changes in the characteristics of the signals.

Figure 20:
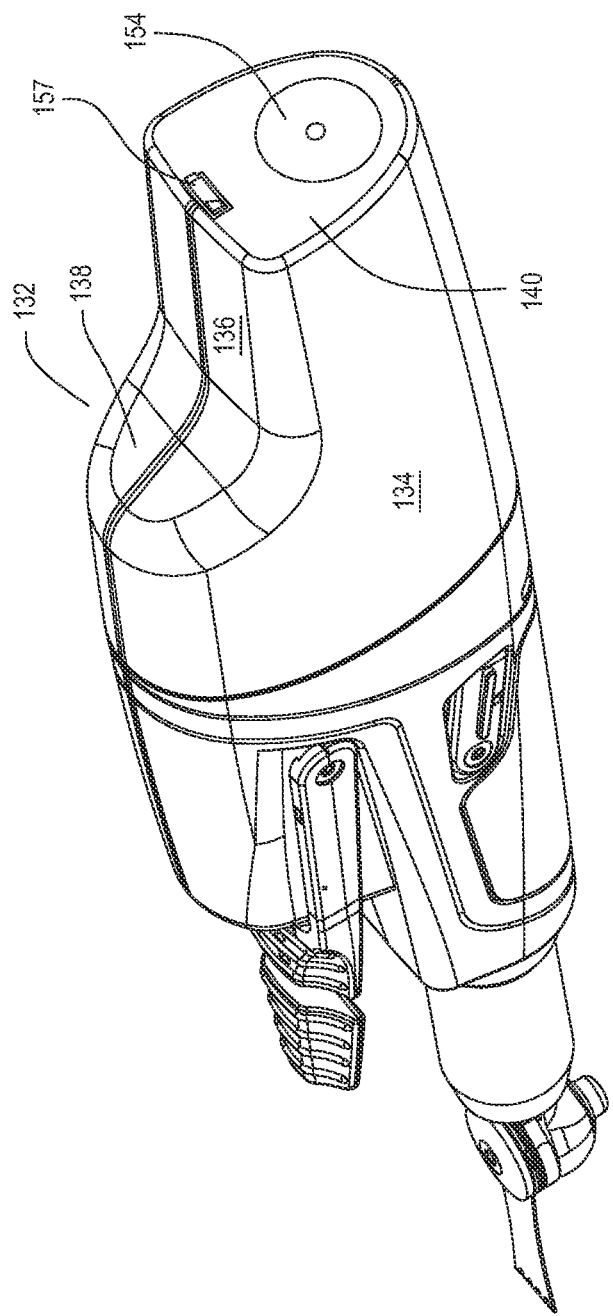
FIG. 20 is a perspective view of the alternative surgical tool assembly of FIG. 17 showing the proximal end of the assembly.
Figure 22:
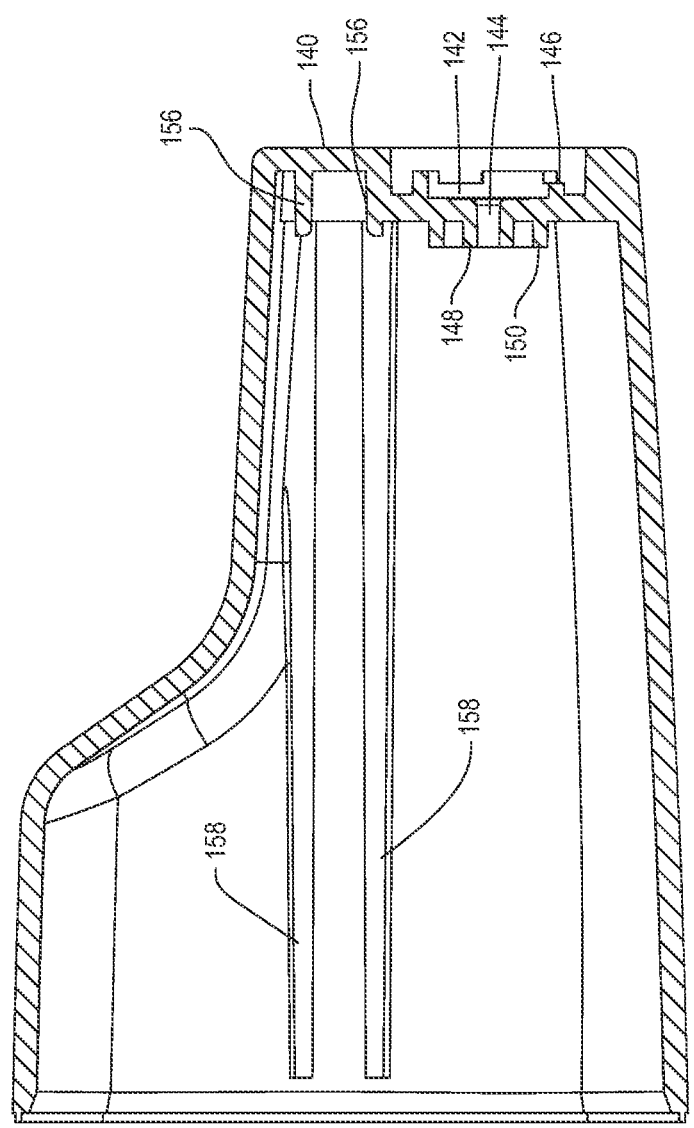
FIG. 22 is a cross sectional view of the proximal shell of the battery and control module of FIG. 19.

From FIGS. 20 and 22 it can be seen that the proximal shell 132 is a single piece unit. Shell 132 is shaped to have a bottom portion, not, identified that curves outwardly and upwardly into two opposed curved side panels 134. At the proximal end of the shell the side panels 134 curve into a top panel 136. Distal to the top panel 136 the side panels 134 curve inwardly so come together at the top of the shell. A transition panel 138 curves upwardly from the distal end of the top panel 136 to close off the shell at the location where the side panels 134 project above the top panel 136. An end plate 140 forms the proximal end of proximal shell 132.

A generally circularly shaped step 142 is integral with and located distally forward inwardly from end plate 140. Step 142 thus defines a recess in the end plate 140. The step 142 is formed to have an opening 144 that extends proximally-to-distally through step 142. A set of ribs 146 project proximally outwardly from the proximally directed face of step 142. Ribs 142 are radially spaced from opening 144. Inside the shell 132 two circular ribs 148 and 150 extend distally forward from the distally directed face of step 142. Rib 148 extends forward around the volume immediately forward of opening 144. Rib 150 is spaced radially outwardly from so as to be spaced radially away from rib 148. Step 142, opening 144 and ribs 146, 138 and 150 are provided to facilitate the mounting of a pressure relief valve 154, seen in FIGS. 18 and 20, to shell end plate 140. Pressure relief valve 154 is provided to facilitate the venting of the void space internal to the BCM 128 during sterilization. The structure of the pressure relief valve 154 is not part of the present invention.

Two parallel ribs 156 extend distally forward from the inner surface of end plate 140. Ribs 156 extend laterally across the end plate 156. The ribs 156 are spaced apart. Two parallel ribs 158 extend inwardly from the opposed inner surfaces of shell side panels 134. Each rib 158 is located within the proximal shell 132 so as to be at a height that approximately corresponds to the height of a separate one of the ribs 156. Each rib 158 extends longitudinally distally forward from the associated rib 156. Each rib 158 terminates a short distance, less than 1 cm, from the open proximal end of the shell.

The distal shell 162 has a main portion 164 that, in cross section planes perpendicular to the proximal-to-distal longitudinal axis through the shell is elliptical in shape. The proximal end of shell main portion 164 is open and shaped to mate with the open distal end of proximal shell 132. A lip 163 that is slightly smaller in shape then the main portion, extends proximally rearward from the main portion. Lip 163 is stepped inwardly from the outer perimeter of the main portion. When the BCM 128 is assembled, lip 163 seats against the inner surface of the distal end of proximal shell 132. Not identified is the tapered outer surface of lip 163.

A nacelle 166 extends forward from the shell main portion 164. The distal shell 162 is formed so that the nacelle 166 extends distally forward from the lower section of shell main portion 164.

Figure 23:
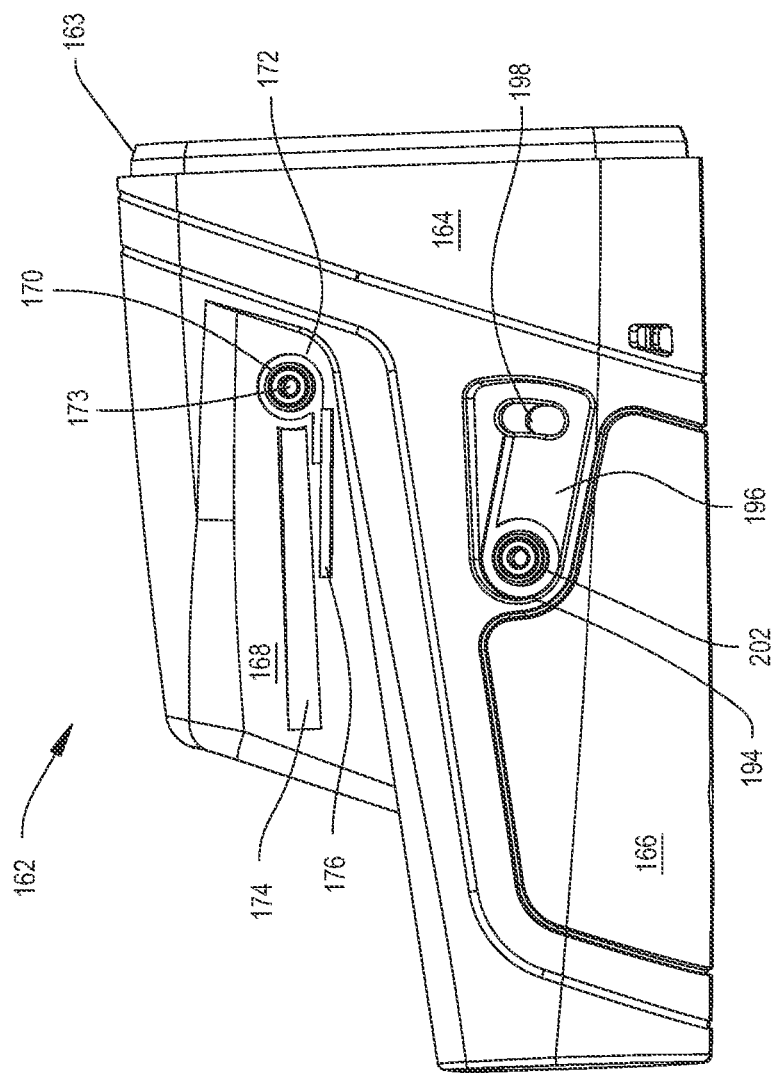
FIG. 23 is side plan view of the distal shell of the battery and control module of FIG. 19.
Figure 24:
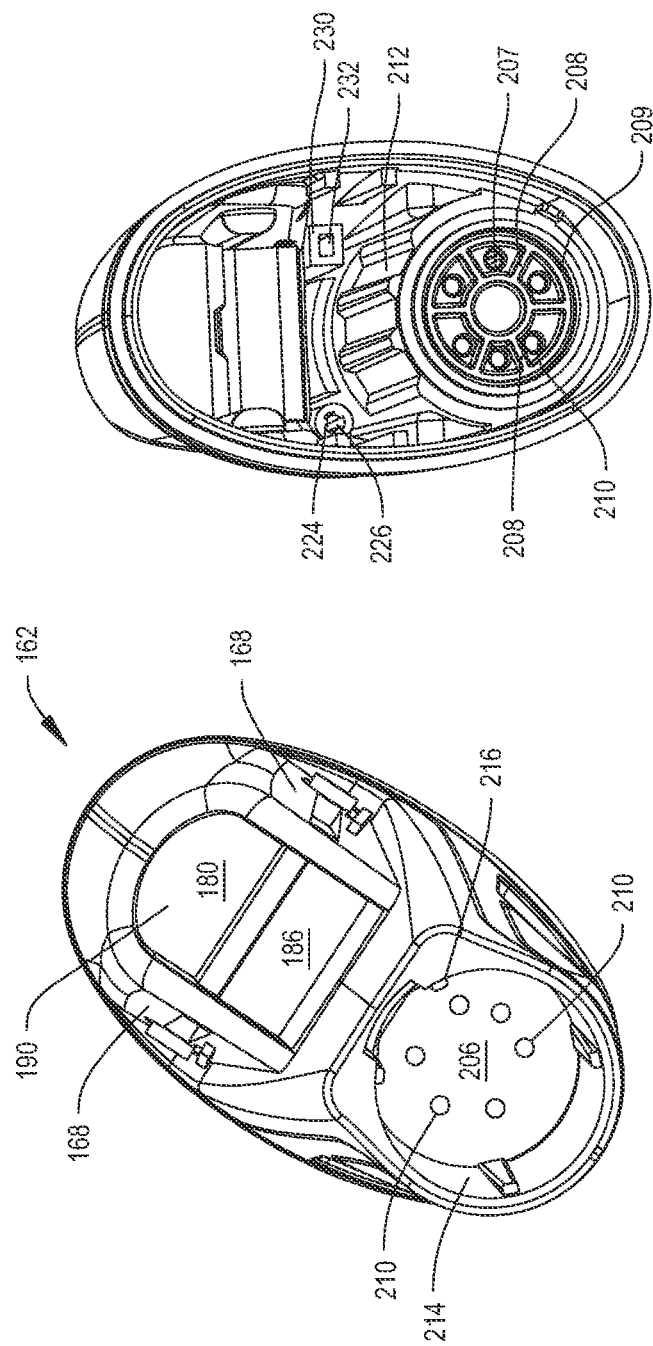
FIG. 24 is a perspective view looking into the distal end of the distal shell of the battery and control module of FIG. 23.

Distal shell 162 is further formed so that immediately proximal to and above nacelle 166 the shell main section has two side opposed side panels 168, identified in FIG. 24. Side panels 168 are tapered in that extending from the distal end of each panel the panel angles away from the vertical plane that intersects the longitudinal axis of the distal shell 162. Forward of the proximal end of each side panel 168, the panel is form to define a recessed surface 170. From FIG. 23 it can be seen that each recessed surface has a circular section A boss 172 extends outwardly from each recessed surface 170. A closed end bore 173 extends inwardly from the outer surface of the boss 172. Annular ribs (not identified) project outwardly from the outer surface of the boss.

Each side panel 168 is further shaped so that there is an elongated generally rectangularly shaped notch 174 in the panel. Notches 174 extend longitudinally along the distal shell 162. Each notch 174 starts at a location a slight distance forward of the adjacent recessed surface 170. Notches 174 are present for manufacturing reasons and are otherwise not relevant to this invention. The distal shell 162 is further formed so that a rectangular bar 176 extends outwardly from each side panel 168. Each bar 176 is located below the adjacent notch 176. Each bar is also located below a short linear extension of the recessed surface 170 formed in the side panel 168.

Figure 25:
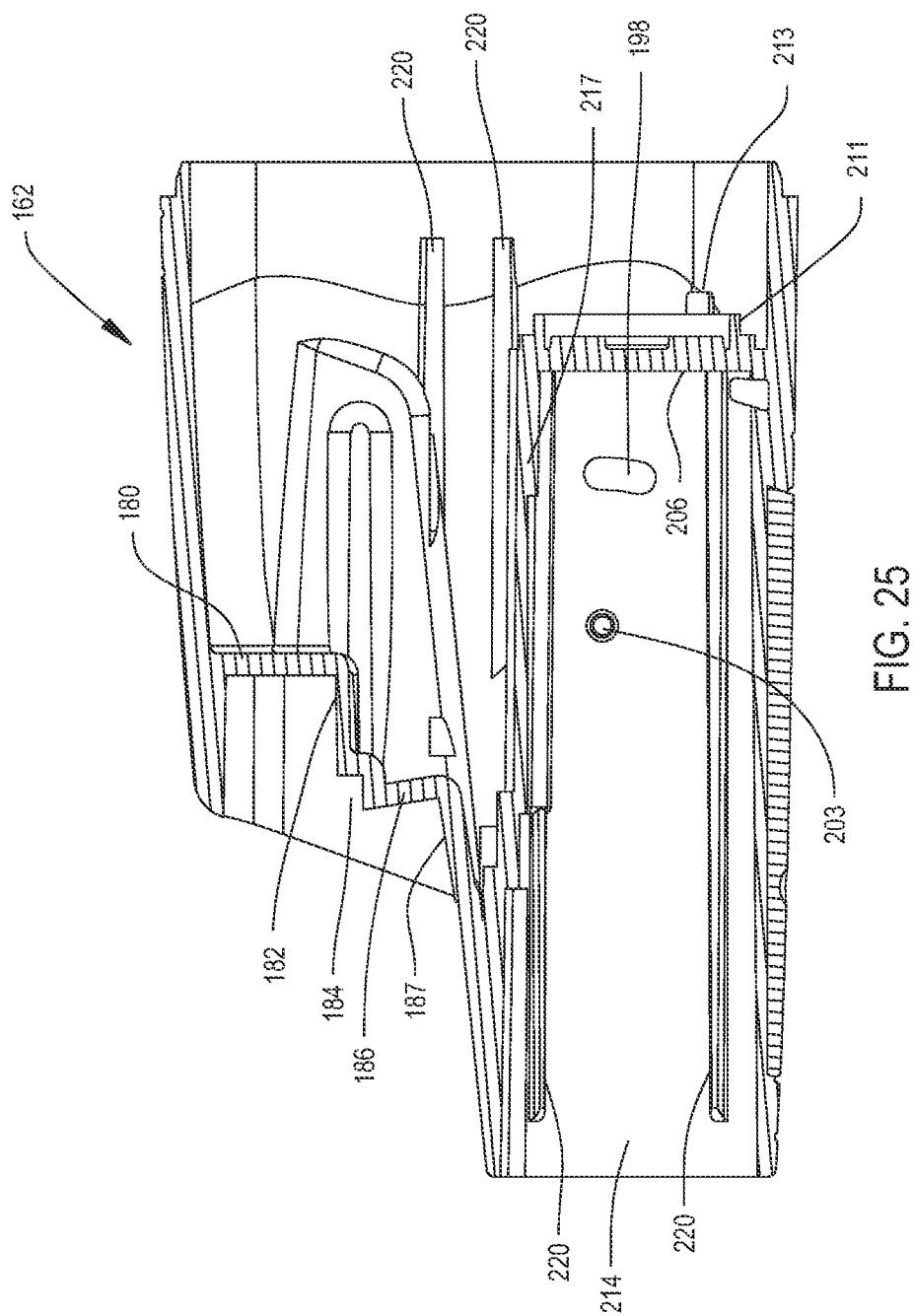
FIG. 25 is a cross sectional view of the distal shell of the battery and control module of FIG. 23.

A multi-section web seen in FIG. 25 extends between the opposed inner surfaces of the spaced apart side panels 168. This web includes a top panel 180 that extends downwardly from the curved upper portion of the shell from which the side panels 168 extend. The web includes a step 182 that extends distally forward from the bottom of the upper panel 180. A bottom panel 186 extends forward from the distal end of step 182. In the depicted version of the invention, distal shell 162 is formed to define a notch 184 at the location from which the bottom panel extends downwardly from step 182. A floor panel 187 extends forward from the base of the bottom panel. Floor panel 187 tapers distally and downwardly forward into a section of the shell 162 that defines the top of nacelle 166. The proximally facing surfaces of panels 180, 186 and 187 and of step 182 partially define the proximal end of the void space internal to the BCM 128. The inner surfaces of the side panels 168, the distally facing surfaces of panels 180, 186 and 187 and the adjacent surface of step 182 define a cavity 190 within the distal shell 162. Cavity 190 extends proximally from the forward edges of the shell side panels 168. Notch 184 is located within cavity 190.

Distal shell 162 is further formed so that below side panels 168 that are opposed recessed surfaces 194 and 196 in the side portions of the shell, one surface 194 and 196 each seen in FIG. 23. Each recessed surface 194 has a longitudinal axis that is approximately parallel with the longitudinal axis through the shell 162. Each recessed surface 194 is further formed so that the proximal portion of the surface has a larger top-to-bottom width that the forward located distal portion. The recessed surfaces 196 are inwardly recessed relative to the companion recessed surfaces 194. Each recessed surface 196 has a circular portion, not identified, that extends inwardly from associated recessed surface 194 at the distal end of the recessed surface 194. Each recessed surface 196 has a linear extension, not identified, that extends forward from the circular portion. A through opening 198 extends inwardly from the proximal end of each recessed surface 194. Each opening 198 is generally in the shape of an oval that has a curved longitudinal axis. A boss 202 extends outwardly from the center of the circular portion of each recessed surface 198. Not identified are the radially spaced apart ribs that project outwardly from the exposed face of each boss 202. A bore 203 extends through boss Internal to and integral with distal shell 162 is a disc 206 seen best in FIGS. 24-26. Disc 206 extends upwardly from the inner surfaces of the shell at the bottom of the shell. Disc 206 is formed so as to have ribs that extend rearwardly from the proximally directed face of the web. There are two circular ribs, ribs 207 and 209. Ribs 207 and 209 are concentric and centered on the center axis of disc 206. There are six radial ribs, ribs 208. Each rib 208 extends between the outer surface of rib 207 and the inner surface of rib 209. Each rib 208 is diametrically opposed to a second rib 208 relative to the center of disc 202.

Disc 206 is also formed to have a number of through holes 210 that extend proximally to distally through the disc. Each through hole 210 is located in an arcuate section of the disc between ribs 207 and 209 and between two adjacent ribs 208. The disc 206 is also shaped to have a ring 211, identified in FIG. 25, that extends proximally rearward from the proximal face of the disc. Ring 211 extends circumferentially around the disc so as to be spaced a slight distance inward of the outer perimeter of the disc. Distal shell 162 is further formed so that ring 211 extends proximally rearward beyond ribs 207 and 209. A tab 213 projects proximally rearward from a section of the ring 211

A web 212 extends forward from the outer perimeter of disc 206 that is spaced inwardly of side panels of the shell 162. Web 212 is arcuate in cross sectional shape in the plane perpendicular to longitudinal axis through the shell. The web extends to where the outer structural components of the shell form nacelle 166. The distally directed face of disc 206, the inner face of web 212 and the inner surfaces of the outer structural panels of the nacelle 166 define a bore 214. Bore 214 is open at the front of nacelle 166 and extends through nacelle into the main portion of the shell. Disc 206 and web 212 separate bore 214 from the main void space internal to the BCM 128. Distal shell 162 is further formed so that ribs 216 project inwardly into bore 214 from the inner surfaces of the shell structural panels and of web 212. Openings 198 and bores 204 extend into bore 214. Disc through holes 210 also open into bore 214.

The distal shell 162 is further formed so that the portion of the shell that defines the distal section of bore 214 defines a groove 216 that extends outwardly from the outer perimeter of the bore. Groove 216 extends outwardly from the upper portion of the bore. Nacelle 166 is further formed so that four raised ribs 215, only three seen extend inwardly from the surfaces of the nacelle that define bore 214. The nacelle is further formed so that a single rib 217 seen in cross section in FIG. 25 extends downwardly into bore 214. Rib 217 extends forward a short distance, typically less than 3 cm from the proximal end of bore 214.

Two ribs 220, identified in FIG. 25, extend inwardly from the opposed inner surfaces of the sides of the distal shell.

The ribs 220 are positioned so that when shells 132 and 162 are fitted together, each rib 220 is aligned with a separate one of the proximal shell ribs 158.

The distal shell 162 is further formed so that there are two posts 224 and 230 are located inside the void within the shell. Posts 224 and 230 have proximal ends that are located forward of where ribs 220 merge into sides of the main body of the distal shell 162. Post 224 is circular in cross section and has a generally circular closed end bore 226 that extends distally forward from the proximal face of the post. Post 230 is rectangular in cross section. The post 230 is formed with a closed end bore 232 that is rectangular in cross section and that extends inwardly from the proximal face of the post. In the cross section plane perpendicular to the longitudinal axis along post 230, the major axes of both post 230 and bore 232 are both located on lines that extend side-to-side across the distal shell 162.

Figure 19:
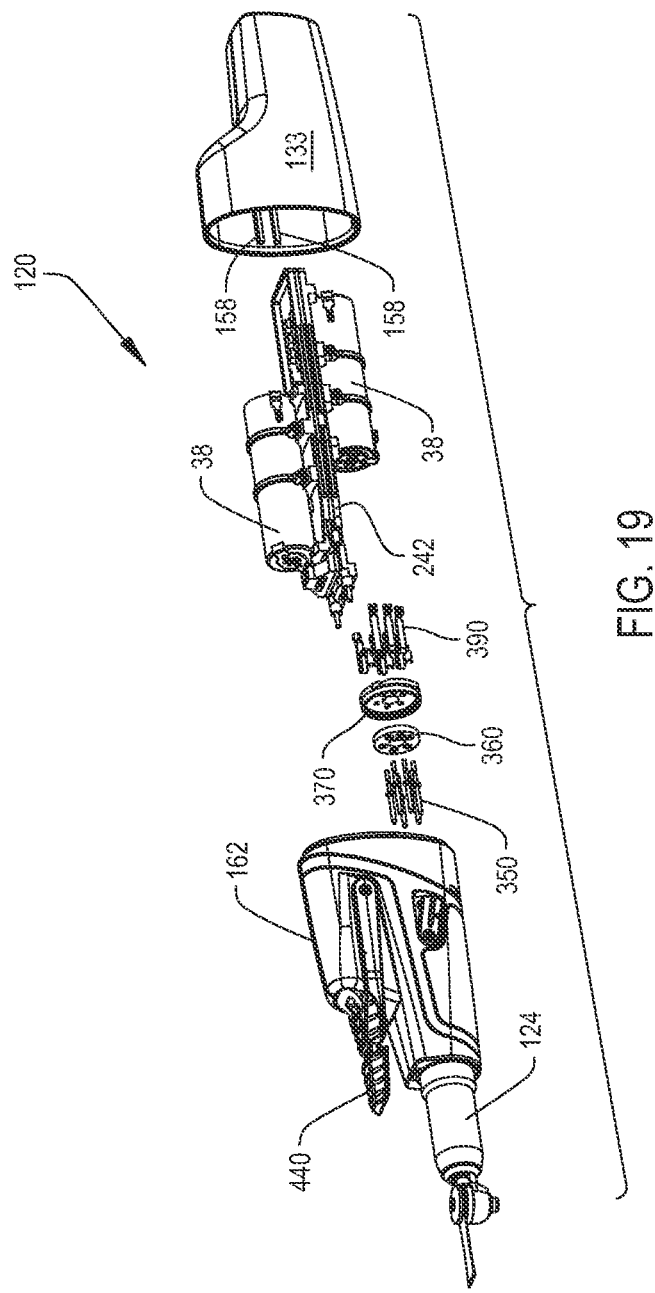
FIG. 19 is an exploded view of the alternative surgical tool assembly of FIG. 17.
Figure 21:
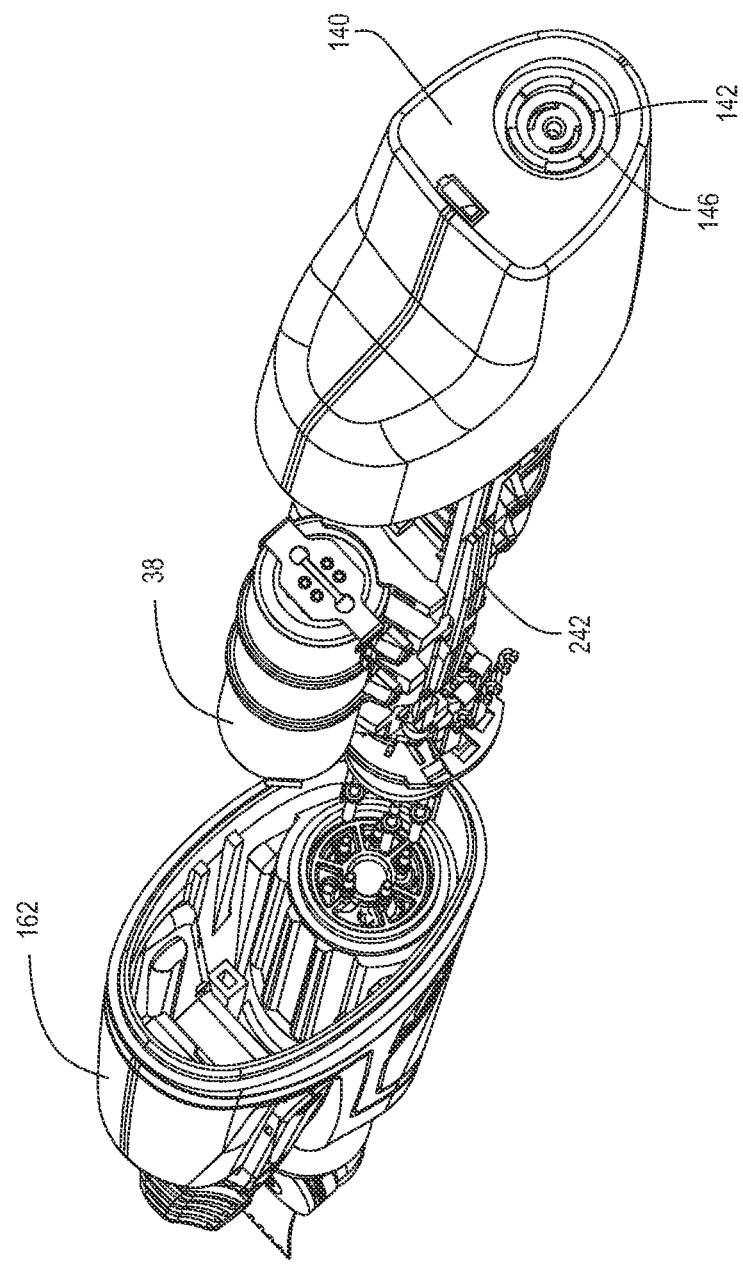
FIG. 21 is a perspective exploded view of the powered surgical tool assembly looking into the distal shell of the battery and control module.

From FIGS. 19 and 21 it can be seen that internal to the BCM housing is a chassis 242. Mounted to chasses 242 are the cells 38. Also mounted to the chassis 242 is a circuit board 244. Circuit board 244 contains the tool unit controller 530 that selectively applies energization signals from the cells 38 to the tool unit power generating unit 950. Sensors 566 and 594 are also mounted to the chassis 242. Sensor 566 is the sensor that monitors the actuation of switch 440. Sensors 594 monitor an operating state characteristic of the tool unit power generating unit 950. The signals output by the sensors 566 and 594 are applied to tool unit controller 530. Based on the states of these signals, tool unit controller 530 selectively sources energization signals, energization currents, to the tool unit 950.

Figure 27:
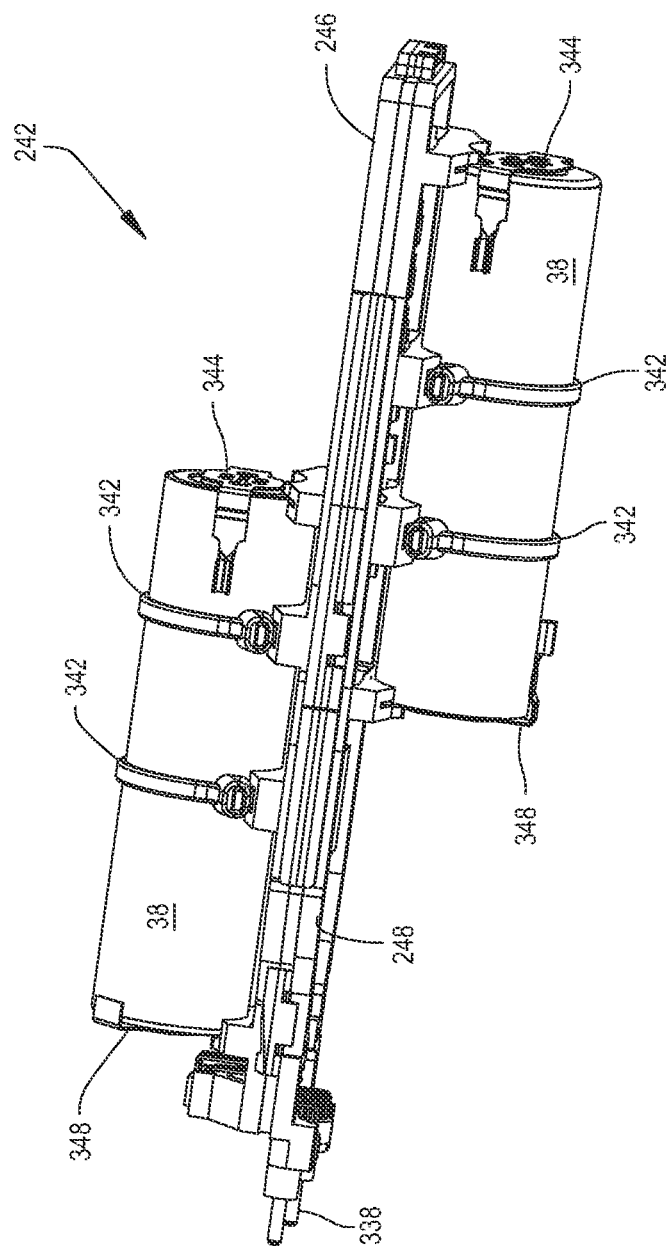
FIG. 27 is a perspective view of the chassis internal to the battery and control module and a number of the components attached to the chassis.
Figure 28:
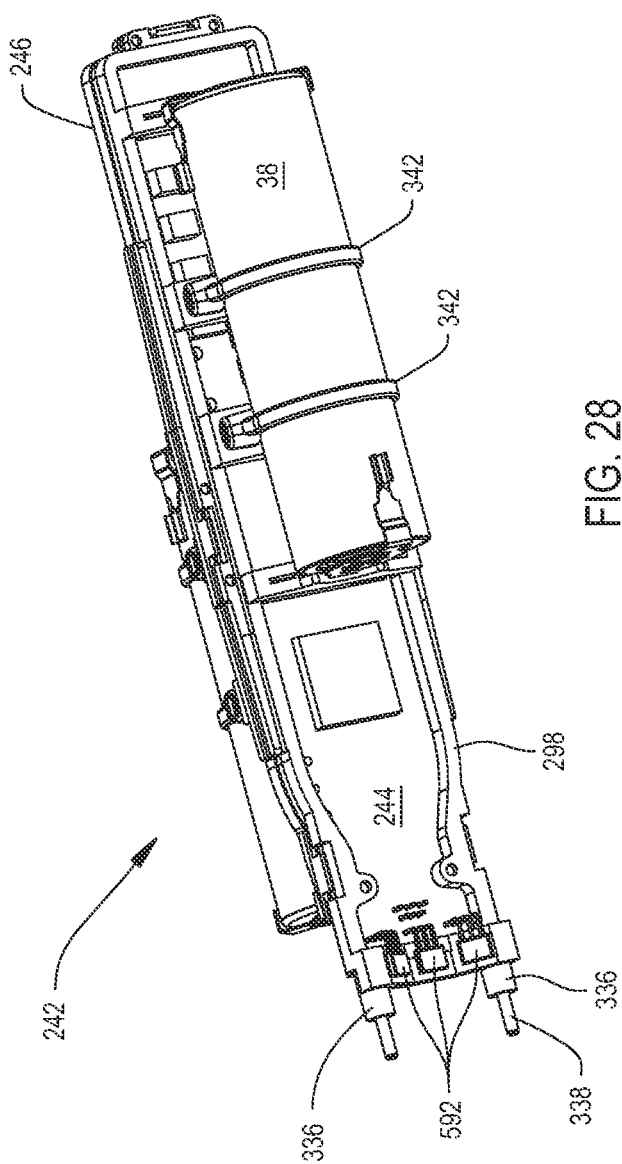
FIG. 28 is a perspective of the bottom directed portion of the chassis and attached components of FIG. 27.

As seen in FIGS. 27 and 28, the chassis 242 include an upper frame 246 and a lower frame 296. Frames 246 and 296 are formed from the same materials from which shells 132 and 162 are formed. The upper frame 246, now described by reference to FIGS. 29 and 30 has a proximal end beam 247. An approximately U-shaped toe 248 extends proximally from the proximally directed face of beam 245. A flexible snap tab 250 extends downwardly from toe 248. Two side beams 252 extend distally forward from proximal end beam 247. Along approximately four-fifths the length of frame 244, the side beams 252 are parallel. At a location approximately four fifths the length of the frame 246 forward of proximal beam 245, the side beams 252 taper slightly inwardly toward each other. The most distal portions of the side beams, approximately the most distal 0.5 cm of the beams 252 are parallel, A bar 256 extends downwardly from the undersurface of each beam 252. Each bar 256 is generally elongated in shape. The bars 256 extend downwardly from the parallel portions of the side beams 252. The upper frame 246 is further formed so that each bar 256 does not extend over the whole of the undersurface of the beam 252 with which the bar is integral. Instead, upper frame 244 is formed so that each bar 256 is stepped slightly outward of the associated side beam 252. Upper frame 244 is further formed so a snap tab 258 extends downwardly from each bar 256. Each bar 256 is further formed with an elongated notch 259 that extends inwardly from the downwardly directed surface of the bar. Notches 259 are located proximal to snap tabs 258.

Two addition bars, bars 260 also extend downwardly from side beams 252. Bars 260 are spaced distally forward of and are smaller in length then bars 256. The upper frame 244 is formed so that each bar 260 projects downwardly from and is stepped outwardly the inwardly tapered portion of the side beam 252 with which the bar is integral. Each bar 260 also extends a short distance, approximately 0.3 cm, along the adjacent distal portion of the side beam 252. A snap tab 262 projects downwardly from each bar 260.

The upper frame 246 is further formed to have a number of pins 264. Two pins 264 extend downwardly below toe 248. Two pins 264 extend below each bar 256. The pins 264 integral with each bar 256 are located on the opposed sides of the snap tab 258 integral with the bar 256. Two pins 264 also extend downwardly from the below described web 284.

Five webs 268, 274, 276, 284 and 288 extend across the frame side beams 252. Each web has first and second side surfaces, (not identified). The first side surface rises up from the side of the beam 252. The second side surface, as the surface extends upwardly from the beam 282 tapers inwardly. Web 268 is the proximalmost of the webs. The top of web 268 has two inwardly curved faces (not identified) that extend across the upper frame 246. The more distal of the two curved faces is recessed inwardly relative to the proximal face. Thus the faces define a notch 270 in the web 268. Web 268 is further formed to define two slots 272. one identified that extends inwardly from the top of the web. The slot 272 separates the two curved top faces of the web.

Webs 274 and 276 are essentially identical in shape. The webs 274 and 276 extend between the main parallel sections of side beams 252. Each web 274 and 276 has an inwardly curved top face (not identified.) Each web 274 and 276 is formed to have an opening 278 in the inwardly tapered side surfaces of the web. Web 284 extends between the distal parallel portions of side beams 252. The web 284 is formed to define a notch 286 that extends forward from the proximally directed face of the web. The notch-defining face top face of web 268, the top faces of webs 274 and 278 and the notch defining top face of web 284 have a common radius of curvature that is centered around a common axis.

Web 288 is the most distal of the webs formed on the upper frame 246. Web 288 extends between the side beams 252 immediately behind the distal ends of the beams. The upper frame 246 is formed so that web 288 is generally arcuate in shape. A fixed rectangularly shaped crown 290 extends upwardly from the top of web 288. Crown 290 is shaped to have a center notch 292.

Figure 31:
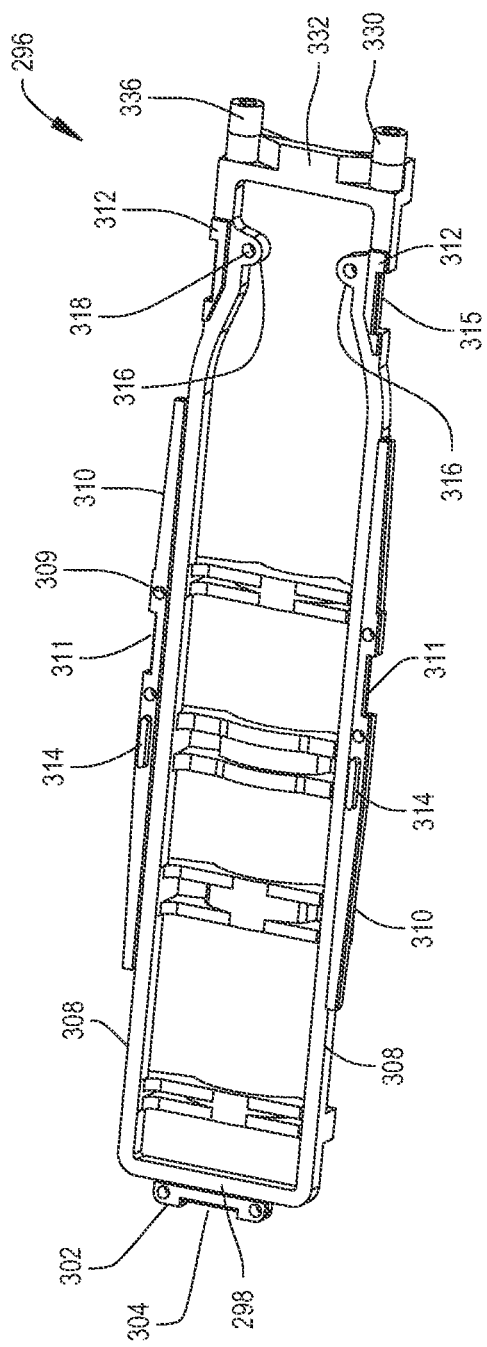
FIG. 31 is a perspective view of the upwardly directed portion of the lower frame of the chassis.
Figure 32:
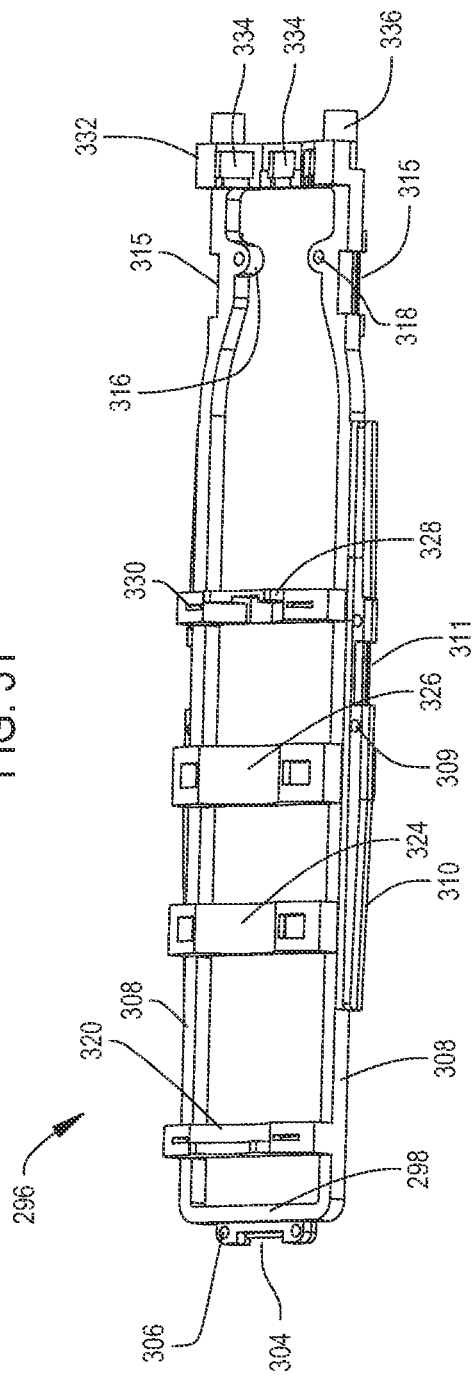
FIG. 32 is a perspective view of the downwardly directed portion of the chassis lower frame of FIG. 31.

The chassis lower frame 296 is now described by reference to FIGS. 31 and 32. The lower frame 296 includes a proximal end beam 298. A toe 302 projects rearwardly from the proximal end beam 298. In shape, toe 302 is generally identical to that of upper frame toe 248. Toe 302 is formed with a notch 304 shaped to receive the upper frame tab 250. The upper frame toe 302 is further formed to have two through holes 306 (one identified). Holes 306 are positioned and dimensioned to receive the pins 264 that project downwardly from the upper frame toe 302.

Two side beams 308 extend forward from the lower frame proximal beam 298. Chassis lower frame 298 is shaped so that when the chassis is assembled together the lower frame side beams 308 substantially underlie the upper frame side beams 252. Two pairs of bars, bars 310 and bars 312, extend upwardly from the top surfaces of side beams 308. Frames 246 and 296 are shaped so that when the frames are assembled together, each lower frame bar 310 is in registration with the overlying upper frame bar 256. Each bar 310 is formed with a notch 311 and two through holes 309. The notch 311 is shaped to receive the snap tab 258 of the complementary bar 256. Each hole 309 is dimensioned to receive one of the pins 264 that extends downwardly from the complementary bar 256. A tab 314 protrudes upwardly from the exposed face of each bar 310. When the chassis 242 is assembled, each tab 314 seats in the complementary notch 259 in the complementary bar 256.

Each bar 312 is positioned to be in registration with a complementary one of the upper frame bars 260. A notch 315 is formed in each bar 312. Notches 314 are shaped and positioned to receive the snap tab 262 integral with the overlying upper frame bar 260.

The lower frame side beams 308 are formed with inwardly directed protrusions 316. Each protrusion 316 is located adjacent the forward end of the bar 312 integral with the beam 308 in which the protrusion is formed. Each protrusion 316 is formed with a through hole 318. When chassis 242 is assembled, the pins 264 that project down from the overlying web 284.

Five webs 320, 324, 326, 328 and 332 extend across the downwardly directed faces of side beams 308. Web 320 has features that can be considered symmetric to those of upper frame web 268. Accordingly these features are not redescribed. It is noted that web 320 is located proximal to web 268. Webs 324 and 326 have features symmetric to those of webs 274 and 276. Webs 324 and 326 are located proximal to webs 274 and 276. Web 328 has a shape similar to that of lower frame web 284. The web 328 is formed with two slots 330 that project upwardly from the downwardly directed face of the web. The frames 246 and 296 are collectively shaped so that lower frame web 324 is located proximal to the upper frame web 284.

Frames 246 and 296 are further shaped so that the lower frame web 332 is located a short distance forward of upper frame web 288. Web 332 is generally arcuate in shape in that downwardly directed surface of the web has an upwardly curved surface. Lower frame 296 is further formed so that web 332 has three spaced apart notches 334, two notches identified. Web 332 us formed so that notches 334 are arranged in an arc. More particularly the arc around which the notches are formed is centered on the longitudinal axis through distal shell bore 214. Each notch 334 has a longitudinal axis, an axis parallel to the longitudinal axis through bore 214. Web 332 is shaped so the longitudinal axes of each two adjacent notches 334 are spaced 60° apart from each based on point along the longitudinal axis through bore 214 being the vertex from which the radial lines to each notch longitudinal extends.

Two posts 336 extend distal forward from the opposed sides of the distally directed face of web 332. A pin 338, one identified in FIG. 28. extends forward from each post 336.

As part of the process of manufacturing the BCM 128, circuit board 244 with the components mounted thereto, is sandwiched between the upper frame 246 and the lower frame 296. When the frames 246 and 296 are brought together, the upper frame bars 256 and 260 abut the lower frame bars 310 and 312. This defines a space between the beams of the frames 246 and 296 in which the perimeter portion of the circuit board is fit. Upper frame pins 264 seat in the lower frame holes 306. The lower frame tabs 314 seat in the upper frame notches 259. The seating of these components in these void spaces facilitates proper alignment of the frames 246 and 296. This components seating also prevents post assembly shifting of the frames. The frames 246 and 296 are held together by the snap fitting of the upper frame snap tabs 250, 258 and 262 in the lower frame notches 304, 311 and 315, respectively.

Once the circuit board 244 and frames 246 and 296 are assembled together, rechargeable cells 38 are mounted to the chassis. One cell 38 is seated on upper frame webs 268, 274, 276 and 284. The proximal end of the cell is seated in the notch 270 defined by web 268. Thus the step that defines the proximal end of the notch blocks proximal longitudinal movement of the cell 38. The distal end of the cell 38 is seated in the notch 286 defined by web 284. The seating of cell 38 in notch 286 blocks distal longitudinal movement of the shell. Tie strips 342 that extend around the cell 38 and through openings 278 in webs 274 and 276 hold the cell to the chassis. The second cell 38 is similarly held in position against the downwardly directed surfaces of lower frame webs 320, 324, 326 and 328.

A contact plate 344 is mounted to the proximal end of each cell. Tabs, not illustrated, integral with the contact plates 344 seat in the slots integral with webs 268 and 320. A contact plate 348 is mounted to the distal end of each cell 38. Tabs, not illustrated, integral with contact plates 348 seat in the slots integral with slots 330 of web 328. Contact plates 344 and 348, along with wires not shown, provide the conductive paths from the terminals of the cell to below discussed tool unit controller 530 on circuit board 244.

When the battery and control module 128 is assembled the distal portion of the chassis 242 is slid between ribs 220 internal to the distal shell 162. The components forming BCM 128 are shaped so that the chassis is compressed between the ribs 220. Chassis 242 is slide forward so that the left side chassis pin 338 seats bore 226 internal to shell post 224. Simultaneously the right side chassis pin 338 seats in bore 232 internal to shell post 230. More particularly the ribs 225 that extend into bore 226 hold the associated pin 338 in a specific position within the bore 226. Owing to the rectangular cross sectional shape of bore 232 and the relative dimension of post 230 and pin 338, the position of the pin within bore 232 is fixed only in the vertical axis. The position of pin in the horizontal plane, the plane in and out of FIG. 18, has some minor degree of variation. Thus, the components forming BCM 128 allow for some manufacturing tolerances while ensuring that the vertical position of the chassis 242 and components attached to the chassis have essentially fixed vertical position within the void space of the BCM housing.

When the proximal shell 132 is fitted over the open end of the distal shell 162, the proximal side portions of the chassis 242 is slightly compressed between the proximal shell ribs 158. The proximal end of the chassis 242 is compressed between ribs 156. Ribs 156, 158, 220 and pins 338 thus collectively hold the chassis 242 in a fixed position in the void space within battery and control module 128.

Figure 34:
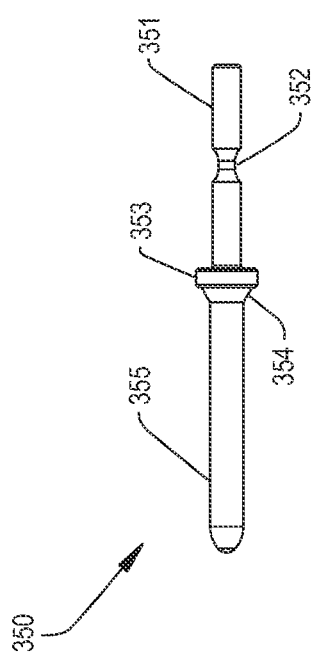
FIG. 34 is a plan view of one of the contact pins of the battery and control module.

Contact pins 350 provide the electrical connections pin the battery and control module 128 and the components to which the module is connected. From FIG. 34 it can be seen that a contact pin 350 is a single piece unit. The pin 350 is formed from an electrically conductive material such as brass. At the proximal end, the pin is shaped to have a cylindrical trunk 351. While the trunk is generally cylindrical, the pin is formed to define an annular groove 352 that extends circumferentially around the trunk 351. Groove 352 is located at position approximately midway along the length of the trunk 351. Contact pin 350 is further shaped to have a stopper that is located forward of the trunk 351 and that extends circumferentially around the trunk. The stopper has a proximal section 353 of constant diameter. Stopper proximal section 353 has a diameter greater than that of trunk 351. A stopper distal section 354 extends forward from the proximal section 353. The distal section is frusto-conical in shape. The diameter of the distal section 354 decreases the further the distal section is away from the proximal section 353. In the depicted version of the invention, the most proximal portion of the distal section has a diameter that is approximately 0.5 mm less than the diameter of the proximal section 353

Stopper distal section 354 merges into a cylindrically shaped pin head 355. In the illustrated version of the invention, pin head 355 has a diameter greater than that of trunk 351 and less than that of stopper proximal section 353. The most distal end of pin head is semi-spherical in shape.

Figure 33:
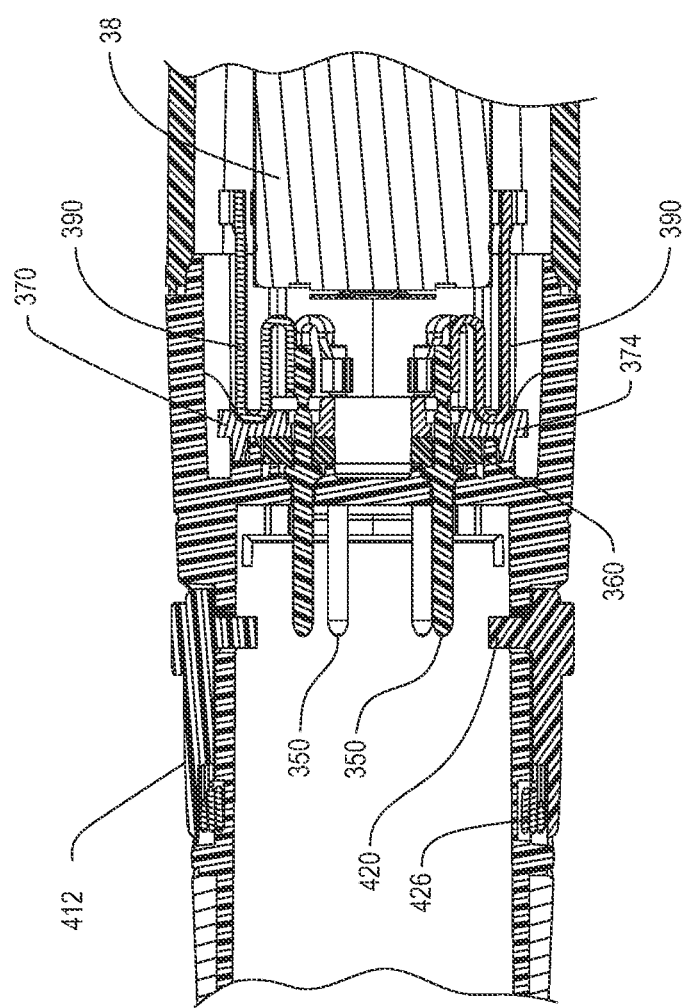
FIG. 33 is a cross sectional view of the battery and control module depicting the how the contact pins and latch assembly are mounted to the module housing.

Each pin 350 is seated in a separate one of the through holes 210 formed in distal shell disc 206 as seen in FIG. 33. More particularly, the pin head 355 extends through the disc 206. In many versions of the invention the components forming BCM 128 are designed so that at room temperature (22° C.), the pin head 355 has an outer diameter that is approximately −0.2 to 0.3 mm less than the diameter of the associated through hole 210. The abutment of stopper distal section 354 against the proximally directed face of disc 206 limits the forward longitudinal movement of the pin 350 through the disc.

A seal 360 and a cap 370, seen in FIGS. 19 and 33, cooperate to form barriers to the ambient environment between the BCM housing and pins 350. The seal 350, now described by reference to FIG. 36, is formed from an elastomeric material able to withstand the rigors of the sterilization processes to which the BCM 128 is exposed. In some versions of the invention seal 360 is formed from EPDM rubber. Seal 360 is generally shaped as a washer. There is a center located through hole 362. The body of the seal is further shaped to have a number of pin holes 364, two holes identified. Pin holes 364 are parallel to through holes 362. The number of pin holes equal the number of contact pins 350 integral with the BCM 128. The pin holes 364 have a diameter that is 0.2 to 0.3 mm greater than the diameter of the pin trunks 351.

Seal 360 is further formed to have circularly shaped ribs 365 that project forward from the distally directed face of the seal. Each rib 365 extends forward from and around a separate one of the pin holes 364. In cross section, each rib 365 has a convex shape.

The cap 370, as best seen in FIG. 37 is generally disc shaped. The distally directed face of cap 370 is planar. A through hole 372 extends through the center of the cap 362. Cap 360 includes a ring 374, partially seen in FIG. 37, that extends forward from the distally directed face of the cap. Ring 374 has an inner diameter that facilitates a contact fit against the outer perimeter of ring 211 integral with distal shell disc 206. The outer perimeter of the ring 374 is spaced inwardly from the outer perimeter of the main body of the cap 370.

Cap 370 is also formed to have a number of arcuately spaced apart tabs 376 that extend outwardly from the main circularly shaped body of the cap. Tabs 376 are spaced apart from each other so as to define a notch 378 between the tabs. A number of through holes 380, two holes identified, extend proximally to distally through the cap 370. Through holes 380 are positioned so that, when the BCM 18 is assembled each cap through hole 380 will be in registration with a separate one of the seal pin holes 364. Each through hole 380 is formed with a counterbore (not identified).

The cap 370 is further formed so a circular rib 382 extends outwardly from the proximally directed face of the main body of the cap. Rib 382 is located around hole 372. Additional linear shaped ribs 384 project radially outwardly from the outer perimeter of rib 384. The cap 370 is also formed to have a number of indentations 386. Each indentation 386 is concave in shape. Each indentation 386 is associated with a separate one of the through holes 380. A small groove, present for manufacturing reasons extends between some of the through hole counterbores and the associated indentation 386.

When the battery and control module 128 is assembled, a contact pin 350 is seated in each one of the through holes internal to the distal shell web 206. Seal 360 is fitted over the trunks 351 of the contact pins 350. The seal 360 is positioned so that seal ribs 365 abut the proximally directed annular surface of the adjacent pin stopper proximal section 353. Cap 370 is fitted over the seal 360. More particularly the cap is positioned so that cap ring 374 seats against ring 211 internal to the distal shell 162. As part of this process, cap 370 is oriented so that the tab 213 integral with distal shell 162 seats in cap notch 378. This tab-in-notch seating temporarily holds the cap in the proper orientation relative to the distal shell 162. Cap 370 is then welded or otherwise secured to the distal shell.

As a result of the dimensioning of the components forming battery and control module 128 is that the cap 370 presses the seal ribs 365 against the stoppers integral with contact pins 360. The distally directed face of seal 360 presses against ribs 207, 208 and 209. The abutment of the seal against these surfaces causes the seal to form a barrier between the ambient surroundings and the interior of the BCM housing.

Figure 35:
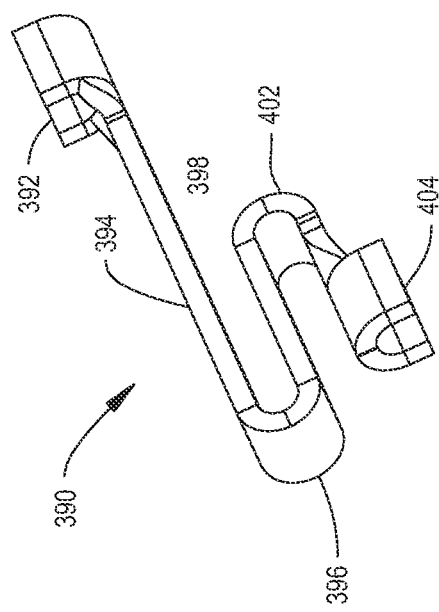
FIG. 35 is a perspective view of a connector of the battery and control module.

Returning to FIGS. 19 and 33 it can be seen that connectors 390 provide the conductive links between the wires that extend from the tool unit controller 530 and the contact pins 350. The connectors 390 are formed from conductive material, typically the material from which the contact pins 350 are formed. A single connector 390, as seen in FIG. 35, includes a U-shaped foot 392. A bar like leg 394 extends distally forward from the foot. At the distal end of the leg 394, connector 390 has a bend 396. Extending proximally from bend 396, the connector 390 has a bar shaped neck 398. A bend 402 is located at the proximal end of neck 398. A head 404 is located at the distally directed end of bend 402. Head 404 is U-shaped. Owing to the orientation and shape of bends 396 and 402, the longitudinal axes of connector leg 39, neck 398 and head are parallel. Also owing to the shaping of the connector, head 404 is understood to be located proximally rearward of bend 396. Further, the material from which the connector 390 is formed is selected so that bends 396 and 402 are flexible.

It is still a further feature of the components forming BCM 128 that the connectors 390 have a side-to-side width that facilitates the positioning of bends 396 in indentations 386 formed in cap 370.

Upon assembly of the BCM 128, each connector 390 is positioned so the connector bend 306 is press fit into an indentation 386 in the cap 370. The head 404 of the connector 390 is wrapped around the proximal section of the trunk 351 of the connector pin with which the connector is associated. The wire that extends from the tool unit controller 530 component to which the connector is to be attached is secured in the foot 392 of the connector 390. Solder is typically employed to ensure the wire remains attached to the connector foot 392 and the connector head 404 stays attached to the associated connector pin 350.

A further feature of this invention is that when the connectors 390 are connected to the contact pins 350 and seated in shell 370, the feet 392 and legs 394 of are arranged in a circle. This circle is of sufficient diameter so the distal end of the cell 38 mounted to the chassis lower frame 296 can be seated within the circle.

Figure 38:
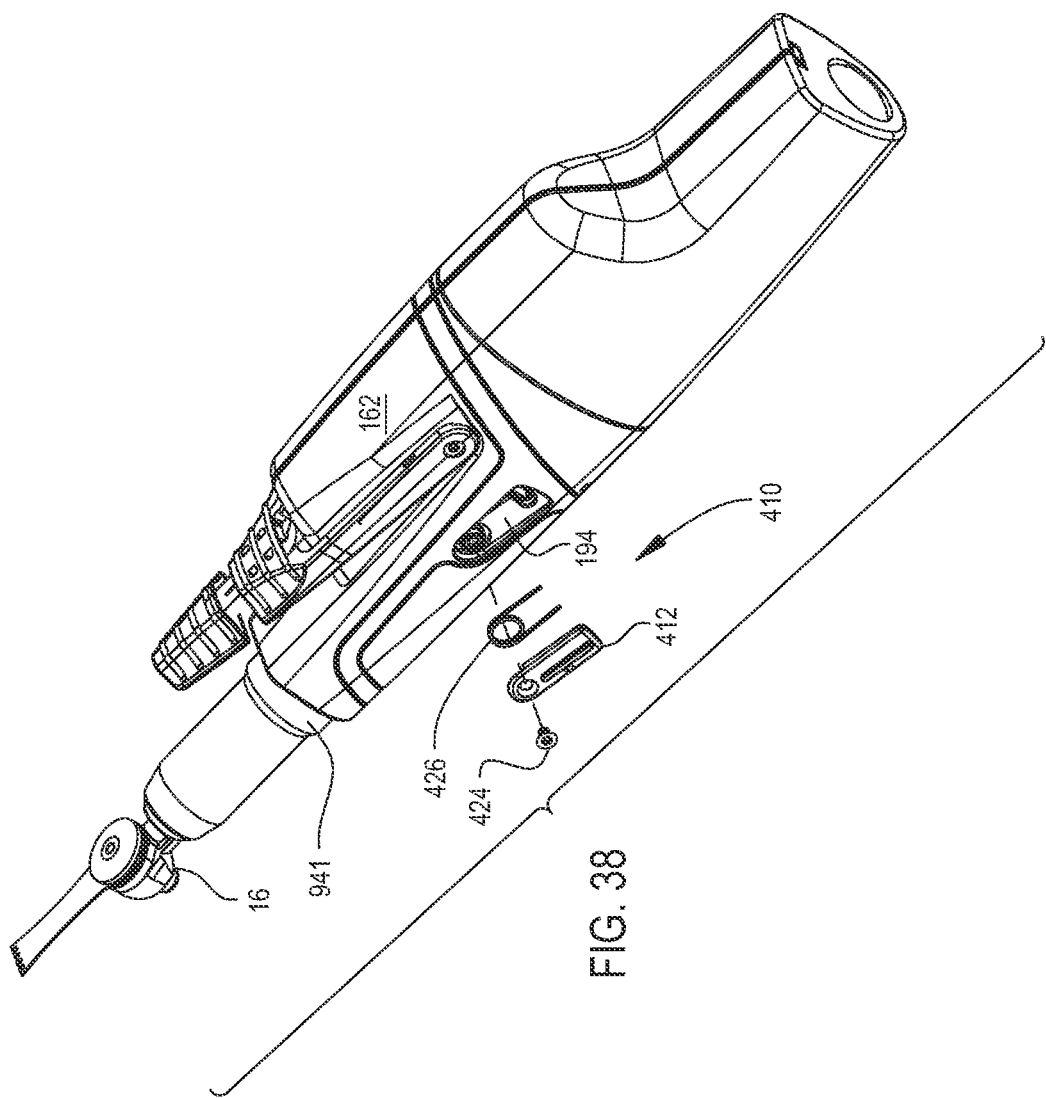
FIG. 38 is an exploded view of the latch assembly components integral with the battery and control module.

A latch assembly 410, now generally described with respect to FIG. 38, cooperates with complementary features integral with tool unit 124 to releasably hold the tool unit in BCM bore 214. While not illustrated, it should be understood that in many versions of the invention there are two latch assemblies 410. One latch assembly 410 is attached to each side of the BCM distal shell 162. Each latch assembly 410 engages in a complementary notch 856 (FIG. 56) with the tool unit 124. The latch assemblies 410 must be simultaneously actuated to remove the tool unit 124 from the BCM 128.

Figure 39:
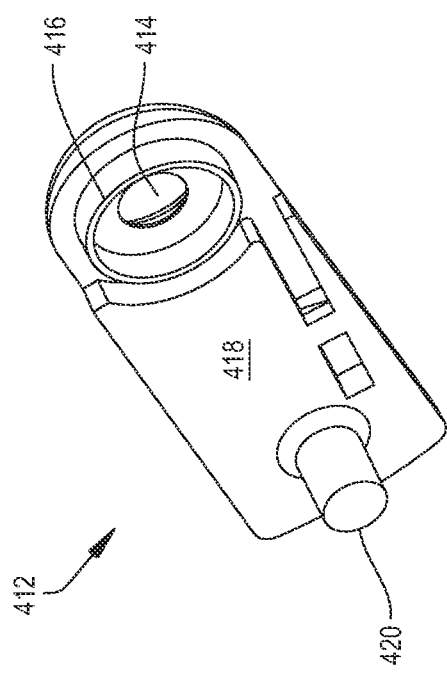
FIG. 39 is a perspective view of the structure of the release tab of the latch assembly.

Each latch assembly 410 includes a release lever 412 seen in FIGS. 38 and 39. The release lever 412 is a generally rectangularly shaped piece of sterilizable plastic. The distal end of the release lever 412 is rounded. Release lever 412 is dimensioned to seat in and pivot in void space defined by the recessed surface 194 of the side of the distal shell to which the lever is mounted. Proximal to the distal end of the lever 412, the lever is formed to have bore 414 that extends through the lever. A ring 416 extends inwardly from the inwardly directed face of the lever 412. Ring 416 is concentric with and radially spaced outwardly from bore 414. The lever is formed so that ring 416 seats between the two ribs integral with the boss 202 adjacent the recessed surface 194.

Proximal to and spaced away from ring 416, the lever 412 has a raised surface 418. The lever 412 is further formed so a notch 420 extends inwardly from the raised surface 418. Notch extends along a tangent line that extends from an outer surface of ring 416. A pin 420 extends outwardly from raised surface 418. Pin 420 is located a slight distance forward of the proximal end of the release lever 412.

When the BCM 128 is assembled, the release lever 412 is seated against the distal shell recess surface 194. Specifically, the lever is positioned so that the shell bore 204 and lever bore 414 are coaxial and pin 420 extends through shell opening 198. A fitting 424 that extends through the lever bore 414 and is securely attached to the surface of the distal shell that defines shell bore 205 hold the lever to the shell so the lever can pivot over recessed surface 194.

A torsion spring 426 is disposed between the shell 162 and the release lever 412. The circular base of the torsion spring over the boss 202 integral with the shell. One leg of the spring 426 is seated in the linear extension of shell recessed surface 196. The opposed leg of the torsion spring 426 seats in lever notch 420. Spring 426 thus places a force on the release lever 412 that normally positions the lever so that the proximal end of the lever is located below the distal end. Finger or thumb force is sufficient to overcome the biasing force of spring 426 and pivot the lever 412.

The BCM trigger switch 440 is now described by reference to FIG. 40-44. Trigger switch 440 includes a fork 442 that is pivotally attached to the BCM housing. A beam 472 holds a finger tab 488 to the fork 442. Beam 472 slidably holds finger tab 488 to the fork 442 so the spacing of the tab from the fork can be selectively set.

Figure 40:
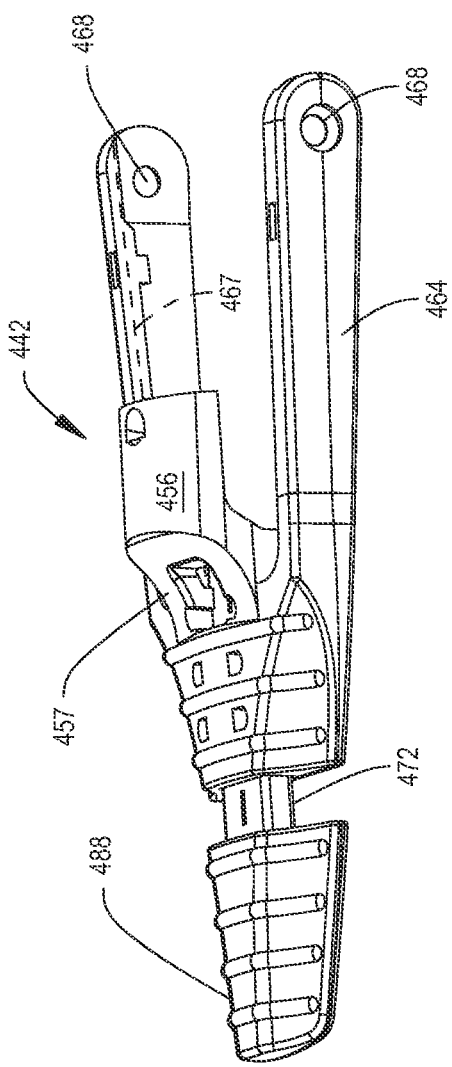
FIG. 40 depicts the fork and finger tab of the trigger switch of the battery control module.
Figure 41:
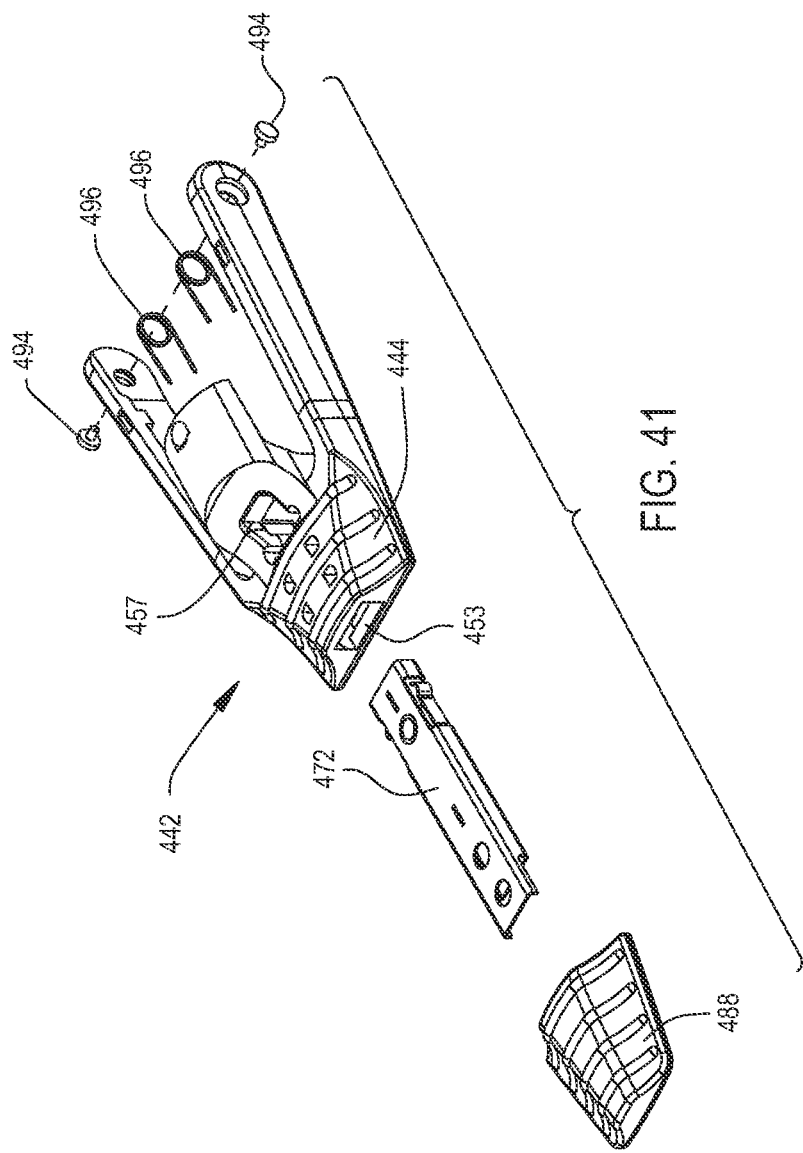
FIG. 41 is an exploded view of a number of the components of the trigger switch.
Figure 42:
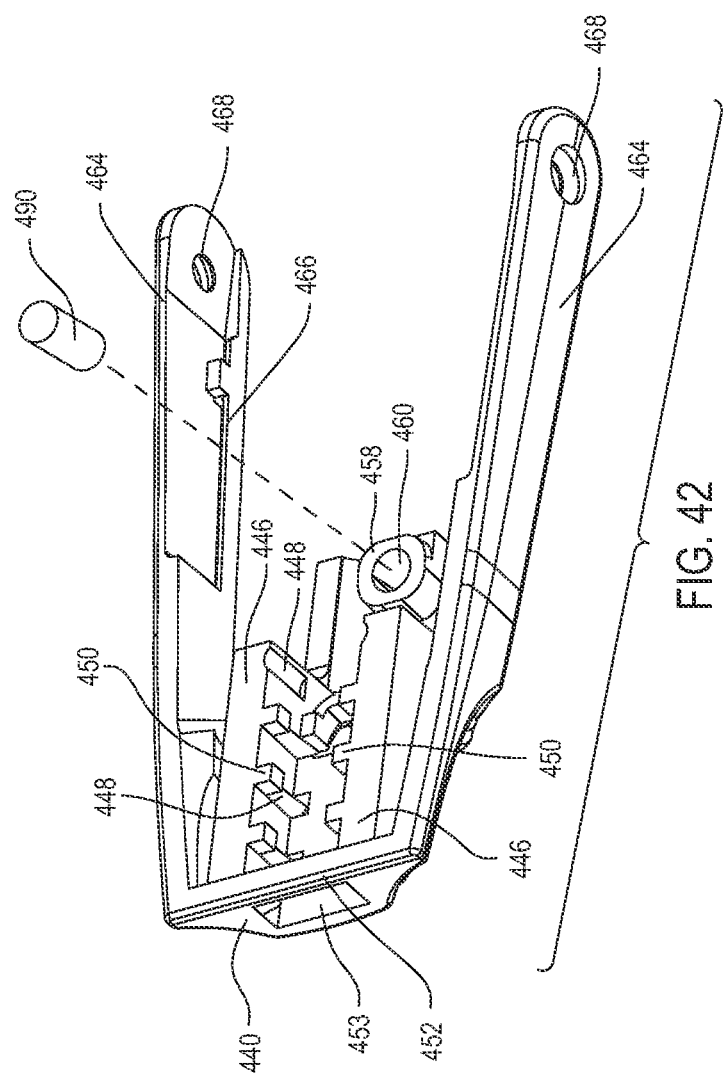
FIG. 42 depicts the underside of the switch fork and the magnet of the trigger switch.

Fork 442 as seen in FIGS. 40 through 42 is formed from a single piece of plastic able to withstand the rigors of sterilization. The fork 442 is shaped to have a base plate 444. Plate 444 has tapered sides (not identified). Two parallel bars 446 extend downwardly from the undersurface of plate 444. The bar 446 are formed to have four indentations 448, two indentations identified, that are generally vertically oriented. Indentations 448 are in cross section, semi-circular in shape. Each indentation 448 on one bar 446 faces a complementary indentation on the opposed bar. One each bar, below the three distalmost indentations a rectangular tab 450 extends outwardly towards the opposed bar. Fork 442 is further shaped so that a web 452 extends between the distal ends of the bars 446. Plate 444, bars 446 and web 452 thus collectively define a rectangular opening 453 into the distal end of the fork 442.

A thumb 456 extends proximally rearward from the proximal end of fork base plate 444. The fork is formed so that thumb 456 is elevated relative to the base plate 444. Collectively the base plate 444 and thumb 456 are formed to define a window 457 between the plate and the thumb. Thumb 456 is formed so as to have a boss 458 that extends downwardly from the undersurface of the thumb. The boss 458 is formed to have a closed end bore 460.

Two tines 464 also extend proximally away from fork base plate 444. The fork 442 is formed so that as each tine extends proximally away from the base plate 444, the tine tapers a small distance away from the proximal-to-distal longitudinal axis through the base plate. The components forming the BCM 128 are shaped so that each tine 464 seats against a distal shell side panel 168. Each tine 464 is formed to have a ledge 466, one ledge identified, that projects inwardly from the inner surface of the tine. Ledges 466 thus extend inwardly toward each other. The ledges 466 extend distally forward from locations forward of the proximal ends of the tines 464. Each tine 464 and associated ledge 466 is shaped to define a groove 467 (one shown in phantom) that extends upwardly from the undersurface of the ledge. Proximal to the ledge 466, and forward of the proximal end of the tine 464, a bore 468 extends side-to-side through the tine. Each bore 468 is formed with a counterbore (not identified) that is open at the outer face of the tine.

Beam 472, seen in FIGS. 41, 43 and 44, is formed from a metal plate that is bent to provide the beam with a shape in cross section that is generally that of a rectangle. More specifically, the beam is shaped to slidably fit in the rectangular opening 453 in the front of fork 442. The opposed sides of the beam are shaped to form in each side a leg 474 that extends proximally from the section of the beam from which the leg extends Each leg 474 has a foot 476. Each foot 476 is semicircular in shape and is further shaped to extend outwardly from the side of the beam with which the foot is associated. Beam feet 476 are dimensioned to seat in the indentations 448 formed in fork 442.

Markings are formed on the top facing surface of beam 472. A first marking a "|" marking 478 is located immediately forward of the proximal end of the beam. Immediately proximal to marking 478 is a "○" marking 480 A second "|" marking, marking 482 is located approximately 1 cm of marking 480. Beam 472 is further formed to have tab 484 that extends downwardly from the undersurface of the beam. Tab 484 is ramp shaped in that as the tab extends distally forward from the portion of the beam from which the tab extends the tab extends diagonally downwardly. Tab 484, which is flexible, extends below web 452 when the beam is initially inserted in fork opening 453. The tab 484 thus prevents the beam and attached finger 488 from being removed from the fork 442.

Finger tab 488 is disposed over the distal end of beam 472. Trigger switch 440 also includes a magnet 490. Magnet 490 is seated in the closed end bore 460 internal to thumb 456.

Fasteners 494, seen in FIG. 41, seated in tine bores 468 hold the trigger switch 440 to the BCM so the switch is able to pivot. One end of each fastener 494. A torsion spring 496, also seen in FIG. 41, is disposed around each boss 172 integral with the distal shell 162. One leg of each spring 496 is seated in the linear extension of the recessed surface 170 of the shell. By extension, this spring leg seats on the bar 178 immediately below the recessed surface 170. The opposed leg of each torsion spring 496 seats in the groove 467 formed in the adjacent tine 464 of fork 442. The torsion springs 496 thus impose a force on the other components of the trigger assembly that normally holds the finger tab so that the tab is spaced above the distal end of the BCM. Finger force is sufficient to overcome the force imposed by springs 496.

C. BCM Tool Unit Controller

A basic understanding of tool unit controller 530 internal to battery and control module 128 is obtained by reference to FIG. 45. Controller 530 includes a tool unit driver circuit (T.U. DRIVER) 620. Driver circuit 620 contains the components that source and sink the energization signals supplied from the cells 38, the BAT+ and BAT− signals, over the correct BCM pins 350. A tool unit drive controller 770 selectively enables and sets the components that comprise driver circuit 620 to cause the outputting of the appropriate energization signals by the driver. In FIG. 45 only single line connections are connected by the tool unit drive controller 770 and the circuits to which the controller is connected. It is understood that this is for ease of illustration only. In actuality, there are plural lines between controller 770 and the associated circuits.

Tool unit drive controller 770 sets the states of the driver components based on a number of input signals. One set of input signals comes from the trigger sensor circuit (TRG SNRS) 560. Trigger sensor circuit 560 includes the below discussed sensor 566 internal to the void space internal to the BCM housing that generates signals as a function of the actuation of the trigger switch 440 A second set of input signals applied to the tool unit controller are generated by a tool unit sensor circuit (T.U. SNSRS) 590. The tool unit circuit 590 includes the sensors 594 internal to the BCM that output signals representative of the operating state or condition of the power generating unit internal to the tool unit. A third set of input signals upon which the tool unit regulates the sourcing of energization signals comes from a current sense (ISNS) circuit 670. Current sense circuit 670 monitors the current drawn by the tool unit power generating unit as well as the voltage across the power generating unit 950. Current sense circuit also monitors the current sourced by cells 38.

A wake up circuit 702 is also connected to both pins 350 and the tool unit drive controller 770. Wake up circuit 702 monitors whether or not a load is present or a signal is applied or a across the pins 350 when the BCM 128 is not connected to a charger or a tool unit. When the wake up circuit 702 makes such a detection, the wake circuit asserts signals to the tool unit drive controller 770 so as to inform the controller that the BCM is either being charged or a tool unit 124 has been attached.

Driver controller 770 also includes a communications (COMM) circuit 730. Communications circuit 730 selectively applies power to, reads data from and writes data to a memory 910 (FIG. 60) internal to the tool unit 124. Drive controller 770 also actuates indicators 750 integral with the battery and control module (BCM INDCTRS). These indicators 750 provide an individual using power surgical tool assembly 120 information regarding the operating state of the assembly.

Figure 46:
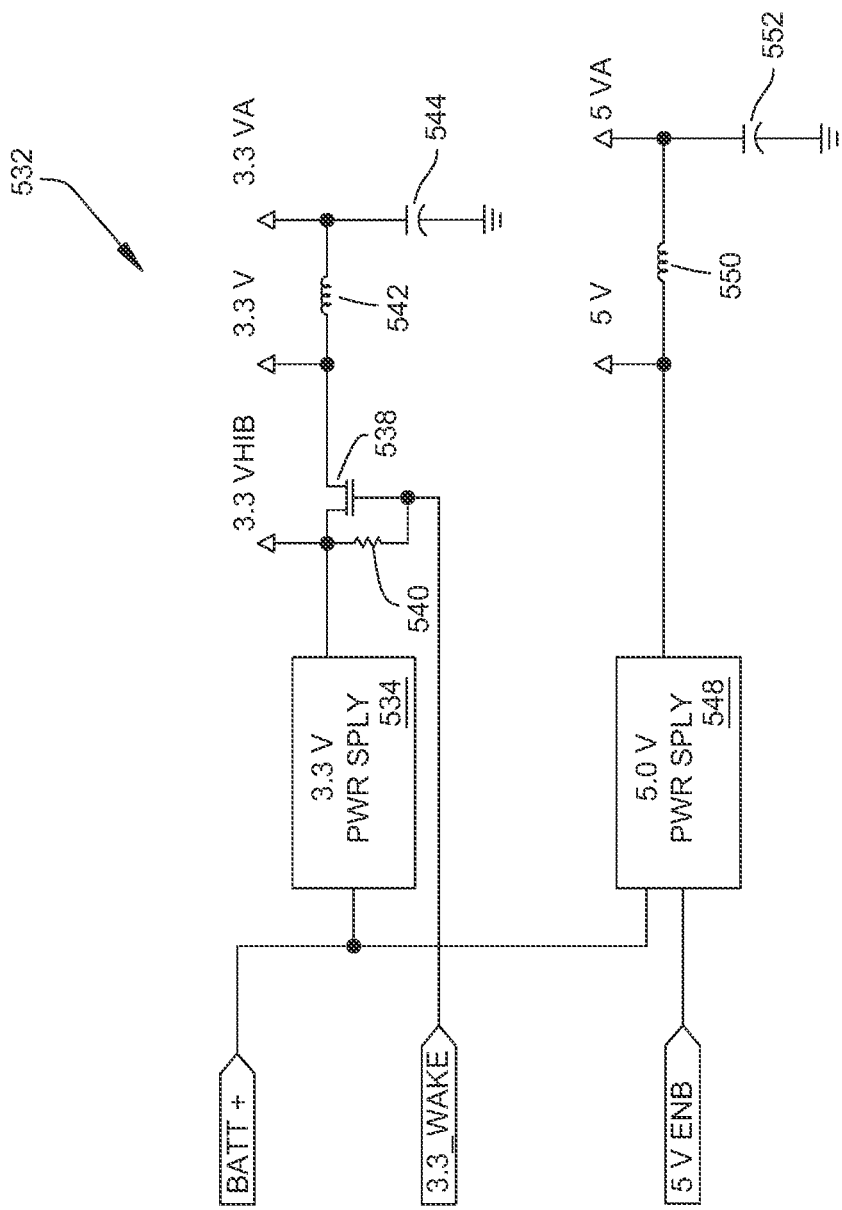
FIG. 46 is a block and partial circuit diagram of the power supply circuit of the tool unit controller.

Voltages for both energizing the components of the tool unit controller 530 and for reference purposes are supplied by a power supply circuit (PWR SPLY) 532 also connected to the drive controller 770. As seen in FIG. 46, power supply 532 includes a 3.3 Volt power supply 534. The input into power supply 532 is the BAT+ signals from the cells 38. In one version of the invention an LT3970HMS step-down voltage regulator available from Linear Technology of Milpitas, Calif. is used as power supply 532. This power supply draws a low quiescent current, typically 10 micro Amps or less and, more preferably, 5 micro Amps or less. Not depicted are the resistors and capacitors tied to power supply 532 to ensure the proper output of the 3.3 Volt signal.

The 3.3 Volt signal output by power supply is output over an inductor 536. This signal is always available as a 3.3 Voltage hibernate signal (3.3 VHIB) signal. This 3.3 VHIB signal is applied to a pin integral the drive controller 770 that receives a hibernation voltage that is applied to the controller.

The signal from inductor 536 is also applied to the source of a p-channel MOSFET 538. A resistor 540 is tied between the source and gate of MOSFET 538. The signal present at the drain of MOSFET 538 is available as 3.3 V digital signal. This signal is output on a bus, not illustrated that is applied to the other components of tool unit controller 530 that require a 3.3 V digital signal. The signal present at the drain of MOSFET 538 is also applied to an inductor 542. The signal at the end of inductor 542 spaced from MOSFET 538 is applied through a capacitor 544 to an analog ground. A capacitor 544 is tied between the end of inductor 542 spaced from supply 534 and ground. The signal present at the junction of inductor 542 and capacitor 544 is available is the 3.3 VA analogue 3.3 Volt signal. This signal is output on a bus (not illustrated) to the other components of the tool controller 530 that require a 3.3 Volt analog signal.

The MOSFET 538 thus controls the outputting of the 3.3 Volt digital signal and the 3. Volt analogue signal by power supply 532. The MOSFET 538 is normally turned off so as to prevent the outputting of these two signals. A 3.3 Volt Wake (3.3V_WAKE) signal is applied to the gate of MOSFET 538 to turn on the MOSFET. The 3.3 Volt Wake signal, which is asserted low, is selectively output by the driver controller 770 as described below.

Power supply 532 also includes a 5 Volt power supply 548 which also receives the BAT+ voltage. In one version of the invention the LTC3245 DC/DC converter also available from Linear Technology is employed as the 5 Volt power supply 548. Not depicted are the resistors and capacitors tied to power supply 548 to ensure the proper outputting of the 5 Volt signal. The 5 Volt signal output by power supply 548 is output as a 5 Volt digital (5V) signal over a bus, not illustrated. This 5 Volt digital signal is thus available to the other components of the tool controller 538 that require this signal. The output signal from power supply 548 is also applied to an inductor 550. The end of inductor 550 spaced from power supply 548 is tied to analog ground through a capacitor 552. The signal present at the junction of inductor 550 and capacitor 552 is the 5 Volt analog (5 VA) signal. This 5 VA signal is applied to a bus, not illustrated. This 5 Volt analog signal is thus available to the other components of BCM tool unit controller 530 that require such a signal.

The on/off state of the 5 Volt power supply 548 is controlled by a 5 Volt enable (5V_ENB) signal. This 5 Volt enable signal is selectively output by drive controller 770. Normally, when the BCM is neither connected to a tool unit nor to a charger, the 5 volt power supply 548 is in the off state. In some versions of the invention, the 5 Volt enable signal is asserted as a high signal.

Trigger sensor circuit 560 is now described by reference to FIG. 47. The trigger sensor circuit includes at least one sensor, sensor 566 in FIG. 47. This particular sensor 566 generates a signal as a function of the displacement of trigger switch 440. Sensor 566 is thus able to monitor the intensity of the magnetic field emitted by magnet 490. In one version of the invention, sensor 566 is a Hall sensor that outputs an analog signal as a function of sensed field strength. One such sensor is the A1319 sensor available from Allegro Micro Systems if Worchester, Mass. As seen in FIG.

29, sensor 566 is seated in notch 292 formed in web 288 integral with the chassis upper frame 246.

Figure 47:
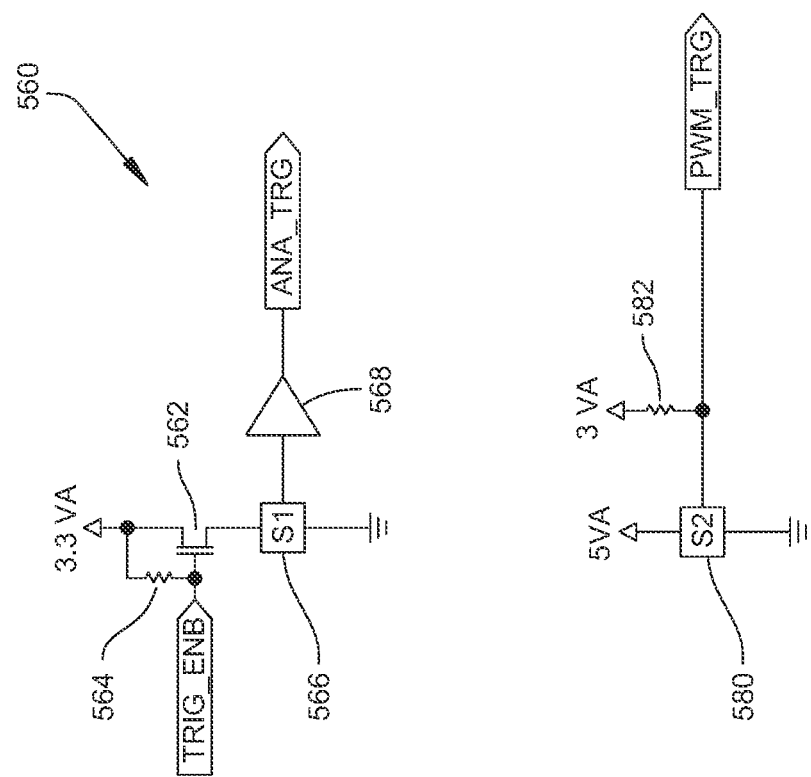
FIG. 47 is a block and partial circuit diagram of the trigger sensor circuit of the tool unit controller.

From FIG. 47 it can be seen that the 3.3 Volt analog signal is applied to the $V_{CC}$ pin of sensor 566. This signal is applied through a p-channel MOSFET 562. A resistor 564 is tied between the source and drain of MOSFET 462. The ground pin of sensor 566 is tied to analog ground. The $V_{OUT}$ signal from sensor 566 is applied to an amplifier with a low pass filter 568. The output signal from amplifier 568 is an analog trigger (ANA-TRG) signal. This signal is applied to the drive controller 770.

The on/off state of sensor 566 is controlled by MOSFET 566. Specifically a trigger sensor enable (TRIG_ENB) signal is applied to the gate of MOSFET 562 in order to turn on the MOSFET. Normally, MOSFET 562 is in the off state. The TRG_ENB signal, which is asserted low, is selectively asserted by the drive controller 770.

A second trigger sensor, sensor 580 is seen as part of the trigger sensor circuit 560 of FIG. 47. This second sensor 580 may not be physically within the above described battery and control module 128. However, this sensor 580 is present in the below described battery and control module accordingly the presence of this sensor and related components is now described. Sensor 580 is capable of monitoring the orientation of magnetic fields that may surround the sensor. It should be understood that sensor 580 is contained within the BCM housing in which it is disposed at a location in which it will vary its output signal as a function of the orientation of the sensed magnetic fields. In one version of the invention sensor 580 is a Hall effect sensor that outputs a PWM signal that varies as a function of field strength and orientation.

The 5 Volt analog signal is applied to the $V_{CC}$ pin of sensor 580. The ground pin of sensor 580 is tied to analog ground. A pull up resistor 582 is applied between the 3 Volt analog bus and the output pin of sensor 580. The signal present at the junction of sensor 580 and resistor 582 is applied to the drive controller as a pulse width modulated trigger (PWM_TRG) signal.

In the described version of the invention, the tool unit power generating unit is a brushless DC motor. The tool unit sensor circuit 590, now described by reference to FIG. 48, generates a signal or set of signals that indicate the rotation orientation of the motor rotor. In the depicted version of the invention, these signals are provided by three sensors 594. In some versions of this embodiment of the invention sensor 594 are identical to sensor 566 of trigger sensors circuit 560. From FIG. 28 it can be seen that each sensor 566 is seated in a separate one of the notches 334 formed in the web 332 integral with the chassis lower frame 296.

Figure 48:
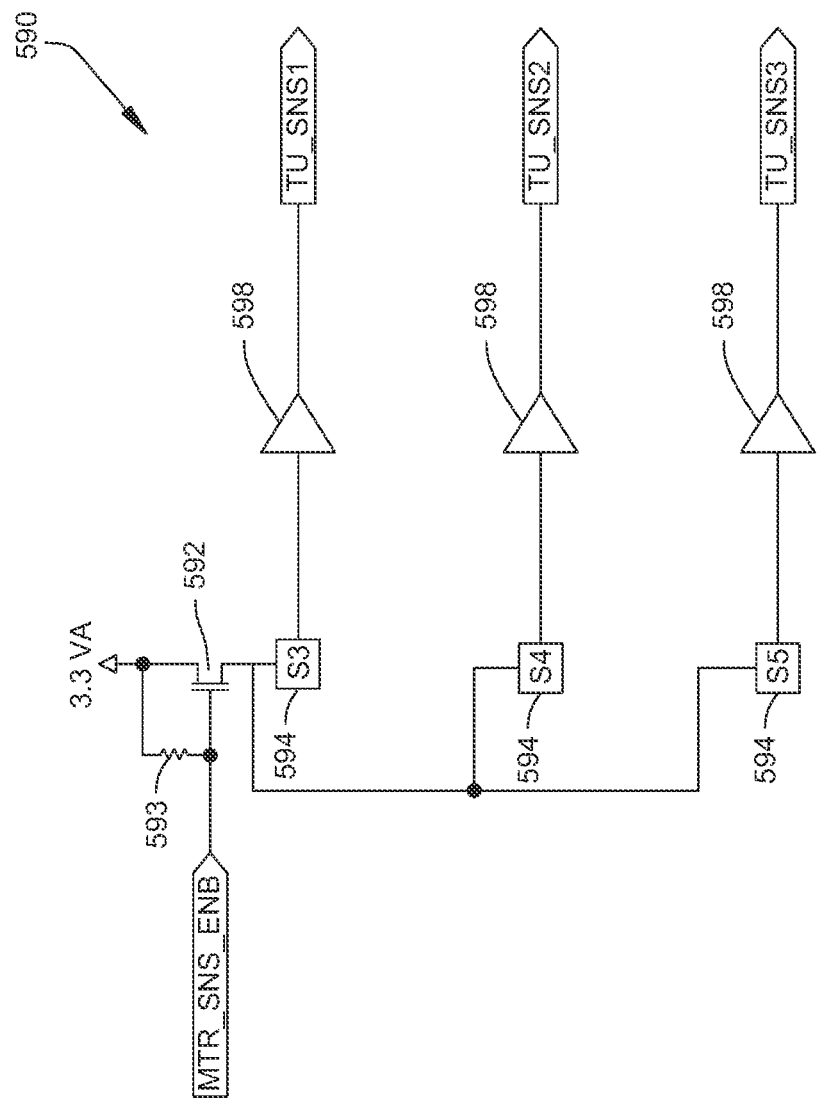
FIG. 48 is a block and partial circuit diagram of the tool unit power generator sensor circuit of the tool unit controller.

In FIG. 48, the three sensors 594 are separately labeled as S3, S4 and S5. The 3.3 Volt analog signal is applied to the $V_{CC}$ pin of each sensor 594 through a single p-channel MOSFET 592. A resistor 593 is tied between the source and gate of MOSFET 592. The on/off state of MOSFET 592 is controlled by a MTR_SNS_ENB signal, which is asserted low, that is output by drive controller 770. The ground pin of each sensor 594 is tied to the analog ground plane. The output signal generated by each sensor 594 is applied through an amplifier with a low pass filter 598. The output signals from the amplifiers 598 are the individual sensor signals, signals TU_SNS1, TU_SNS2 and TU_SNS3, respectively.

Figure 49A:
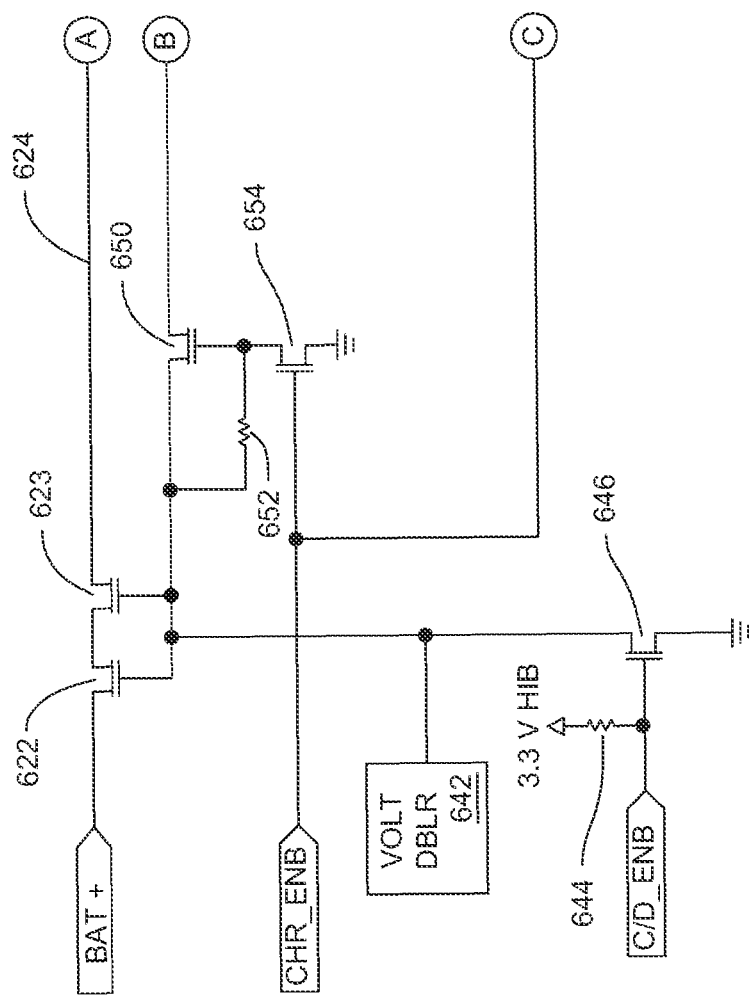
FIGS. 49A and 49B, when assembled together form a block and partial circuit diagram of the tool unit drive circuit of the tool unit controller.
Figure 49B:
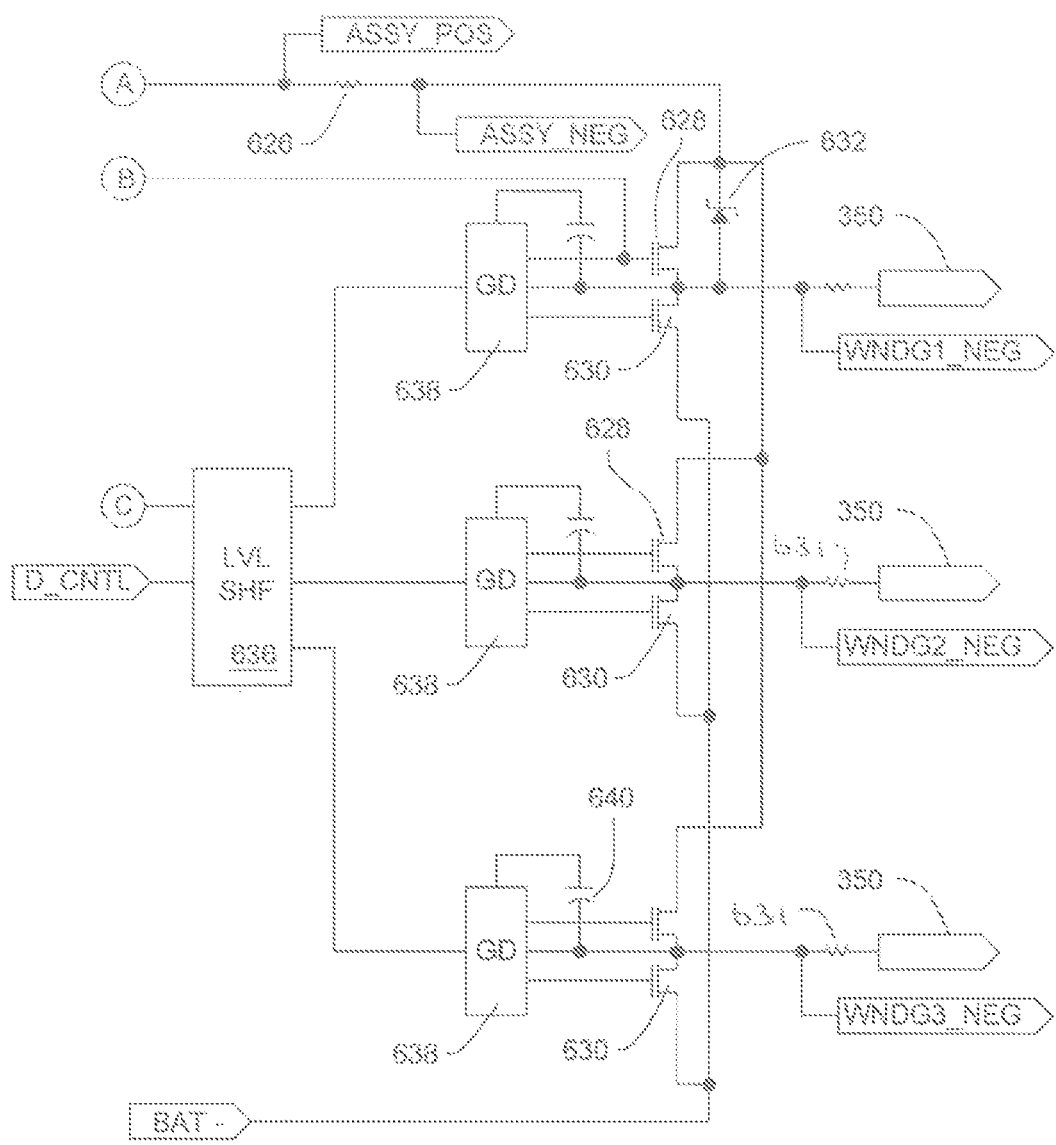

In the version of the invention described with reference to FIGS. 49A and 49B, the tool unit drive circuit 620 includes components able to selectively source/sink an energization signal to/from the plural windings of a brushless DC motor.

The energization signal is the BAT+ signal from the series connected cells 38. This signal is output through two n-channel MOSFETs 622 and 623 to a bus 624. Drive circuit 620 is arranged so that the source of MOSFET 622 is connected to the BAT+ contact of the cells 38 and the drains of the MOSFETs 622 and 623 are connected together. Bus 624 is connected to the source of MOSFET 623. A resistor 626 is inline with bus 624. The potential present at both end of resistor 626 is applied to the current sense circuit.

For reasons that are clear below, it should be understood that the signal present at the junction of MOSFETs 622 and 623 may be employed to power the 3.3 Volt power supply 534, (connection not shown).

The BAT+ signal on bus 624 is applied to high side drive MOSFETs 628 of an H-bridge. Each MOSFET 628 is an n-channel MOSFET. The sources of MOSFETs 628 are tied to bus 624, (two MOSFETs 628 identified). The source of an n-channel MOSFET 630 is tied between the drain of each MOSFET 628 and a bus connected to the BAT− contact (bus not identified). The junction of each pair of MOSFETs 628 and 630 is tied to a separate one of three contact pins 350. A Schottky diode 632 is forward biased between one of the pins 350 and the BAT+ bus 624.

Drive controller 770 asserts the signals that result in the turning on and turning off of MOSFETs 628 and 630. In FIG. 49B these signals are represented as driver control (D_CNTL) signals. A single signal line is shown for ease of illustration. It is understood that in actuality six individual driver control signals are asserted, one for each MOSFET 628 and 630. The driver control signals are applied to a level shifter, (LVL SHF) 636. Level shifter 636 shifts the signal level of each driver control signal from 3.3 Volts to 5 Volts. Not shown are the connections of the level shifter to the 3.3 Volt and 5 Volt digital buses.

The pair of voltage-level shifted driver control signals for each pair of MOSFETs 628 and 630 is applied to a gate driver, (GD) 638 for that pair of MOSFETs. Each gate driver 638 in response to the state of the drive control signals applied to the driver selectively applies/negates a signal to the gates of the attached MOSFETs 628 and 630. Gate drivers 638 provide shoot through protection. That is each driver 638 will not simultaneously applied a voltage to the gates of both of the MOSFETs 628 and 630 attached to the driver. The voltage each gate driver applies to the gate of the associated high side MOSFET 628 is boosted. A capacitor 640, one identified, tied between the junction of each pair of MOSFETs 628 and 630 and the boost pin of the gate driver 638 supplies the charge for this boosted gate voltage.

The $V_{CC}$ voltages for the gate drivers are supplied from the higher of the 5 Volt signal or the BAT+ signal, circuit not illustrated.

The above described MOSFETs 622 and 623 are turned on and off to regulating the discharging of the cells 38 and the charging of the cells over bus 624. A voltage doubler 642 applies potential to the gates of both MOSFETs 622 and 623 to selectively turn on the MOSFETs. The input signal into the voltage doubler 642 is a square wave. While not shown, it should be understood that this square wave is a signal that is output by the drive controller 770.

The output signal from the voltage doubler 642 is selectively applied to ground through an n-channel MOSFET 646. The 3.3 Volt hibernation signal is applied to the gate of MOSFET 646 through a resistor 644. A charge/discharge enable (C/D_ENB) signal is also selectively applied to the gate of MOSFET 646 from the drive controller 770.

The output signal from voltage doubler 642 is applied through a p-channel MOSFET 650 to the gate of one of the MOSFETs 628. Specifically this voltage is applied to the gate of the MOSFET 628 to which diode 632 is connected. The signal produced by the voltage doubler 642 is applied to a p-channel MOSFET 650. A resistor 652 is tied between the source and gate of MOSFET 650. An n-channel MOSFET 654 is tied between the drain of MOSFET 650 and digital ground.

A charge enable (CHG_ENB) signal selectively output by drive controller 770 is applied to the gate of MOSFET 654. The charge enable signal is also applied to a disable pin of the level shifter 636.

The signal at the junction of each MOSFET 628 and 630 is applied to the associated contact pin 350 through a resistor 631, (two resistors 631 identified). The signal present at the junction of the MOSFETs 628 and 630 is also applied to the current sense circuit 670.

Figure 50:
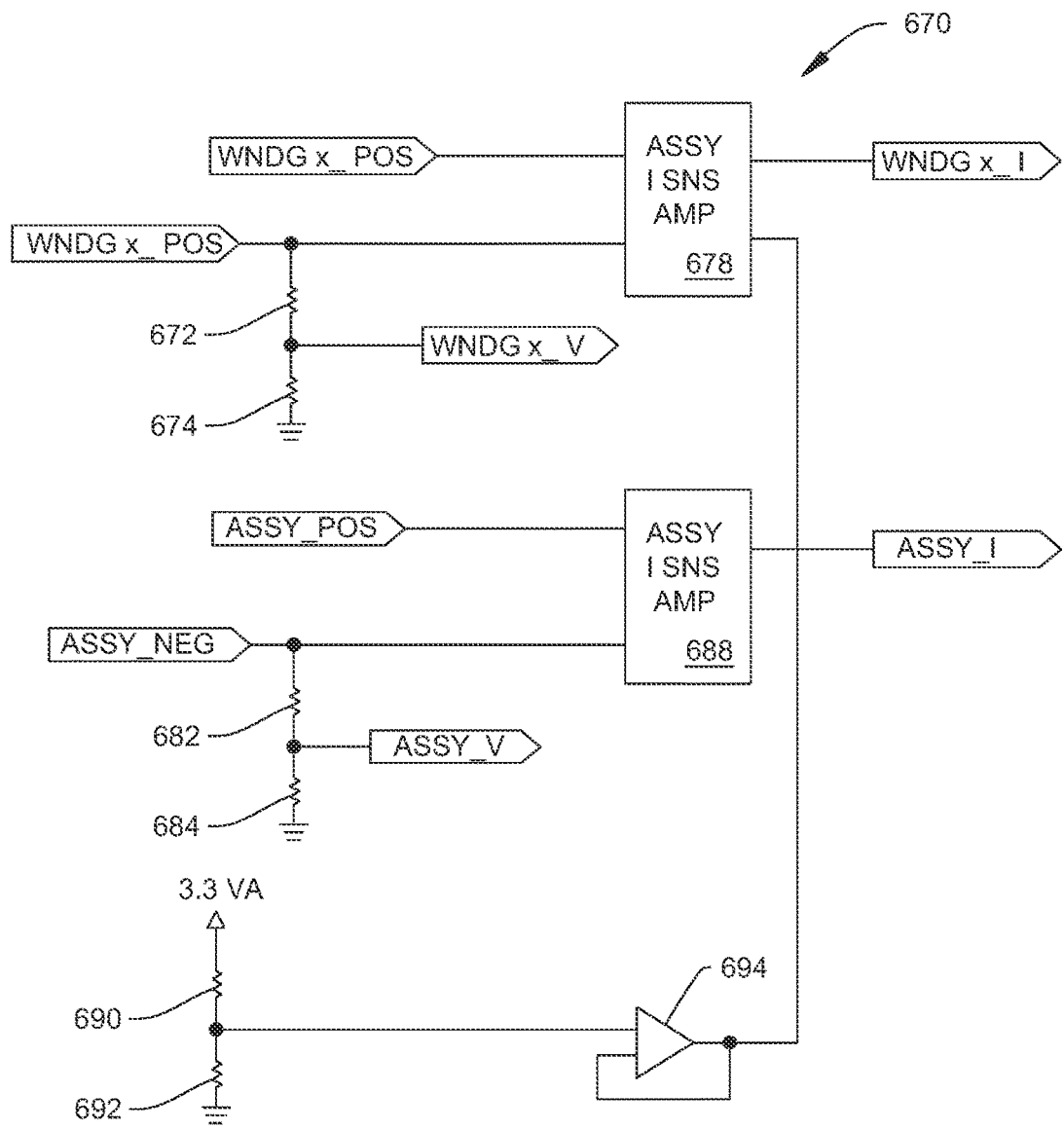
FIG. 50 is a block and partial schematic diagram of the current sense circuit of the tool unit controller.

The current sensor circuit 670 is now described by reference to FIG. 50. Current sense circuit 670 includes a number of amplifiers. Three separate voltages amplifiers output each output a signal representative of the current drawn by a specific one of the motor windings. In FIG. 50, to minimize redundancy, a single one of these amplifiers is represented as amplifier 678. The LT1999 bidirectional current sense amplifiers available from Linear Technology may be employed as these amplifiers. The $V_{+IN}$ signal to each winding current sense amplifier 678 is the voltage present at the junction of MOSFETs 628 and 630 to resistor 631 to which the winding 954 is connected. In FIG. 50 this is the WNDGx_POS signal. The $V_{-IN}$ signal to the amplifier 678 is the voltage present at the opposed side of the resistor 631. In FIG. 50 this is the WNDGx_NEG signal. To minimize drawing complexity, the WNDGx_NEG connections are not shown in FIG. 49B. The output signal for each amplifier 678 is a WNDGx_I signal, a signal representative of the current drawn by the winding.

The WNDGx_I signals for each of the windings are applied to the drive controller 770. In actuality, the current drawn through two of the windings 954 may be used to calculate the current drawn through the third winding 954. The WNDGx_I signal representative of the current drawn by the third winding 954 may be used as a check.

Each WNDGx_NEG signal is also applied to ground through two series connected resistors 672 and 674. The voltage present at the junction of the resistors 672 and 674 is output as a WNDGx_V signal representative of the voltage across the winding 954. The plural WNDGx_V signals are applied to the drive controller 770.

Current sense circuit 650 has a fourth current sense amplifier, amplifier 688. Amplifier 688 is used to measure the current drawn by the tool assembly 120 as a whole. The specific amplifier employed as the winding current draw amplifiers 678 may also be used as the assembly current draw amplifier 688. The signal present at the junction of MOSFET 623 and resistor 626, ASSY_POS signal, is applied to the $V_{+IN}$ pin of amplifier 688. The voltage present at the junction of resistors 626 to MOSFETs 628, the ASSY_NEG signal, is applied to the $V_{-IN}$ pin of amplifier 688. Based on the voltage drop across resistor 626 amplifier 688 produces as an output signal ASSY_I representative of the current drawn by the assembly 120. This signal is applied to the drive controller 770.

The PWRS_NEG signal applied to ground through two series connected resistors 682 and 684. The voltage present at the junction of resistors 682 and 684 is applied to the drive controller 770 as a signal representative of the voltage across the cells 38.

In order for amplifiers 678 and 688 to function the 5 Volt analog signal is applied the $V^+$ pins of the amplifiers. A reference voltage is also applied to the amplifiers. This reference voltage is based on the 3.3 Volt analog signal. Specifically, the 3.3 Volt analog signal is applied to voltage divider consisting of resistors 690 and 692. The voltage present at the junction of resistors 690 and 692 is applied to the noninverting input of an op amp 694. The output voltage of op amp 694 is tied back to the inverting input. The output voltage of the op amp is the reference voltage applied to the current sense amplifiers 678 and 680. It should be realized that the reference voltage applied to the amplifiers 678 and 688 varies with changes in the actual potential of the 3.3 Volt analog signal. This minimizes the effects of the drift of the 3.3 Volt analog signal.

Not shown is the capacitor that removes ripple from the input the non inverting input into amplifier 694. Also not shown are the MOSFETs that control the application of the 3.3 Volt analogue signal into amplifier 694. Drive controller 770 regulates the outputting of this 3.3 Volt analogue signal to the amplifier to ensure that it is only output during the periods in which BCM 128 is actually providing energization signals to the tool unit power generating unit 950.

Figure 51:
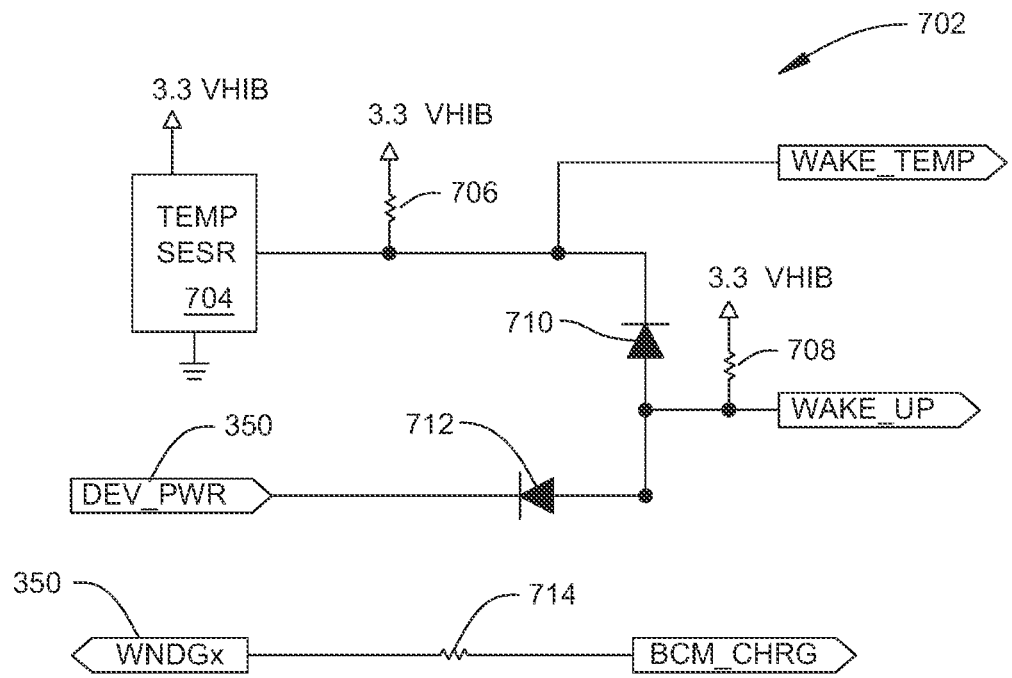
FIG. 51 is a block and partial schematic diagram of the wake up circuit of the tool unit controller.

Wake up circuit 702 as seen by reference to FIG. 51 includes a temperature sensor 704. Temperature sensor 704 monitors the temperature of the BCM 128. The 3.3 Volt hibernate voltage is applied to the sensor 704 through a resistor 706. In some versions of the invention, sensor 704 pulls the signal at the pin to which resistor 706 is connected to ground when the sensed temperature exceeds 80° C.

The signal present at the junction of sensor 704 and resistor 706 is applied to the drive controller as a temperature triggered wake up (WAKE_TEMP) signal. This signal, which is asserted LOW, is applied to the drive controller 770 to inform the controller that the BCM is being transitioned from the hibernate state to an awake state because the BCM is most likely being subjected to an autoclave sterilization process. While not illustrated temperature sensor provides a signal representative of the sensed temperature to the drive controller 770. Drive controller 770 records these temperatures in a memory (not illustrated). These temperatures as well as the length of the time the BCM 128 is held as these temperatures are recorded to provide a history of the sterilization processes to which the BCM has been exposed.

The 3.3 Volt hibernate signal is also applied to the pin of sensor 704 to which resistor 706 is connected through a resistor 708 and a diode 710. The signal present at the junction of resistor 708 and diode 710 is a general wake up (WAKE_UP) signal. As discussed below, the WAKE_UP signal is also asserted low. The anode of a diode 712 is connected to the junction of resistor 708 and 710. The cathode of diode 712 is connected to the connected to the BCM contact pin over which communications circuit 730 outputs a power signal to the tool unit microcontroller 909. In FIG. 51 this pin 350 is called out as the DEV_PWR pin.

Wake up circuit 702 also includes a connection to each of the contact pins 350 that are connected to the tool unit windings 954. In FIG. 51 the connection to only a single winding, the WNDGx connection is shown. The wake up circuit 702 includes a resistor 714 connected to each of these contact pins 350. The signal present at the end of the resistor 714 spaced from the WNDGx connection is a digital BCM_CHRG signal. The three BCM_CHRG signals are output to driver controller 770.

Figure 52:
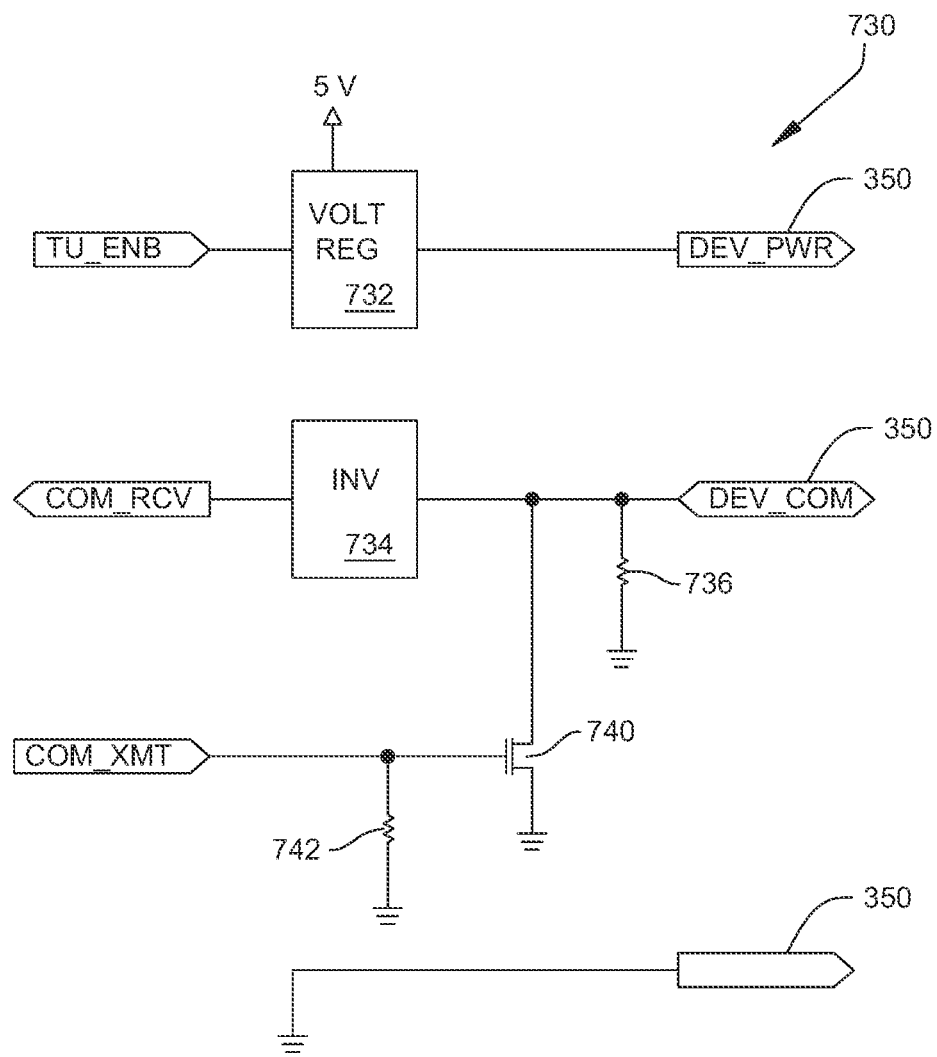
FIG. 52 is a block and partial schematic diagram of the communications circuit of the tool unit controller.

The communications circuit 730, now described by reference to FIG. 52, provides power to the below described microcontroller 911 and memory 912 internal to the tool unit 124. This power is provided from a voltage regulator 732. One such voltage regulator is the LT3050 Voltage Regulator available for Linear Technologies. The 5 Volt digital signal is applied to voltage regulator 732. The voltage regulator 732 selectively outputs a 3.3 Volt signal, the DEV_PWR signal, over one of the contact pins 350. This is the voltage is output through a tool unit socket pin 894 to a power bus on the flex circuit 912 internal to the tool unit 124 (tool unit power bus not shown). This contact pin 350 is the contact pin to which diode 712 of the wake up circuit 702 is connected. The voltage regulator 732 outputs this power signal when the drive controller inserts a TU_ENB signal to enable the tool unit 124.

A second contact pin 350 is also connected to communications circuit 730. This is the contact pin 350 over which data (DEV_COM) signals are transmitted to and received from the BCM 128. These are the signals that are exchanged the BCM 128 exchanges both with the tool unit 128 and the charger. This pin is connected to the input of an inverter with Schmitt trigger 734. The output signal from inverter 734 is the serial bit stream of signals that are received by the BCM. These are the input data and instructions forwarded to the drive controller as the COM_RCV signals.

A resistor 736 is tied between the DEV_COM signal contact 350 and ground. Also tied between contact 350 and ground is an n-channel MOSFET 740. A COM_XMT signal output by the drive controller 770 is selectively applied to the gate of MOSFET 740. A resistor 742 is connected between the gate of MOSFET 740 and ground. Not shown are pull up resistors internal to both the charger and tool unit. A digital logic voltage, typically the 3.3 Volt signal are applied to these pull up resistors. Drive controller 770 transmits data signals to the attached tool unit 124 or charger by selectively asserting the COM_XMT signal. When the COM_XMT signal is in the high state, MOSFET 740 is turned on. This pulls the signal present at the free end of the tool unit 128 or charger pull-up resistor to ground. Thus the changes of the signal level of this pull resistor are the signals received by either the tool unit microcontroller 909 or the charger.

The remaining contact pin 350 of the BCM 128 can also be considered part of the communications circuit 730. Specifically this pin 350 is used to establish the connection from the ground internal to the tool unit 124 and the ground of the tool unit controller 530.

Figure 53:
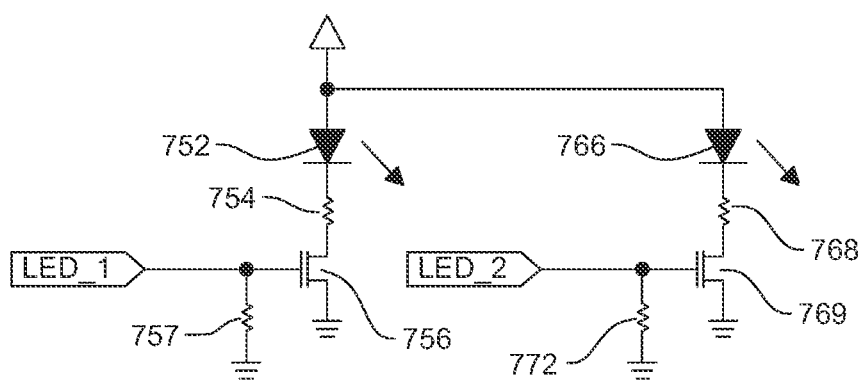
FIG. 53 is a schematic diagram of the indicators internal to the BCM of this invention.

The BCM indicators 750 include two LEDs 752 and 766 seen in FIG. 53. The cathodes of both LEDs 752 and 766 are tied to one of the sources of voltage internal to the BCM able to cause the emission of light by the LEDs. The cathode of LED 752 is tied to ground through a resistor 754 and an re-channel FET 756. An LED_1 signal selectively asserted by drive controller 770 is applied to the gate of the FET 756. Also tied to the gate of FET 756 is a resistor 757. The LED 752 emits green light.

The LED 766 emits amber light. The cathode of LED 766 is tied to ground through a resistor 768 and an n-channel FET 769. An LED_2 signal selectively asserted by the drive controller 770 is applied to the gate of FET 769. A resistor 772 is tied between the gate of FET 769 and ground.

The light emitted by both LEDs is applied to a light pipe 157 (FIG. 66) the exposed proximal face of which is mounted in a transparent window in end plate 140 of proximal shell 132.

Tool unit controller 530 contains a circuit that monitors the voltage across cells 38. When the tool unit 124 is attached to the BCM and the monitored voltage is at or above a level at which the BCM can source energization signals with sufficient current and voltage to the tool unit, drive controller 770 asserts the LED_1 signal. This results in the turning on of LED 752, the LED that emits green light.

If the detected voltage level drops to a level approaching the level at which the BCM can deliver appropriate current and voltages to the tool unit, tool unit controller 770 negates the assertion of the LED_1 signal. The LED_2 signal is asserted. The resultant emission of amber light by LED 766 provides an indication to the practitioner that the charge stored in the BCM may not be sufficient to adequately power the tool unit 124.

The drive controller 770 is any suitable processor for regulating the operation of tool unit power generating unit 950 and performs the described ancillary functions. One such controller is the XMC4504F100 family of microcontrollers available from Infineon Technology of Munich, Germany. This particular microcontroller has a 32 bit processor core with 1024 KB of flash memory.

A receiver 780 for wirelessly receiving signals emitted from a device remote to tool assembly 120 may also be integral with tool unit controller 530. The function of receiver 780 is discussed below.

D. Tool Unit

Tool unit 124 of powered surgical tool assembly 120 of this invention is now initially described by reference to FIGS. 53-55. Tool unit 124 includes an end cap 850 that is seated in a main tube 940. A head cap 941 is disposed over the main tube 940. Collectively, the end cap 850, shell 940 and head cap 941 form the housing of the tool unit 124. Disposed inside of the end cap 850 are socket pins 894 and 902. Socket pins 894 and 902 are the pins in which the BCM contact pins 350 seat to establish electrical connections between the tool unit 124 and the BCM 128. Memory 910 is also disposed in the end cap 850. The memory 910 stores the data describing the individual operating characteristics of the tool unit 124. The tool power generating unit 950 is disposed in shell 940. As seen only in FIG. 17, previously described head 16 attached to the distal end of shell 940. Again, the head removably holds the energy applicator 17, here a sagittal saw blade, to the tool unit 124 so the energy applicator can be actuated by the tool unit.

Figure 56:
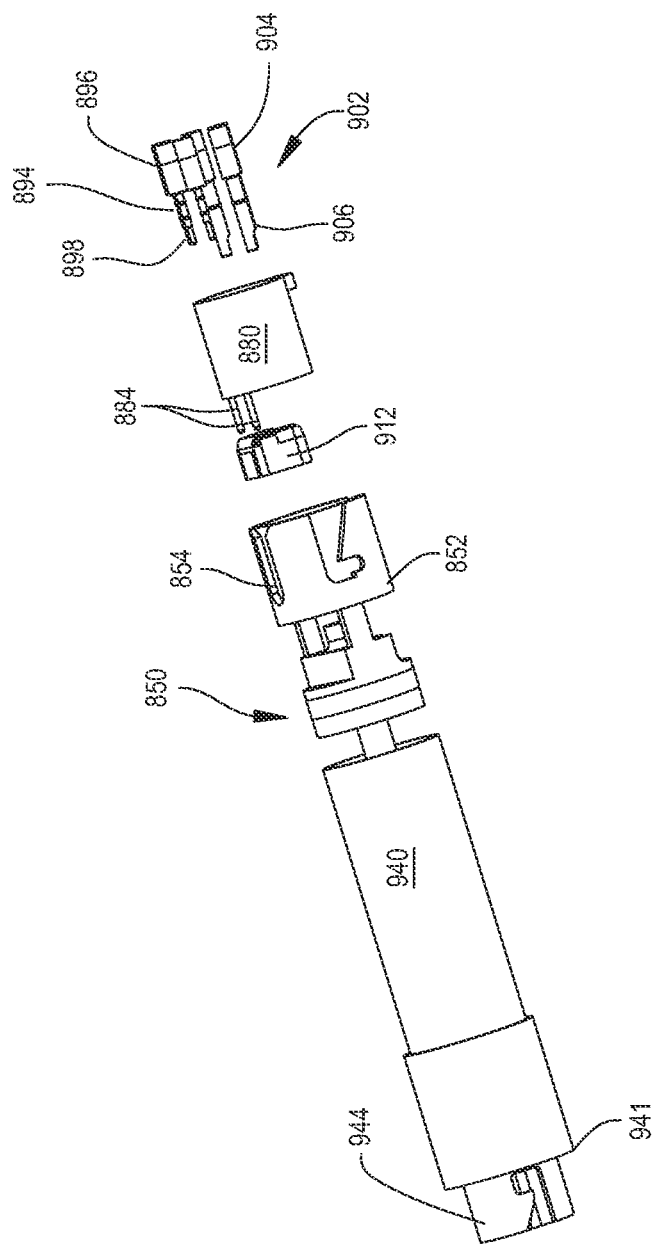
FIG. 56 is an exploded view of the tool unit of FIG. 54.
Figure 57:
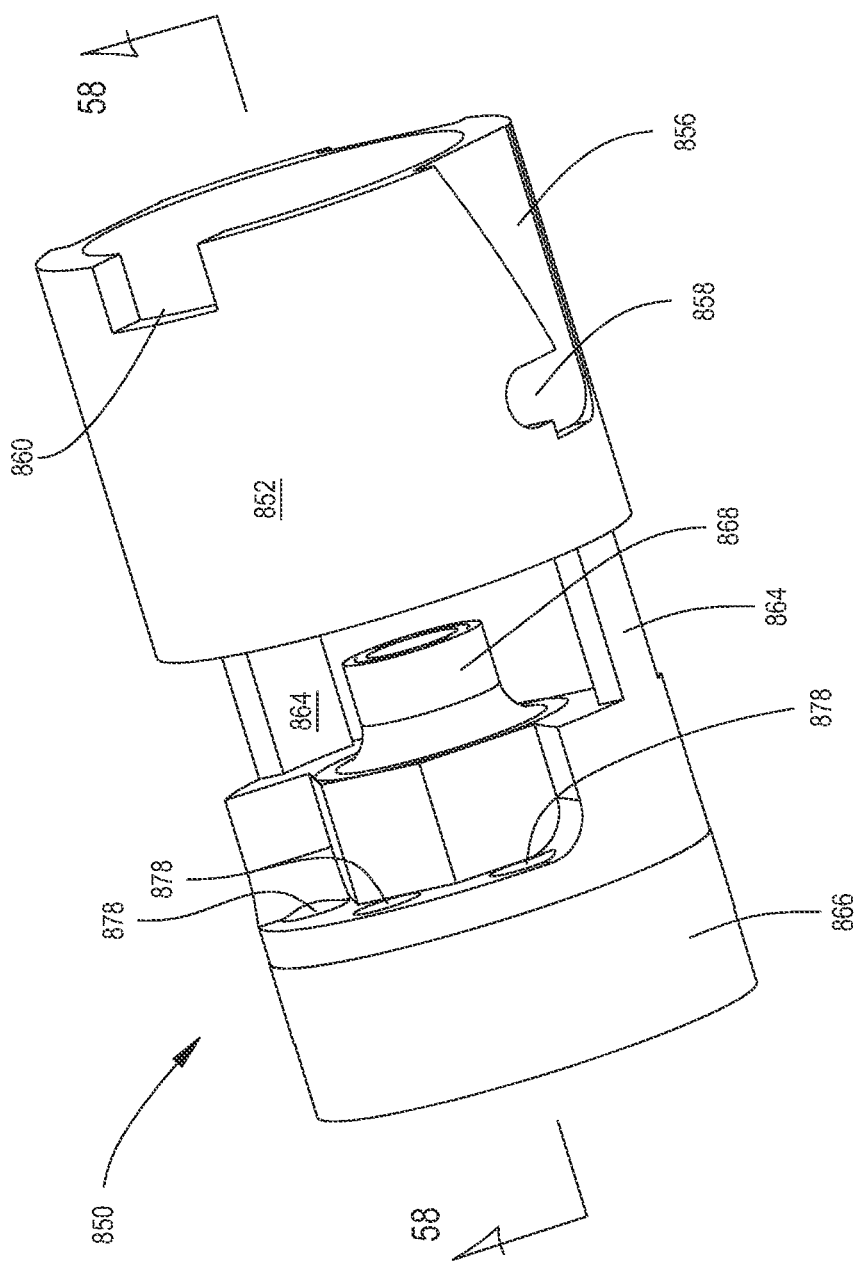
FIG. 57 is a perspective view of the proximal end cap of the tool unit of FIG. 54.

From FIGS. 56 and 57 it can be seen that end cap 850 has a tubular shaped foot 852. Foot 852 is formed to have three slots that extend inwardly from the outer surface of the foot. Each of the slots extends distally forward from the proximal end of the foot 852. A first slot, slot 854, is generally rectangular in shape. When tool unit 124 is seated in BCM bore 214 the BCM rib 217 seats in slot 854. Thus, if slot 854 is not present, a tool unit 124 that fits in the BCM bore 214 cannot be inadvertently pressed against BCM contact pins 390.

The two additional slots are slots 856, one slot 856 fully seen in FIG. 56. Each slot 856 has a wide proximal end and tapers inwardly distally along foot A short distance proximal to the distal end of the slot 856, each slot has an extension 858 that extends laterally form the longitudinal axis of the slot 856. Slot extensions 858 are dimensioned to receive pins 420 integral with release levers 412. Foot 852 is further shaped to define a notch 860.

Two legs 864 extend distally forward from foot 852. Legs 864 have arcuate outer surfaces (not identified). More particularly, the end cap 850 is shaped so that the outer surfaces of legs 864 define a circle that has a diameter less than the diameter of the circle defined by the outer surface of foot 852. Cap 850 is further shaped so that legs 864 support a generally cylindrically shaped head 866. Head 866 has an outer circumference that has a diameter essential identical to the diameter of the circle defined by the outer surface of legs 864. A neck 868 extends proximally rearward from the proximally directed face of head 866. The neck 868 is cylindrical in shape and has an outer diameter such that the neck is spaced radially inwardly from the inner surfaces of the surrounding legs 864 Cap 850 is further shaped so that the proximal face of neck 868 is located distally forward of the distal end of cap foot 852.

The end cap 850 is further formed so that the head 866 and neck 868 have a number of bores. A bore 870 extends axially through the whole length of neck 868. Bore 870 opens up into a bore 872 formed in the proximal portion of head 866. Bores 870 and 872 are coaxial. Bore 872 is larger in diameter than bore 870. The bore 872 opens into a bore 874 that is open at the distally directed face of head 866. Bore 874 is coaxial with and larger in diameter than bore 872. The head 866 is further formed to have a notch 876 that extends forward from the proximal face of the head and inward from the outer surface of the head. Notch 876 subtends an angle of approximately 120° around the outer circumference of the head 866. Three bores 878 seen only in FIG. 56, extend distally from the proximally directed face of notch 876. Bores 876 are centered on a single circle and are parallel with the proximal-to-distal longitudinal axis through the end cap 850. Each bore 876 opens into the annular step internal to the head between bore 872 and bore 874.

Figure 58:
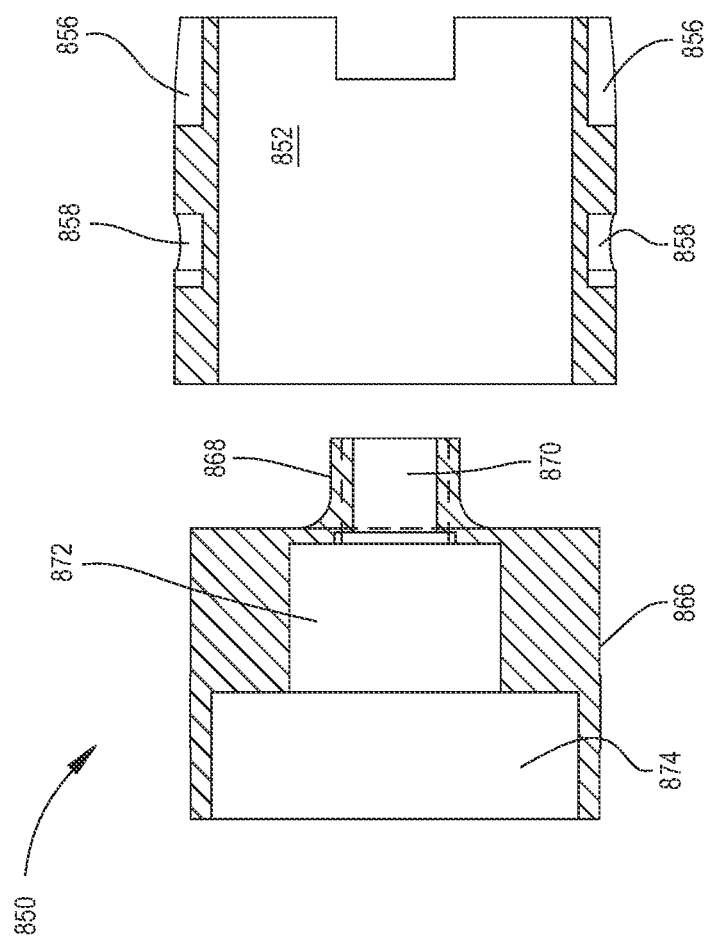
FIG. 58 is a cross sectional view of the end cap of FIG. 57 taken along line 58-58 of FIG. 57.

A socket 880, now described by reference to FIG. 58 is disposed in the void space internal to the end cap foot 852. Socket 880 is formed from an electrically insulating material able to withstand the effects of autoclave sterilization. Such material includes the material from which the shells 132 and 162 are formed. The socket 880 is generally cylindrically shaped and is dimensioned to press fit in the end cap foot 852. The socket 880 is formed to have at the proximal end a radially projecting tab 882. Tab 882 seats in foot notch 860 so as to prevent rotation of the socket 880.

The socket is further formed to have two cylindrically shaped fingers 884 that extend forward from the distal face of the socket. Fingers 884 are located on one side of the socket and are parallel to the proximal to distal longitudinal axis through the socket.

The socket 880 is formed to have a number of longitudinally extending bores that extend between the opposed proximal and distal faces of the socket. One bore, bore 888, is concentric with the longitudinal axis through the socket. The socket 880 has six additional bores, bores 890. Bores 890 are arranged in a circle that extends between bore 888 and the outer perimeter of the socket. The bores 890 are arranged so that there is one cluster of three bores that are spaced apart so there is a relatively short angular distance between two adjacent bores. There is also a second cluster of three bores that are spaced are arranged so there is a larger angular distance between the adjacent bores.

Figure 55:
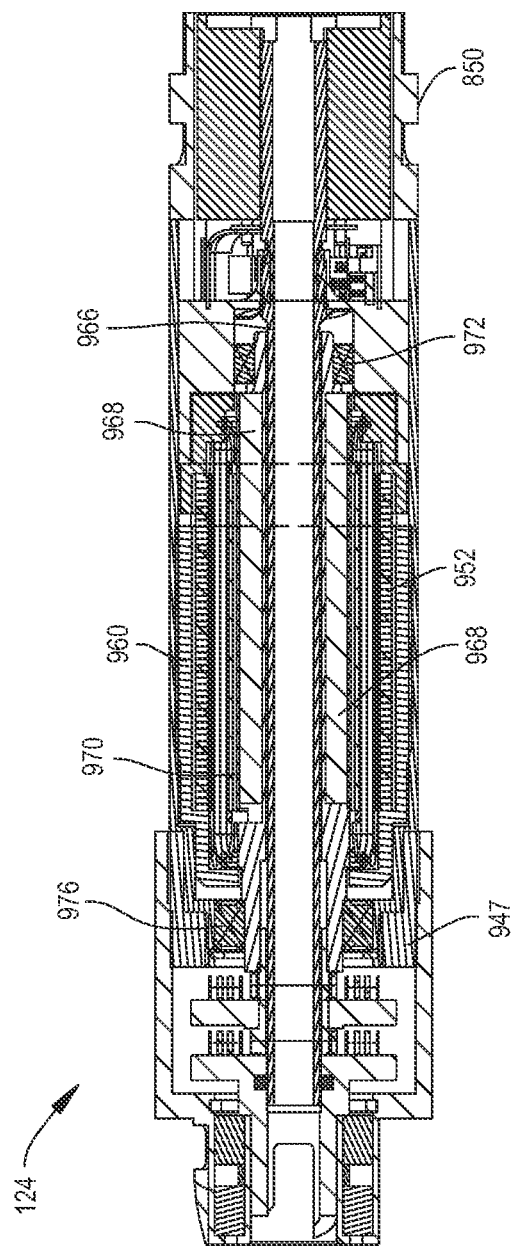
FIG. 55 is a cross sectional of the tool unit of FIG. 54.

An electrically conductive socket pin 894 or an electrically conductive socket pin 902, both seen in FIG. 55, is seated in each one of the socket bores 890. Socket pins 894 have tubular shaped heads 896. Pin heads 896 are shaped to receive in releasable press fit the BCM contact pins 350. A solid stem 898 extends forward from the distal end of each pin head 896. Each socket pin 902 has a head 904 identical to pin head 896. A stem 906 extends forward from the distal end of each pin head 902. Stems 906 are in cross section, U-shaped.

Upon assembly of the tool unit 124, the pin heads 896 and 904 are press fit in the socket bores 890. Pin head 904 are seated in the bores 896 wherein the angular distances between adjacent bores is relatively large. The components forming tool unit 124 are further shaped so the pin stems 898 extend forward a relative short distance from socket 880. Pin stems 906 extend distally forward a further distance from socket 880.

Figure 59:
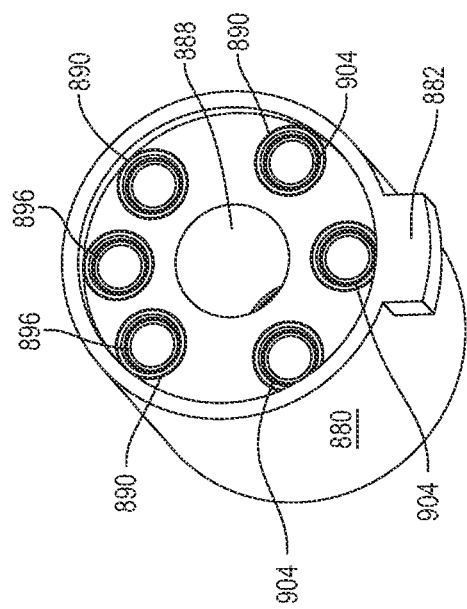
FIG. 59 is a perspective view of the socket of the tool unit of FIG. 54.
Figure 61:
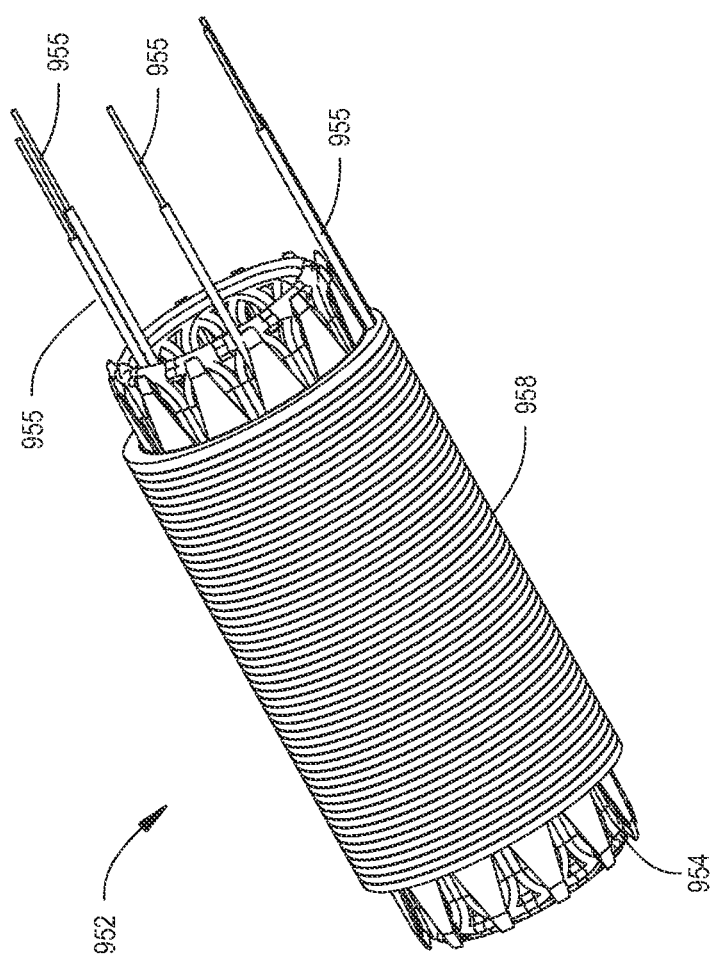
FIG. 61 is a is a perspective view of the winding of the tool power generating unit of FIG. 53.

Memory 910, as seen in FIG. 59, is attached to flex circuit 912. Flex circuit 910 is shaped to have a set of flaps. One flap, flap 914 is shaped to seat against the distally directed face of socket 880. While not identified, flap 914 is formed to have holes that are shaped to receive socket fingers 884. Socket fingers 884 thus hold the flex circuit 914 to the socket. It should further be understood that flex circuit flap 914 is disposed over stems 898 integral with socket pins 894.

Flex circuit 912 has three additional flaps, 916, 918 and 920. Flaps 916, 918 and 920 extend forward from flap 914. Memory 910 is mounted to flap 916. Mounted to flap 918 is a microcontroller 909. While not illustrated, microcontroller 909 is connected to memory 910. Microcontroller 909 is the device that, in response to commands from the BCM tool controller 530 reads data from and writes data to memory 910 is connected to microcontroller 909. While not identified, it should be understood that other components are mounted to flex circuit 912. These components include the component that protect the microcontroller 909 and memory from electrostatic discharge. One of these components is also the pull-up resistor that is connected to the BCM communications circuit 730.

Not illustrated are the conductive pads formed on the flex circuit to which the connections to pin stems 898 are made. These pads are typically located on flex circuit flap 914 Also not illustrated are the conductors formed on the flex circuit 912 that establish the various connections to the conductive pads as well as to the components on the flex circuit.

Figure 54:
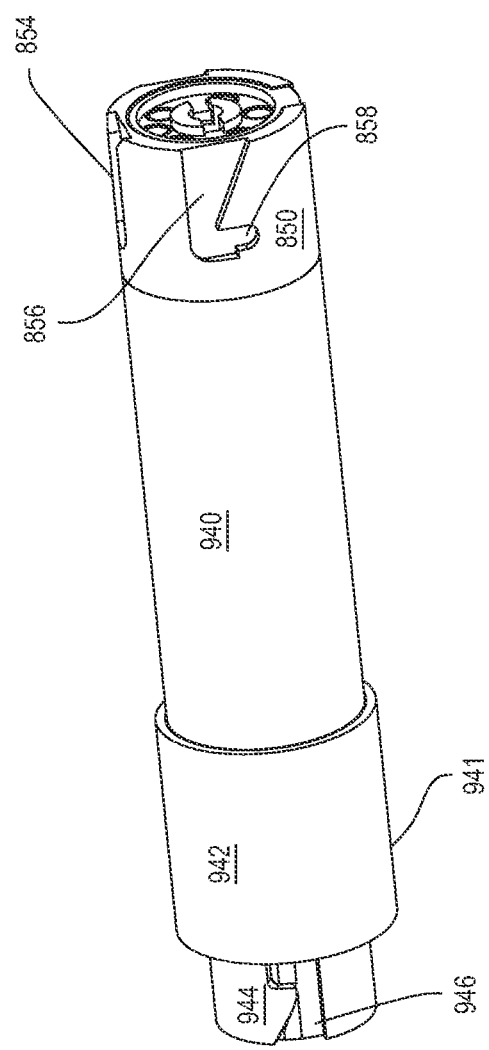
FIG. 54 is a perspective view of the power generating unit of an alternative tool unit of this invention.

From FIGS. 53 and 54 it can be seen that tool unit housing main tube 940 is generally tubular in shape. Shell 940 is, like all the exposed components forming tool unit 124 able to withstand the effects of autoclave sterilization and other sterilization processes to which tool unit 124 may be subjected. Further, shell 124 or at least a portion thereof, is formed from material through which the signal monitored by sensors 594 is able to pass without being distorted or attenuated to a level that adversely affect the operation of sensors 594. Here "adversely affect" means the ability of the sensors 594 to output sensor signals as a function of characteristics of the emitted energy is impaired. In the described embodiment, the magnetic field emitted by the motor rotor magnets 968 is the signal to be sensed that is emitted by the tool unit 124. Accordingly, in one version of the invention, shell 940 is formed from a non-magnetic material. One such material is stainless steel. Main tube 940 could alternatively be formed from plastic or a ceramic.

The proximal end of main tube 940 is open. The inner diameter of the proximal end of the shell is designed to closely receive legs 864 and head 866 of end cap 850. The distal end of the main tube 940 is formed to have a pair of inwardly stepped sections, not identified.

Distal cap 941 is formed to have a cylindrical base 942. The base 942 is shaped to fit over the inwardly stepped sections of main tube 940. Forward of base 942, distal cap 941 has a neck 944. Neck 944 has a diameter less than that of the main body of the shell 940. Two slots 946, one shown, are formed in the outer surface of neck 944. Slots 946 receive complementary fastening features integral with head 16. These fastening features facilitate the removable attachment of head 16 to shell 940.

When tool unit 124 is assembled, a fastening ring 947 is press fit over the stepped sections of main tube 940. Distal cap base 942 is threaded over distal cap base 942. Not identified is the threading around the inner surface of the distal cap base and the complementary threading around the outer surface of ring 947. Also not identified are the axially aligned bores that extend through main tube 940, cap base 942 and cap neck 944.

Figure 60:
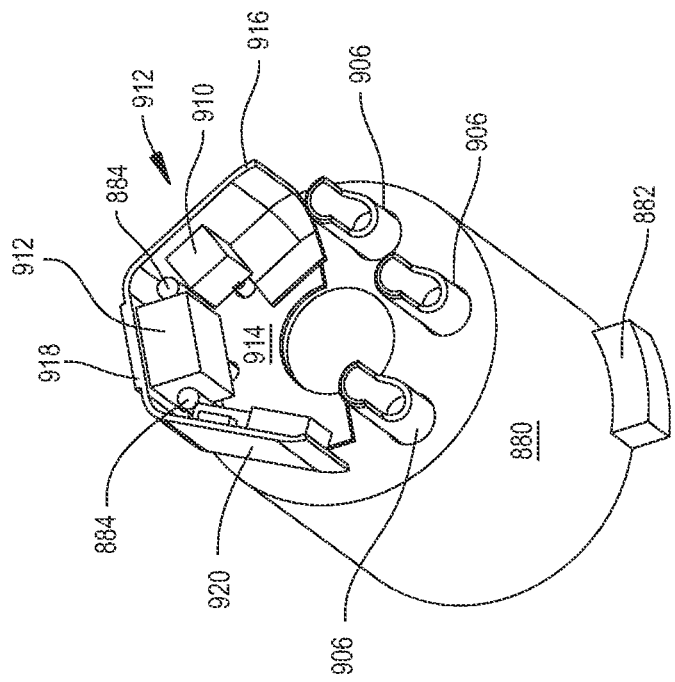
FIG. 60 is a perspective view of the distal end of the socket of FIG. 58 and the components mounted to this end of the socket.

Motor 950, the tool power generating unit, is a brushless DC motor. The motor 950 includes a stator 952 and a rotor or shaft 966. From FIG. 60 it can be seen that the wire forming three windings 954 (one identified) of the stator is wrapped around a tube like core 956. A lamination stack 958 is disposed over the windings 954. Two leads 955 extend from each winding 954. In FIG. 60, for ease of illustration, only five leads 955. One lead 955 from each of the three windings is connected to the other two leads from the other windings 954 so that the windings collectively form a Y-winding. The free lead 955 of each winding 954 is connected to the stem 906 of a separate one of the socket pins 902, (connection not shown).

In FIG. 54 it can be seen that the stator 952 is disposed in an electrically insulating sleeve 960. Sleeve 960 tightly fits in the main bore of shell 940.

In the depicted version of the invention motor rotor 966 is cannulated. A lumen, not identified, extends between the proximal and distal ends of the rotor 966. A tube 967 disposed in the lumen of the rotor 966 is statically mounted to the tool unit housing. Tube 967 has a proximal portion, not identified, that is disposed in socket bore 888. The tube 967 extends distally into the bore internal to the distal cap base 942.

Four magnets 968 (only two magnets seen) are disposed over the portion of the rotor 966 seated in the stator 952. A sleeve 970 holds the magnets 968 to rotor 966. A bearing assembly 972 rotatably holds the proximal end of the rotor 966 bore in end cap bore 872. A bearing assembly 976 rotatably holds rotatably holds a distal portion of rotor 966 to the most distal stepped section of tool unit housing main tube 940.

Not identified and not part of the present invention are components attached to the distal end of the rotor 966. These components transfer the rotational motion of the rotor 966 to the tool unit head 17.

E. Operation

Operation of powered surgical tool assembly 120 of this invention is now explained by reference to the flow chart of FIGS. 62A to 62D. Initially, as represented by step 1002, battery and control module 128 is in the hibernation state. When BCM 128 is in the hibernation state, drive controller 770 does not assert any of the signals that cause any of the power supplies that can be selectively turned on to be turned on, the only signal output be a power supply is the 3.3 Volt hibernation signal output by the 3.3 Volt power supply.

Also it should be assumed for this operating state of the BCM 128 that the switch finger tab 448 is fully retracted so as to be seated against fork 444. When the switch is so set, the proximal end of beam 472 is seated in distal shell notch 184. The seating of beam 472 in notch 184 prevents the switch from being pivoted downwards towards the shell nacelle 166. When the switch is in this state the "○" marking 480 is visible through window 457. If a tool unit 124 was coupled to the BCM 128 this would serve as an indication that the assembly 120 could not be actuated.

When the BCM is in the hibernation state, there are essentially two activities. One activity is the monitoring of ambient temperature by temperature sensor 704. The second activity is the monitoring of the WAKE_UP and WAKE_TEMP signals by drive controller 770. This means that when the BCM is in the hibernation state, relatively little current is drawn from cells 38. This means that the BCM 128, once the cells 38 are fully charged, the BCM can be left on the shelf for a period of at least 3 months and preferably at least 6 months with little concern that the current draw by the always on components will drain the cells to such a level that BCM will not be able to drive a tool unit 124 to which the BCM is attached.

When BCM 128 is in the hibernation state, MOSFET 622 and 623 are turned off. This reduces the loss of charge that would otherwise result from an output of a signal over bus 624. The turning off of MOSFETs 622 and 623 also prevents unintended charging of the cells 38.

Step 1004 represents the determination by temperature sensor 704 that the ambient temperature has exceed the set trip temperature level. This event results in the temperature sensor 704 connecting the sensor input pin to which the 3.3 Volt hibernation signal is ground. The voltage on the bus connected to this pin is thus pulled low. The signal on this bus serves as both the WAKE_UP and WAKE_TEMP signals. Thus both of these signals, which are asserted LOW, are applied to the drive controller 770.

In response to the drive controller 770 receiving both the WAKE_UP and WAKE_TEMP signals, the controller recognizes that the BCM is most likely being sterilized. The BCM thus enters a data logging state, represented by step 1006. In the data logging state, the drive controller, asserts the 3.3_WAKE signal. The resultant turning on of MOSFET 538 results in the drive controller 770 being sourced enough current that it can record data regarding the time at which the BCM is at a temperature above the trigger level. Drive controller 770, as part of this data logging, may also record data identifying the temperatures of the BCM 128. These data are based on the signals representative of these temperatures supplied by temperature sensor 704. These data are available for later review by the persons responsible for maintenance of the BCM. These data are used to determine whether or not the BCM was subjected to an appropriate sterilization procedure.

After sterilization, the BCM 128 is returned to a room temperature environment, appx 22° C. Eventually the temperature of the BCM drops to that of this environment. Once BCM temperature falls to a level below a return temperature level, temperature sensor 704 opens the connection between the pin to which the 3.3 Volt hibernation signal is asserted and ground, (step not shown). This results in the BCM returning to the hibernation state. This results in the negation of the 3.3_WAKE signal.

Periodically, either the BCM 128 is attached to a charger or a tool unit 124 is fitted to the BCM. In either event, the BCM contact pins 350 seat in the complementary socket pins of the device to which the BCM is attached. Given the structure of the BCM it should be appreciated that the contact pins 350 are able to slightly move relative to the BCM housing. The ability of the contacts pins 350 to so move reduces the amount of mechanical stress to which the pins are exposed as part of this pin-in-socket coupling process. The reduction of this stress result in a like reduction in the extent to which this stress can result in pin bending or breakage.

Step 1008 represents the evaluation by the drive controller 770 regarding whether or not the BCM is attached to a tool unit or charger. It is understood that step 1008 is part of the evaluation process performed during the temperature trigger level exceeded determination of step 1004.

When either the BCM 128 is seated over the charger or the tool unit 124 is seated in the BCM, the housing of the charger or tool unit seats against ribs 216 internal to BCM bore 214. This ensures the device in the bore 214 remains physically static within the bore while minimize the amount of physical force required to disconnect the BCM 128 from the attached device.

While not illustrated it should be understood that the charger to which the BCM 128 is attached has a low resistance relative to resistor 708. It should also be understood that the charger sources a low level current out of the charger socket pins that are connected to the contact pins 350 to which MOSFETs 628 and 630 are connected. Internal to the tool unit 128 there is a like low resistance path between the socket pin 894 to which the DEV_PWR signal is applied and ground.

As long as the BCM 128 is not connected to a charger or a tool unit 124, the 3.3 Volt hibernate signal applied to the junction of resistor 708 and diodes 710 and 712 remains at or near this level.

For the reasons set forth above, when the BCM 128 is connected to either the charger or a tool unit 124, a low resistance path to ground is established between the junction of resistor 708 and diodes 710 and 712. This causes the signal at this junction to fall to ground. This signal is the asserted LOW WAKE_UP signal. At this time diode 710 prevents the signal present at the junction of temperature sensor 704 and resistor 706 from likewise falling to ground. Accordingly, when the BCM is in this state, wake up circuit 702 does not assert the WAKE_UP signal. Drive controller 770 in step 1008 thus interprets the receipt of the WAKE_UP signal without the simultaneous receipt of the WAKE_TEMP signal as an indication that the BCM 128 is attached to either a charger or a tool unit 128.

In a step 1010 drive controller 770 then determines if the BCM is connected to charger or a tool unit 124. This evaluation is made by monitoring the states of the BCM_CHRG signals. If the BCM is attached to a charger the low-level 1 charging current will be present on the contact pins 350 to which this current is applied. These currents are applied to the resistors 714. The currents thus appear as the asserted HIGH BCM_CHRG signals. In contrast, when the BCM is attached to the tool unit 124, the BCM initially does not source currents to these pins 350. Accordingly, when a tool unit 124 is attached to the BCM 128, immediately after the WAKE_UP signal is asserted, the BCM_CHRG signals are not present. Drive controller 128 thus bases the determination of step 1010 based on the whether or not the BCM_CHRG signals are asserted.

The fault state of less than all the BCM_CHRG signals being asserted is not material to the main operation of this invention. The operation of the BCM 128 when the signals indicate faults such as this are therefore only minimally, if at all, described.

If the BCM is attached to a charger, the BCM enters a pre-charging state represented by step 1012. When in the charging state, drive controller asserts the 3.3_WAKE signal and the 5V_ENB signal, the C/D_ENB signal and CHR_ENB signal. The assertion of the 3.3_WAKE signal results in power supply 534 outputting the 3.3 Volt 3.3 Volt analog signals. The assertion of the 5V_ENB signal results in power supply 548 outputting the 5 Volt and 5 Volt analog signal.

When in the pre-charging state, the drive controller 770 determines if the BCM 1278 can accept a charge from the charger to which the BCM is attached, step 1014. This evaluation may include running some checks on the components of tool controller 530. This evaluation may also involve an exchange of data signals with the charger to ensure that the charger can charge the BCM. As these evaluations are not part of this invention they are not discussed further. If it is determined that the BCM cannot be charged, the BCM enters a fault state, step 1016.

If the BCM 128 can be charged, the BCM enters a charging state 1018. The BCM enters the charging state by outputting the square wave to the voltage doubler 642 and the assertion of the C/D_ENB and CHRG_ENB signals. The outputting of the square wave causes the voltage doubler to output a signal with sufficient high potential to turn on MOSFETs 622, 623 and 628. The C/D_ENB signal is asserted LOW. The assertion of the C/D_ENB signal thus results in the turning off of MOSFET 646. The turning off of MOSFET 646 results in the output signal from the voltage doubler being applied to the gates of MOSFETs 622 and 623 and the source of MOSFET 650. The turning on of MOSFETs 622 and 623 results in the connection of the BAT+ terminal of the cells to bus 624.

The asserted CHRG_ENB signal is applied to the gate of MOSFET 654. This results in the turning off of the MOSFET 654. The signal present at the gate of MOSFET 650 is thus pulled to ground. This results in the turning on of MOSFET 650. This results in the high potential signal from voltage doubler 642 being applied to the gate of the MOSFET 628 to which the drain of MOSFET 650 is connected. This results in the turning on of the MOSFET 628. The turning on of this MOSFET 628 establishes a low resistance path from the contact pin 350 to which the MOSFET 628 is connected and the positive terminal of the cells 38. This is the path over which the charging current is sourced to the cells.

In the absence of MOSFET 650 being turned on, there would still be a current flow through the MOSFETs 628 to the cells 38. This current flow is through the body diodes of the MOSFETs 628. This is because while not shown in the drawings it is understood that MOSFETs 628 are arranged so that their body diodes are forward biased between the resistors 631 and resistor 626. However, there is a voltage drop of approximately 0.7 Volts across these body diodes. The turning on of one of the MOSFETs 628 results a conductive path with a lower voltage drop being established between one of the contact pins 350 and the cells 38. This results in a more efficient charging of the cells.

There will also be current flow from the charger to the cells through diode 632. Diode 632 is provided in the event the cells are fully discharged. If the BCM 128 is in this state, it is understood that tool controller 530 does not function. While not depicted in the flow charts, it should be understood that when the BCM 128 is in this state and attached to a charger, there will be at least some current flow through diode 632. This current flows through the body diode of MOSFET 623. The current is then available to energize the 3.3 Volt power supply 534, (connection from MOSFET 623 to and power supply 534 not shown). The subsequent outputting the 3.3 Volt hibernation signal by power supply 534 reactivates drive controller 770. Tool unit controller 530 then cycles the BCM 128 from the hibernation state to the state in which the BCM recognizes that the BCM is attached to a charger.

The CHR_ENB signal is also applied to level shifter 636. The application of the CHR_ENB signal to the level shifter 636 disables the shifter. This ensures that, during charging an errant signal will not be applied to the gate of one of the MOSFETs 630. If this event was to occur, the cells 38 would be tied to ground.

While the BCM 128 is in the charging state, drive controller 770 continually monitors the other components of the tool unit controller 530 to determine if the BCM is attached to the charger 530, step 1020. This monitoring may be performed by monitoring the contact pins 350 over which the charging current source to determine if the BCM_CHRG signal changes state. Specifically, the disconnecting of the BCM 128 from the charger result in the transition of the BCM_CHRG signal to the low state. Alternatively, the signal across the contact pin 732 to which the voltage regulator is 532 is attached may be powered. The removal of the BCM 128 from the charger would thus result in the WAKE_UP signal, which is asserted LOW, from transitioning to the HIGH state.

Once in step 1020 it is determined that the BCM 128 is withdrawn from the charger, drive controller 770 returns the BCM to the hibernate state. This results in the negations of the signals that were asserted to place the BCM in the charging state.

Returning to step 1010 it should be understood that when a tool unit 124 is attached to the BCM 128 the will be no signals on the contact pins 350 from which the BCM_CHRG signals are obtained. Drive controller 770 then places the BCM 128, at this time the whole of the tool assembly 120, in the tool attached state, step 1026. The drive controller 770 places the assembly 120 in the tool attached state by asserting the 3.3_WAKE and 5V_ENB signals.

The TU_ENB signal is also asserted to voltage regulator 732. The assertion of the TU_ENB signal results in voltage regulator 732 supplying the DEV_PWR signal to the tool unit microcontroller 909 (step not shown). In a step 1028, the BCM drive controller 770 exchanges data with the tool unit 124. This includes the reading of data in tool unit memory 910. As part of this step, the drive controller 770 may write data to memory 910. These data include data logging into the tool unit memory 910 the date/time of the connection and identifying data specific to the attached BCM 128.

Drive controller 770 then determines if the BCM is capable of energizing the tool unit 124, step 1030. One or more evaluations are performed in step 1030. These evaluations include: determination if the tool unit provides a correct authorization key; determination of whether or not the tool unit provide data indicating it was sterilized; or a determination that the tool unit has not stored data indicating that the unit itself is in a fault state. If in step 1030, drive controller 770 determines that the BCM 128 cannot energize the tool unit 124, the drive controller places the assembly 120 in a fault state, step 1032. Drive controller 770 may inform the practitioner that the assembly 120 is in the fault state by rapidly cycling one or more of LEDs 752 and 766 on and off, (step not shown).

If in step 1030 it is determine that the BCM can energize the tool unit 124, the drive controller 770 places the assembly 120 in the ready state, step 1036. Specifically at this time the TRG_ENB signal is asserted. The assertion of the TRG_ENB signal results in the turning on of MOSFET 562. The 3.3 Volt analog signal is applied to sensor 566. Sensor 566 is then able to generate a variable signal as a function of the displacement of trigger 440.

The practitioner completes the process of readying the assembly for use by extending trigger beam 472 and finger tab 488 from fork 444. This moves the proximal end of beam 472 out of the notch 184 internal to the distal end shell 162. One or both of the "|" markings 478 and 482 should then be visible. The practitioner is then free to turn on the assembly 1030 by pressing down of finger tab 488.

Step 1038 represents the determination of whether or not the practitioner has actuated the assembly 120. This determination is made by monitoring the ANA_TRG signal. Specifically, the downward depression of the trigger 440 by the practitioner changes the distance between magnet 490 and sensor 566. This results in a change in the voltage of the ANA_TRG signal.

Once the change of the ANA_TRG signal is above a hysteresis level, tool unit controller 530 energizes the tool unit power generator 950, step 1040. Initially, in step 1040 drive controller actuates the voltage doubler 642 and asserts the C/D_ENB signal. This results in the application of voltages to the gates of MOSFETs 622 and 623 that turn on the MOSFETs.

The MTR_SNS_ENB signal is also asserted. This results in the application of the 3.3 Volt analog signal through MOSFET 592 to sensors 954.

Also in step 1042, the BCM 126 sources the energization signals to the tool unit power generating unit 950. Since this particular power generating unit 950 is a brushless DC motor, step 1042 involves the selective tieing of the motor windings 954 to either the BAT+ or BAT− terminals of the cells 38. This process is performed by the selective turning on and off of MOSFETs 628 and 630. Drive controller 770 thus asserts the appropriate sequence of D_CNTRL signals to level shifter 636. Level shifter 636 and gate drivers 638 collectively assert the signals to the gates of MOSFETs 628 and 630 to ensure the appropriate application of commutation currents to motor windings 954.

Drive controller 770 applies commutation currents to windings 954 as a function of the rotational position of motor rotor 966. The drive controller 770 determines rotor position as a function of the output signals from sensor 594.

Specifically, each sensor 954 outputs its sensor signal as a function of the strength of the magnetic field sensed by the sensor. More specifically these are magnetic fields emitted by rotor magnets 968. FIG. 63 is a plot of the three TU_SNSx signals, signals 1044a, 1044b and 1044c for a complete 360° of the magnetic rotation of the rotor 966. Each signal 1044a, 1044b and 1044c is generally sinusoidal. Owing to the positioning of the sensor 594 relative to the motor rotor 966, each signal is essentially 60° out of phase with the adjacent signal.

In step 1040, drive controller 770, at any given instant in time, uses the linear segment of a single one of sensor signal 1044a, 1044b or 1044c, as the signal representative of rotor rotational position. In FIG. 63 the two bold phases of each signal are the linear portions of the signal. This is because when a sensor signal is in one of the signal's linear phases, that signal is highly correlates to the rotational position of the rotor. Once one of the sensor signals leaves its linear phase it can be seen that signal output by one of the adjacent signals will enter its linear phase. Accordingly, at this time the drive controller 770 bases the determination of rotor rotational position based on this second sensor signal 1044a, 1044b or 1044c. Three sensors 594 are used because over 180° of the magnetic rotation of the rotor each sensor provides a signal that highly correlates to the rotor position for 60° of rotor rotation. In the described version of the invention motor 950 has four magnets 966 and is a two pole pair rotor. Accordingly, 360° of magnetic rotation correspond to 180° of physical rotation. Thus for every 360° of physical rotation of the rotor 966 the signal from each sensor 594 is used in four different phases of that 360° to determine rotor rotational position.

Accordingly, based on the sequence of sensor signals 1044a, 1044b and 1044c, drive controller 770 determines the rotational position of the motor rotor 966. Based on rotor position the commutation currents are sourced to and sunk from the appropriate set of windings. It should be understood that in some versions of the invention, tool unit controller 530, when sourcing the commutation current, may source the current to two of the windings. This would result in two of the MOSFETs 628 being simultaneously turned on. The commutation currents are sunk from at least one of reminding windings 954, the windings to which the current is not being sunk.

The frequency with which the commutation current is applied and the duty cycle with which the commutation current is applied are further of the extent to which the practitioner actuates switch 440. Thus, tool unit controller 530 in addition to controlling the on/off state of the power generating unit 950 is further able to control the rate of operation, here motor speed. This speed is set based on the level of the ANA_TRG signal from sensor 566.

Tool unit controller 530 sources energization signals to the power generating unit 950 in part based on the data read from tool unit memory 910. For example, these data may include calibration data for determining rotor rotational position based on the characteristics of the individual magnets 966. These data may indicate the maximum currents that should be applied to the windings and the maximum voltages that should be allowed to develop across the windings. These data may also indicate the maximum torque the motor should be allowed to develop (equivalent to current draw) for a given motor speed. Drive controller 770 uses these data as well as the WNDGx_I signals representative of winding current draw and the WNDGx_V signal representative of winding voltages to further regulate the sources of the energization signals to the motor 950.

Figure 62A:
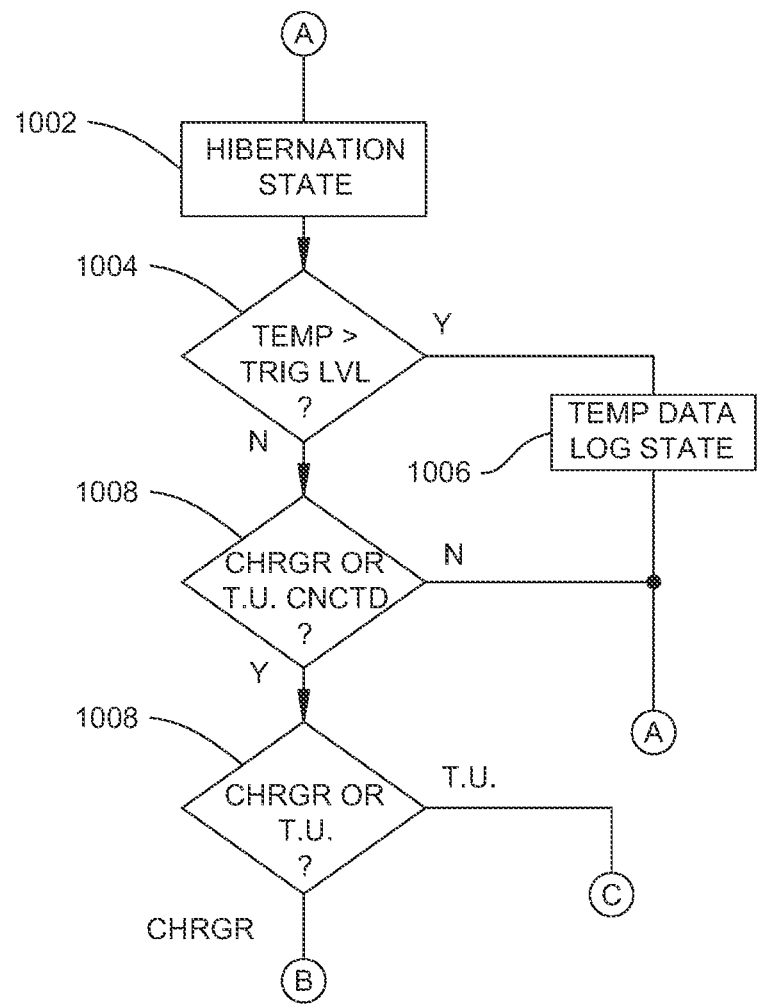
FIGS. 62A-62D, form a flow chart of the major steps performed to operate the surgical tool assembly of this invention.
Figure 62B:
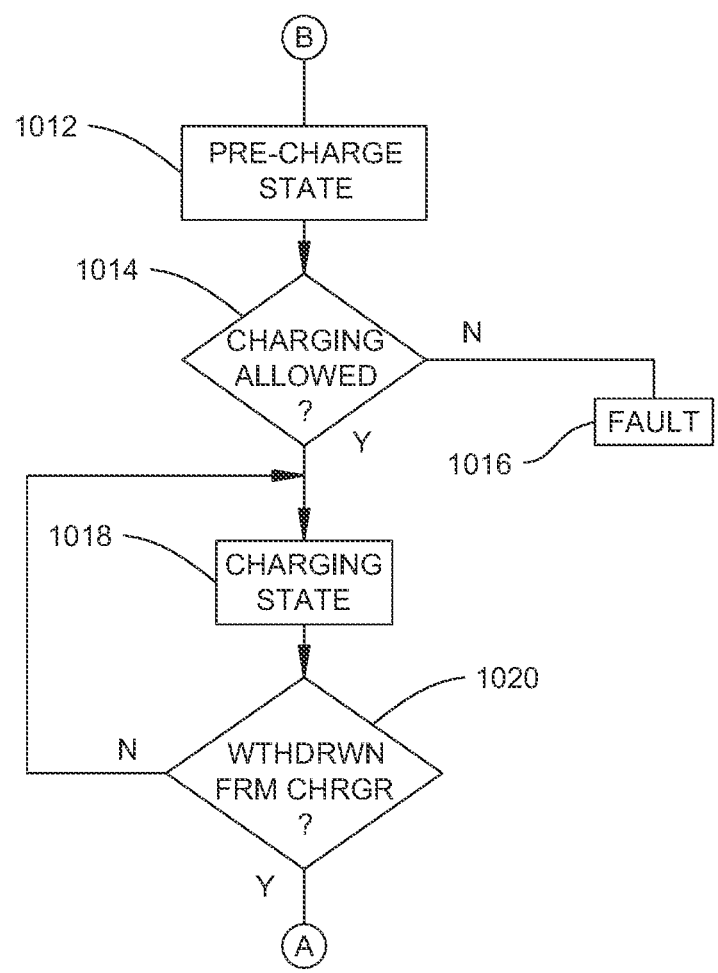
Figure 62C:
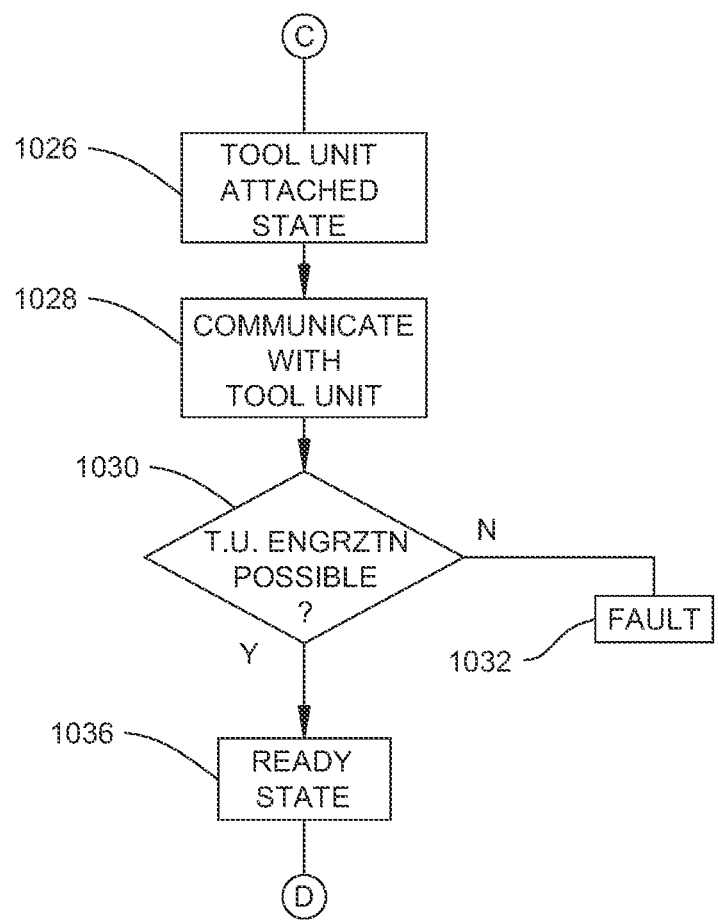
Figure 62D:
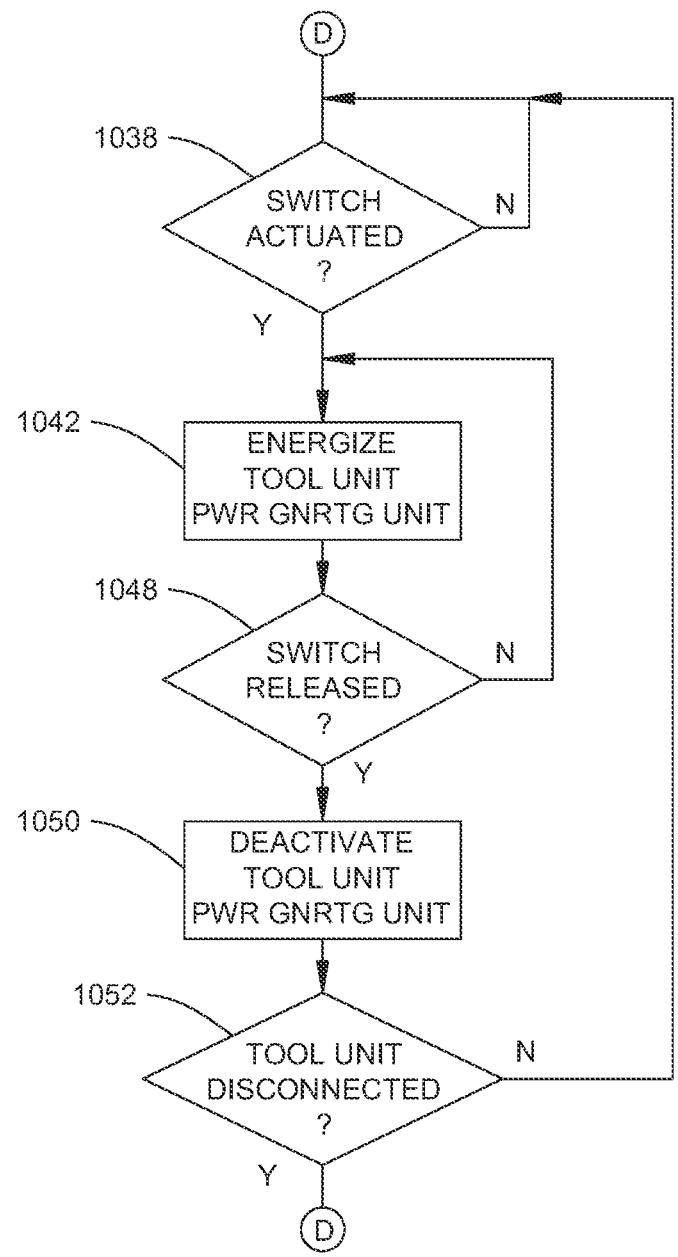

The BCM 128 provides energization signals, here commutation currents, to the tool unit power generating unit as long as the trigger 440 is depressed, switch released step 1048 of FIG. 62D. Once use of the assembly 120 is no longer required, the practitioner releases the force applied to the trigger switch 440. Springs 496 return the switch to the off position in which magnet 490 is spaced furthest from sensor 566. Once tool controller 770 determines the ANA_TRG signal has returned to the off state signal level, the controller negates the application of the C/D_ENB and D_CNTR signals. The application of commutation currents to the windings is thus terminated, step 1050.

As represented by step 1052, tool unit controller 530 also determines whether or not the tool unit has been disconnected from the motor. This evaluation may be monitoring communication between the BCM drive controller 770 and the tool unit microcontroller 909. This is because, while not shown as an explicit step, the drive controller 770 may repeatedly send an inquiry to the microcontroller 909 requesting that the microcontroller 90 send an acknowledgement. If these acknowledgments are not received for a defined period of time, for example, for a period typically less than 2 seconds, drive controller 770 assumes that the tool unit has been removed from the BCM. Alternatively using circuit components not illustrated, the drive controller 770 monitors the current drawn by the tool unit components over the power line connected to these components. A drop of this current draw is interpreted by the drive controller 770 in step 1052 that the tool unit has been disconnected from the BCM 128.

Regardless of the type of test, once the drive controller 770 determines that the tool unit has been disconnected, the Drive controller returns the BCM to the hibernate state. As part of this transition, the signals that are asserted to place the assembly in the drive controller 770 in the ready state are negated.

The assembly 120 of this invention has a weight of less than 0.6 kg and more preferably less than 0.4 kg. The assembly is with, at least 25% of the overall length of the tool unit 124 being encased in the BCM housing is designed to be held in a single hand like a pencil or a pen.

A feature of assembly 120 of this invention is that the overall length of the tool unit 124, excluding the energy applicator 17, is generally between 10 to 15 cm. The assembly 120 is further designed so that when the tool unit 124 is seated in the BCM 128, one of the cells 38 is disposed over a proximal section of the tool unit that is approximately 2 to 7 cm in length. Owing to the weight of the individual components, tool assembly 120 thus tends to have a center of gravity that is located approximately 5 to 8 cm proximal from the distal end of the tool unit head 16 and more often 6 to 7 cm. This means that when a practitioner using the tool holds the tool between the thumb and middle finger, the center of gravity of the tool tends to be approximately 6 cm of where the thumb and forefinger meet on the hand. Thus the weight of the tool is born primarily by this part of the hand. This serves to reduce the ergonomic stress imposed on the thumb and finger that is holding and manipulating the assembly.

It is still a further feature of this invention that the contact pins 350 through which the H-bridge sources current to and sinks current from the tool unit power generating unit 950 are the contacts through which the charger sources currents to the cells 38. This eliminates the need to provide the BCM of this invention with a contact the sole purpose of which is to receive the charging current.

III. Third Embodiment

Figure 65:
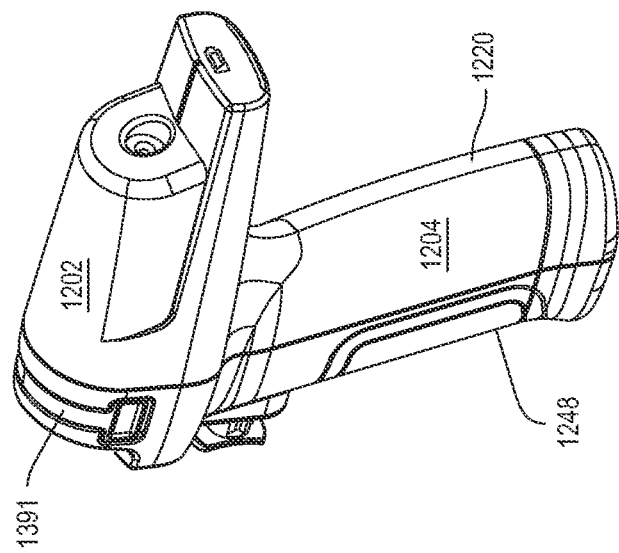
FIG. 65 is a perspective view of the proximal facing portion of the BCM of FIG. 64.
Figure 64:
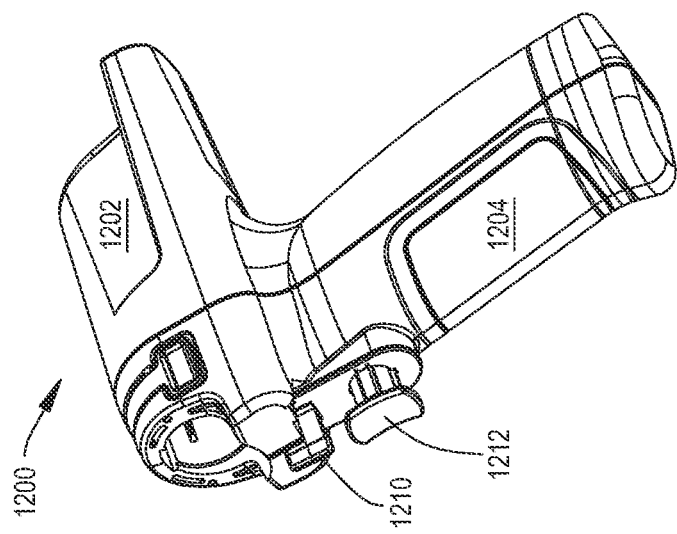
FIG. 64 is a perspective of the distal facing portion of an alternative battery and control module of the assembly of this invention.
Figure 66:
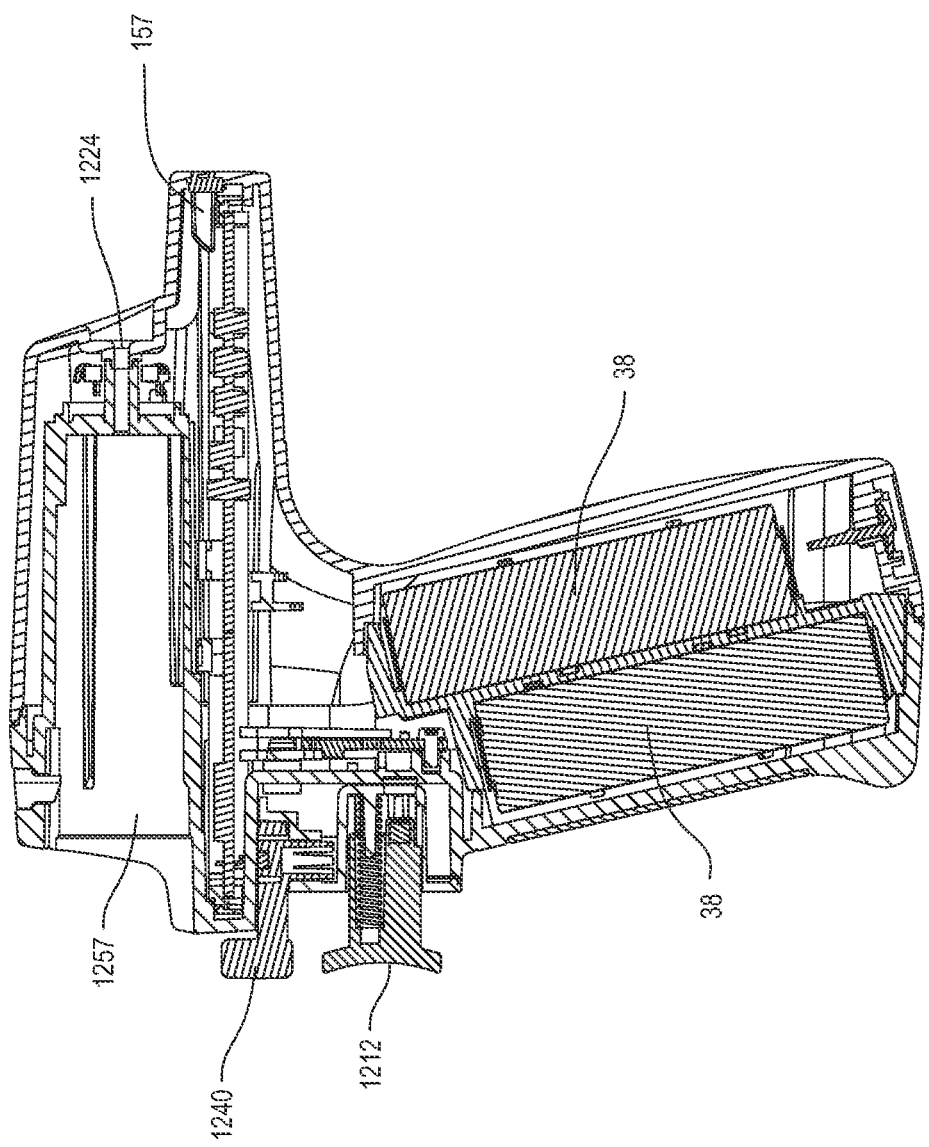
FIG. 66 is a cross sectional view of the battery and control module of FIG. 64.

FIGS. 64-66 depict the basic structure of an alternative battery and control module 1200 of this invention. Battery and control module 1200 has a housing or body that is pistol shaped. Thus the housing includes an approximately shape barrel 1202. The housing has a grip portion 1204 that extends downwardly from the barrel. Internal to the barrel 202 is the nacelle 1256 in which the tool unit, such as tool unit 124, is releasably seated. Rechargeable cells 38 for energizing the tool unit 124 are disposed in grip portion 1204.

Battery and control module 1202 has two control switches. Both switches extend forward from the distally directed portion of the housing grip portion 1204. A first switch, switch 1210 is a toggle switch. The practitioner sets the position of switch 1210 to control the operating mode of the attached tool unit. The second switch, switch 1212, is located below switch 1210. Switch 1212 is a biased switch. The practitioner selectively displaces switch 1212 to both control the on/off state of the tool unit power generating unit and the operating rate of the power generating unit. A tool unit controller 1290 is disposed in barrel 1202 and the handgrip 1204. The tool unit controller 1290 includes the previously described sensors 566, 580 and 594. Based on the signals output by sensors 566, 580 and 594, the tool unit controller 1290 sources and sinks current to the tool unit power generating unit.

Figure 68:
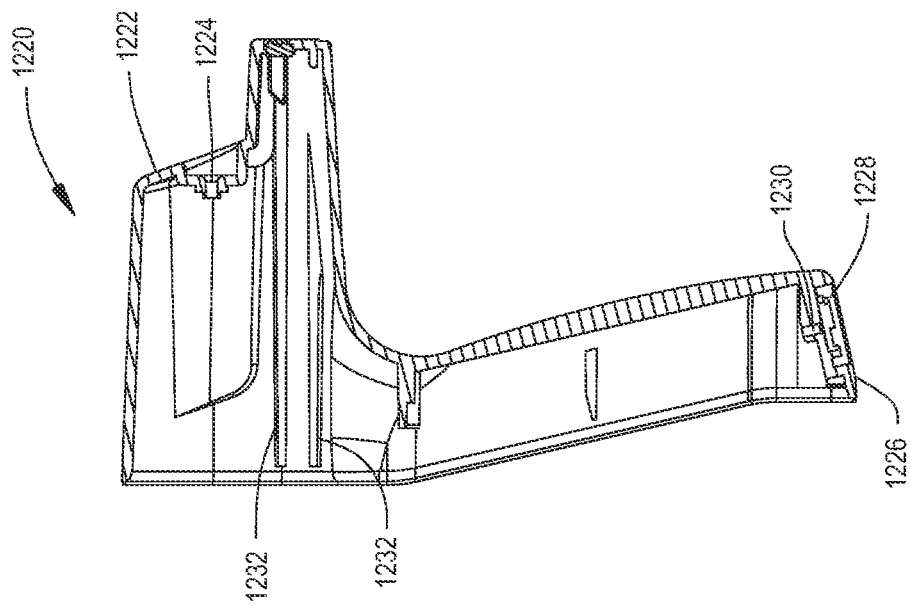
FIG. 68 is a cross sectional view of the proximal shell of FIG. 67.
Figure 67:
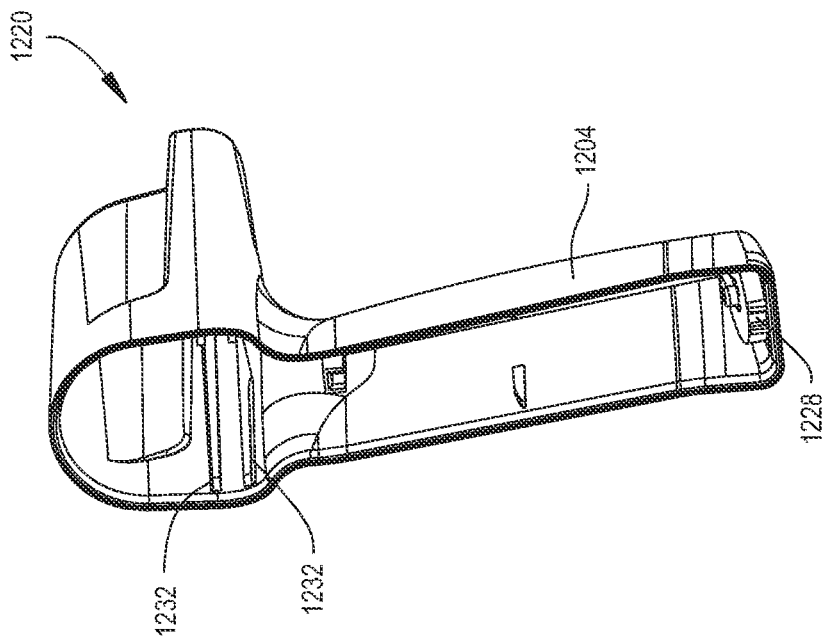
FIG. 67 is a perspective view looking into the open distal end of the proximal shell of the battery and control module of FIG. 64.
Figure 70:
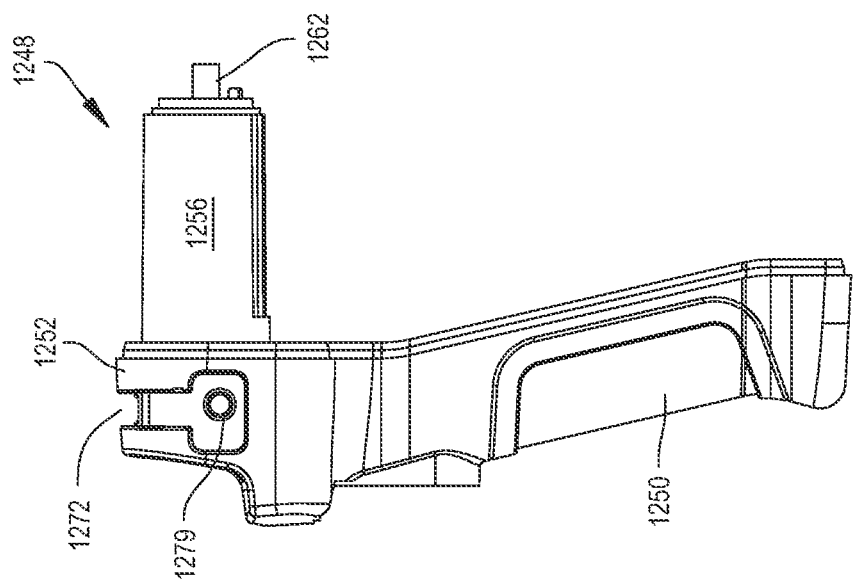
FIG. 70 is a side plan view of the distal shell of FIG. 69.
Figure 69:
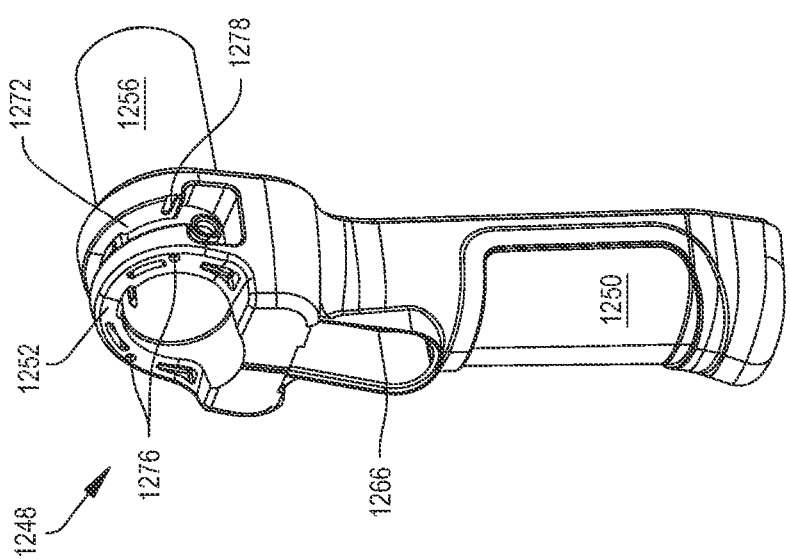
FIG. 69 is a perspective view of the distal shell of FIG. 64.
Figure 72:
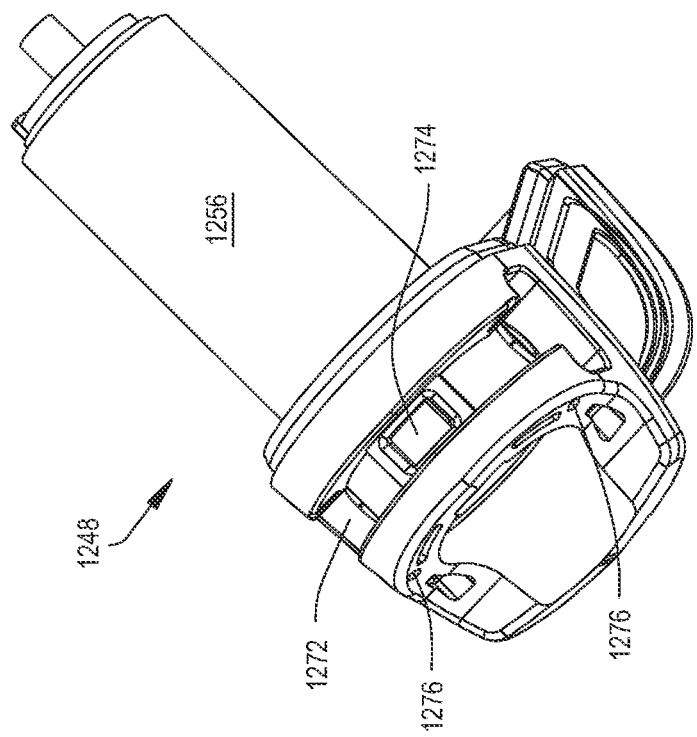
FIG. 72 is a perspective view of looking into the open proximal end of the distal shell of FIG. 69.
Figure 71:
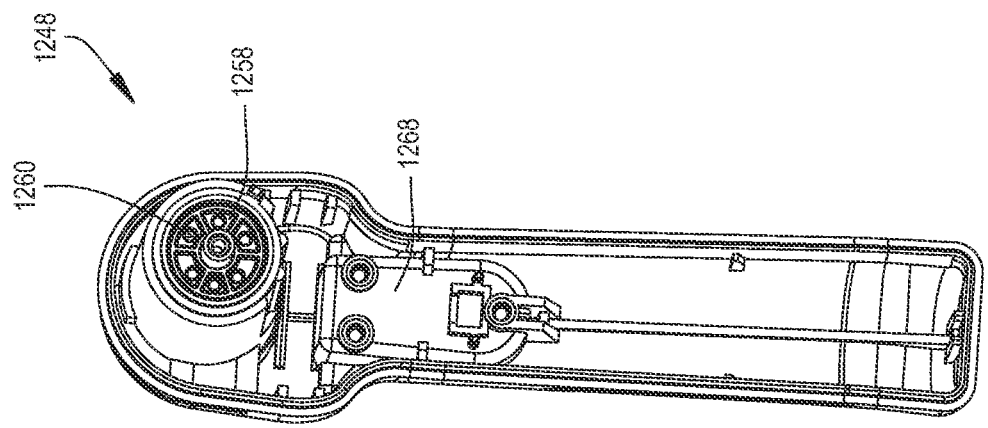
FIG. 71 is a perspective view of the top of the distal shell of FIG. 69.

The housing of BCM 1200 is formed from a proximal shell 1220 and a distal shell 1248. Proximal shell 1220, as now described by reference to FIGS. 67 and 68, comprises approximately three-quarters of the BCM barrel 1202 and approximately one-half of the hand grip 1204. Proximal shell 1220 has an end plate 1222 that forms the proximal end of the barrel 1202. End plate 1222 is formed with a through bore 1224. Bore 1224 is present because one type of tool unit that may be attached to BCM 1200 is a wire driver. As its name implies, a wire drive is used to drive, advance wire. The wire is feed into the cannulated rotor of the wire driver through bore 1224. Not identified is the step formed in the end plate 1222 in which bore 1224 is formed.

At the end of the grip portion 1204 of proximal shell 1220 the shell has a base plate 1226. The base plate 1226 is formed with protruding ribs 1228 and a through hole 1230. Ribs 1228 and hole 1230 are provided to facilitate the seating of pressure relief valve 154 in the base plate 1226. Two ribs 1232 extend inwardly from each of the opposed inner surfaces of proximal shell 1220. Ribs are located in the portion of the shell that defines the bottom of the barrel 1202. Ribs 1232 suspend the tool unit controller 1290 in the void space internal to the BCM 1200.

The distal shell 1248 as seen in FIGS. 69-72 is shaped to mate over the open distal end of proximal shell 1220. The distal shell 1248 is formed to have a base 1250 that is approximately semi-circular in shape. Base 1250 forms the front portion of the BCM handgrip 1204. A head 1252 is formed integrally with and is located above the top of base 1250. Head 1252 forms the distal portion of BCM barrel 1202.

The nacelle 1256 is formed integrally with distal shell 1248. The main body of nacelle 1256 is tubular in shape. Shell 1248 is formed so that the nacelle 1256 extends inwardly from the front of the shell and is located inwardly from the portions of the shell that define the outer sections of the BCM housing. Nacelle 1256 defines the bore 1257 internal to BCM 1200 in which the tool unit is received At the proximal end of the nacelle 1256 there is a disc shaped end plate 1258. End plate 1258 is structurally similar to disc 206 of BCM 128. End plate 1258 is formed with openings 1260 (one opening identified) for receiving the contact pins 350 that provide the electrical connections to the tool units and chargers to the which the BCM 1200 is attached. The proximally directed face of end plate 1258 is provided with the same rib structure with which disc 206 is formed (ribs not identified). When BCM is assembled, seal 360 and cap 370 are fitted against the proximal end of plate 1258. Seal 360 and cap 370 form the barrier between plate 1258 and the contact pins 350 seated in the plate needed to seal the void space internal to the BCM from the ambient environment. For ease of illustration, contact pins 350, seal 360 and cap 370 are not illustrated in the drawings depicted BCM 1200.

End plate 1258 is further formed to have boss 1262 that extends outwardly from the proximally directed face of the plate. Boss 1262 is formed with a through bore that extends axially through the boss and through the plate. When BCM 1200 is assembled, the proximally directed face of boss 1262 abut and is sealed against the adjacent distally directed surface of the proximal shell 1220 that defines the end of bore 1224. This establishes a channel through the housing that is isolated from the void space in the housing through which the wire can be feed into a wire driver-type tool unit.

Returning to FIG. 36 it is noted that seal 350 has center located through hole 362. From FIG. 37 it is understood that cap 370 has a like through holes 372. Through holes 362 and 372 are provided to facilitate the seating of, respectively, the seal 360 and the cap 370 around boss 1262.

Distal shell 1248 is further formed to have a set of interior located panels that define a recess 1266 that extends inwardly from the distally directed face of shell base 1250. Recess 1266 is located a short distance below shell head 1252. The recess 1266 is generally in the form of a truncated oval wherein the topped curved end of the oval is not present. In the Figures the only recess defining panel that is identified is an end panel 1268. End panel 1268 defines the proximal closed end of recess 1266.

Shell head 1252 is formed so as to have an arcuately shaped recess 1272. Recess 1272 extends inwardly from the top of head 1252 and is located proximally inward from the distal face of the head. The recess 1272 is generally semi-circular. The ends of the recess 1272 are, however parallel to each other. Further, shell 1248 is shaped so the parallel ends of recess 1272 have proximal-to-distal widths that are long the width of the main arcuate portion of the recess.

The panel of shell 1248 that forms the base of recess 1272 is shaped to define a rectangular opening 1274. Opening 1274 opens into the void space with nacelle 1256. Two through bores 1276 extend inwardly from the front face of head 1252. Each bore 1276 opens into recess 1276. Bores 1276 it should be understood are located on opposed sides of shell head 1252. The distal shell 1248 is further formed to have two notches 1278. Each notch 1278 extends inwardly from the inner panel of the shell 1248 that defines the proximal end of recess 1276. A proximal extension of each axial line through each bore 1276 intersects the base of the adjacent notch 1278. Ring 1279 (one shown) extend outwardly from the panel that defines the base of recess 1272. There are two rings 1279. Each ring 1279 is located in the wide portions at the ends of the recess 1272.

Not identified are the features internal to distal shell 1248 that facilitate the holding of tool unit controller 1290 in the shell. A number of these features are similar to the features that hold the chassis 242 in BMC 128.

Tool control unit 1290 of BCM 1200 includes a chassis 1292 to which two circuit boards 1310 and 1312 are attached. Chassis 1292 includes un upper frame 1294 and a lower frame 1302. As chassis frames 1294 and 1302 are generally similar in structure and function to chassis frames 246 and 296, respectively, frames 1294 and 1296 will not be described in detail. It will however be noted that upper frame 1294 is formed with a web 1296 that has an approximately concave surface. Three notches 1298, (two notches identified) are formed in the web. Notches 1298 are the spaces in which sensors 594 are disposed. Lower frame 1302 is formed to have two legs 1304. Legs 1304 extend perpendicularly downward from the side beams of frame 1302. Legs 1304 are formed with opposed notches 1306 (one notch identified) that face each other.

Circuit board 1310 is sandwiched between upper frame 1294 and lower frame 1302. Circuit board 1310 is held in position between frames 1294 and 1302 in the same general manner in which 296 in the same circuit board 244 is held between frames 246 and 296. Circuit board 1312 is held in position by legs 1304 integral with the lower frame 1302. More particularly the opposed top-to-bottom side edges of circuit board 1312 are disposed in notches 1306 internal to legs 1304.

When BCM 1200 is assembled, the chassis is positioned so that the main portion of the chassis 1292 and the attached circuit board 1312 are located in the barrel portion of the housing void space. More specifically the chassis is positioned so that the sensor supporting web 1296 is located below nacelle 1256. The chassis 1292 is further positioned so that circuit board 1312 is located immediately proximal to shell panel 1268.

Switch sensors 566 and 580 are mounted to circuit board 1312. Sensor 566 is positioned to be the closer of the two sensors to switch 1212. Sensor 580 is the closer of the two sensors to switch 1210.

Disposed on circuit board 1312 are the tool unit controller 1290 components that, in response to the signals emitted by sensors 566, 580 and 594 selectively apply energization signals to the tool unit power generating unit. These are the signals (currents) sourced out over and sunk back into the contact pins. As these components are generally identical to the components of tool unit controller 530, they are not redescribed.

Figure 76:
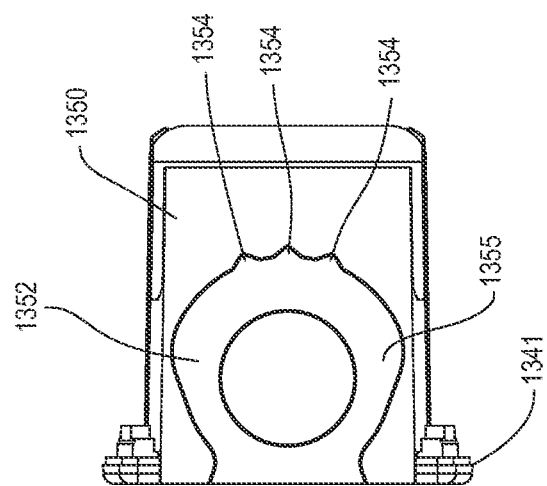
FIG. 76 is a top plan view of the top of the switch housing of the switch assembly of FIG. 75.
Figure 75:
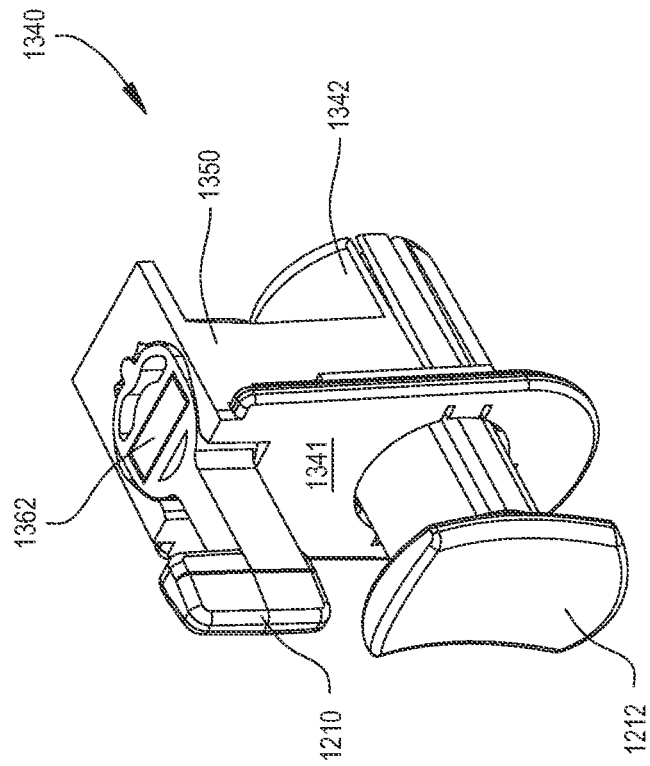
FIG. 75 is a perspective view of the switch assembly of the battery and control module of FIG. 64.
Figure 75A:
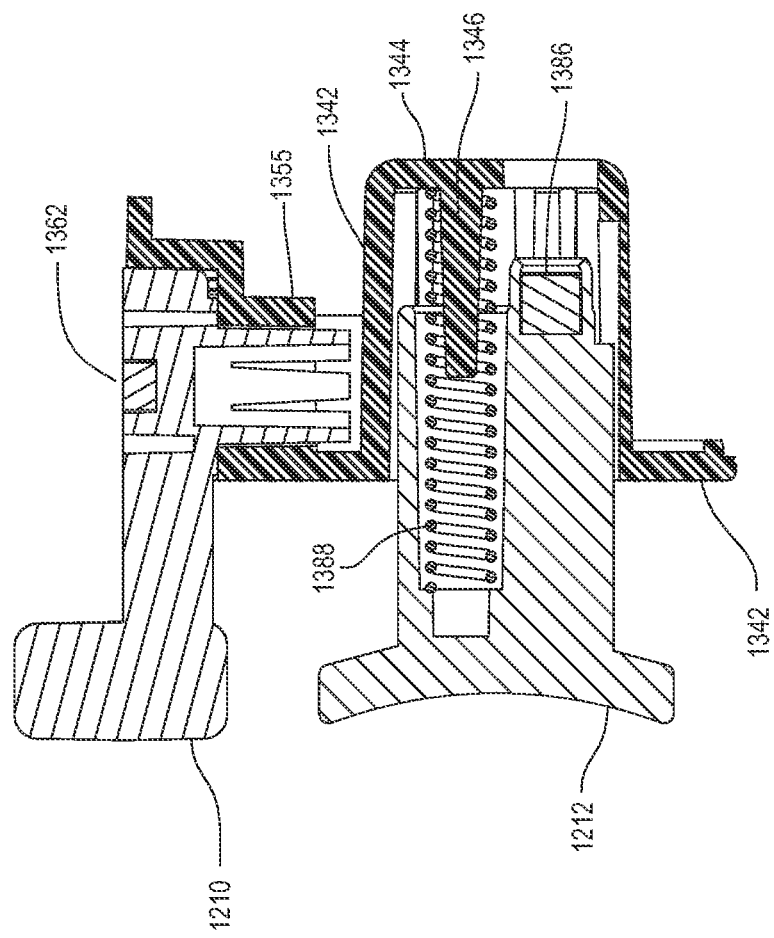
FIG. 75A is a cross sectional view of the switch assembly of FIG. 75.

From FIGS. 75, 75A and 76 it is seen that switches 1210 and 1212 are disposed in a housing 1340. Housing 1340 is formed from a single piece of sterilizable plastic. The housing 1340 has a front plate 1341. Plate 1341 is dimensioned to seat over the open end of shell recess 1266. A tube 1342 extends proximally from plate 1341. A panel 1344 extends over the proximal end of tube 1342. A post 1346 extends inwardly from the distally directed surface of panel 1344 into the tube. Below post 1346 panel 1344 has a through hole 1348.

Switch housing 1340 has a head 1350. Head 1350 extends away from the proximally directed face of the plate 1341. The housing is formed so that head 1350 is located above tube 1342. Head 1350 is formed to have an opening 1352 that extends downwardly from the top face of post 1344. Opening 1352, in cross section in a plane perpendicular to the top to bottom axis through the opening is generally in the shape of a flattened circle. The opening 1352 is open to the distally directed face of the housing 1340. The housing 1340 is further formed so as to have three indentations 1354 that extend outwardly from the opening 1352.

Housing 1340 is further formed so a step 1355 extends into and circumferentially around opening 1352. There is a space between tube 1342 and the bottom end of step 1355. Housing 1340 is dimensioned to seat in distal shell recess 1266.

From FIG. 77 it is seen that switch 1210 includes a head 1358. Head 1358 is dimensioned to seat in opening 1352 in switch housing 1340. Head 1358 is dimensioned to have a center frame like structure (not identified) that defines a rectangular center opening 1360. An arcuately shaped ear 1362 extends outwardly from the opposed ends of the center structure. Ear 1362 has a lobe 1364 that, in cross section is generally circular in shape. A number of tabs project downwardly from head 1358. These tabs are dimensioned to seat in the circular opening in the housing defined by step 1354. The tabs have generally arcuate outer surfaces. Two of the tabs, tabs 1366 in FIG. 77 are static. In the arcuate space between each tab 1366 there is a tab 1368, one seen in FIG. 77. Tabs 1368 are more flexible than tabs 1366. Each tab 1368 has at the free end and outwardly directed foot 1370. Switch 1210 is mounted to the housing 1340 by snap fitting the head 1358 in opening 1352 so that tab feet 1370 snap into the space below step 1355.

A stem 1372 projects distally forward from head 1358. A tab 1374 projects upwardly from the end of stem 1372.

A magnet 1362 is mounted in opening 1362 internal to switch head 1358. The position of switch 1210 is set by rotating the switch so that lobe 1364 seats in one of the indentations 1354 in switch housing 1340. The complementary sensor, sensor 580, outputs the PWM_TRG signal with a pulse width, duty cycle, that varies with the orientation of the magnet 1362 to the sensor.

Switch 1212 as seen in FIG. 78 includes a generally cylindrical barrel 1378. A boss 1380 extends outwardly from the proximal end of the barrel 1378. Boss 1380 is formed with a closed end bore, not identified. Barrel 1378 is formed to have a bore 1382 that extends longitudinally through the barrel. Both boss 1380 and bore 1382 are centered on longitudinal axes that are parallel to and offset from the center longitudinal axis through the barrel 1378. The outer surface of barrel 1378 is formed with features, not identified, that extend outwardly and inwardly from the curved outer surface of the barrel. These features cooperate with complementary features of the switch assembly housing 140 to facilitate the seating of the barrel in the housing tube 1342. More particularly, the housing 1342 and switch barrel 1378 have complementary features that hold the barrel in the tube 1342 so that the barrel can move longitudinally in the tube while preventing the rotation of the barrel.

The distal end of switch barrel 1378 extends forward of housing front plate 1341. A finger tab 1384 extends over the distal end of the barrel.

As part of the process of assembling BCM 1200 a magnet 1386 is seated in the bore internal to switch boss 1380. A spring 1388, seen in FIG. 75A, is disposed in barrel bore 1382. Spring 1388 is disposed around pin 1346. The proximal end of the spring 1388 seats against the distally directed face of switch housing panel 1344. The distal end of the spring is disposed against the surface internal to the barrel that defines the distal end of bore 1382. Spring 1388 thus exerts a force that normally positions the switch 1212 so that the switch is normally spaced distally away from housing panel 1344. The force spring 1388 exerts of switch 121 can be overcome with finger force.

Switch 1212 is mounted to the rest of the BCM 1200 so that magnet 1386 is adjacent sensor 566. The ANA_TRG signal output by sensor 566 thus represents the extent to which trigger switch 1212 has been depressed inwardly.

Figure 79:
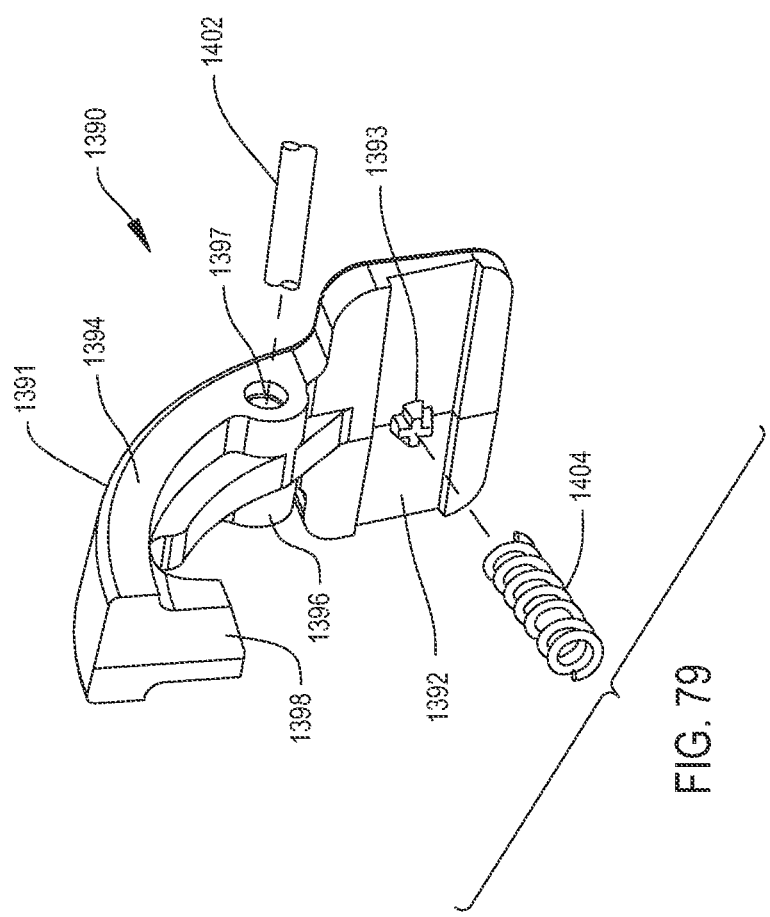
FIG. 79 is an exploded view of components forming the latch assembly of the battery and control module of FIG. 64.

A latch assembly 1390, the components of which are identified in FIGS. 65 and 79 releasably holds the tool unit 124 in nacelle bore 1257. In actuality there are two latch assemblies 1390, one on each side of the BCM 1200. The latch assemblies 1390 are simultaneously actuated in order to disconnect the tool unit 124 from the BCM 1200.

Each latch assembly 1390 includes a latch 1391. The latches 1391 are designed to seat in recess 1272 integral with the BCM housing. Each latch 1391 includes a generally rectangularly shaped tab 1392. Each tab 1392 is dimensioned to seat in the one of the relatively wide width end portions of recess 1272. Each tab 1392 is formed to have a cross-shaped boss 1393 that extends inwardly from the inner surface of the tab.

An arcuately shaped arm 1394 extends upwardly from latch tab 1392. The arm 1394 is dimensioned to fit in the curved portion of the shell recess 1272. The arm 1394 is formed to have a rib 1396 that extends across the arm. The rib 1396 is located a short distance above tab 1392. Rib 1396 is shaped to have a bore 1397 that extends proximally to distally through the rib Each arm 1394 is further formed to have, at the end spaced from tab 1392, a downwardly directed finger 1398. Latches 1391 are shaped so that each arm finger 1398 will seat in and extend through one-half the BCM housing opening 1274 into nacelle bore 1257.

When BCM 1200 is assembled, the latches 1391 are seated in distal shell recess 1272. On each side of the BCM housing, a pin 1402 extends through the housing bore 1276, bore 1397 internal to the latch 1391 and the adjacent shell notch 1278. Pins 1402 thus pivotally hold each latch 1391 to the BCM housing. A spring 1404 extends between the BCM housing and each latch 1391. Specifically, one end the spring 1404 seats in the ring 1279 that extends up from the surface of the housing that forms the base of the recess 1272. The opposed end of the spring seats over latch boss 1393. Each spring 1404 thus normally holds the associated latch 1391 in the locked state. The locked state is the state in which the latch finger protrudes into the nacelle bore 1257.

FIG. 80 depicts the main tube 1402 of a tool unit 124 that is used with BCM 1200. Main tube 950 is similar to previously described main tube 940. Both main tubes 940 and 13402 form part of the housing or body of the tool unit. Main tube 1402 is formed to have fin 1404 that extends outwardly from the surface of the cylindrical portion of the tube. In a plane perpendicular to a radial line extending out from the center of tube 1402, the fin would appear to have a rectangular shape. Fin 1404 is formed to have a ramp 1406. The ramp 1406 is located inwardly from the opposed sides of the fin 1404. Main tube 1402 is formed so that extending distally from the proximal end of the fin 1402, ramp extends outwardly away from the center axis of the tube. The fin 1404 is to have a pocket 1408. Pocket 1408 is located immediately forward of the distal end, the highest portion of ramp 1406. The pocket 1408 is generally rectangularly shaped. Pocket 1408 is dimensioned to receive the free ends of both latch fingers 1398.

A powered surgical tool assembly of this invention that includes BCM 1200 is prepared for use by inserting the tool unit in the nacelle bore 1257. As the tool unit main tube 1402 is slide in the bore 1257. Latch fingers 1398 ride up on ramp 1406. The manual insertion force is enough to overcome the force imposed by springs 1404. The latch arms thus move from the locked position to a release/load position. As the tool unit is moved proximally, the tool unit contacts 894 and 902 seat over the BCM contact pins 350. As the tool unit becomes fully seated in bore 1257, main tube pocket 1408 goes into registration with BCM housing opening 1274. Springs 1404 pivot the latches 1391 so that latch fingers 1398 seat in the pocket 1408. Thus, the latch assemblies 1390 releasably hold the tool unit 124 to BCM 124.

When the tool unit 124 is so positioned, sensors 594 are located below the motor rotor 966. The sensors 594 thus generate signals representative of the rotation position of the motor rotor 966.

The practitioner sets the operating mode of the tool unit power generating unit 950 by the setting of the position of switch 1210. Given the flexibility of ear 1363, as the switch is pivoted, the lobe 1364 will move out of and seat in each one of the indentations 1354 formed in switch housing 1340. The seating of the lobe 1364 in an indentation 1354 provides the practitioner with tactile feedback that the switch is in a particular setting.

If the power generating unit 950 is a motor, it is possible to set the motor to run in forward direction; reverse direction or an oscillate mode. The setting of the position of switch 1210 sets the orientation of magnet 1362. Sensor 580 outputs a PWM_TRG signal representative of the position of switch 1210.

The practitioner actuates the assembly by depressing trigger 1212. In response to the result change of level of the ANA_TRG signal, the tool unit controller 1290 sources and sinks the energization signals as appropriate to the contact pins 350 connected to the motor windings 954. Depending of the setting of switch 1210, the tool unit controller 1290, in energize tool unit power generating unit step 1042, will source/sink energize signals to either run the motor rotor in a forward direction, a reverse direction or an oscillate mode.

When it is time to disconnect the tool unit from BCM 1200, latch tabs 1392 are simultaneously depressed. This results in the pivoting of latch fingers 1398 out of the pocket 1408 integral with the tool unit main tube 1402. This transitioning of the latch assemblies 1390 from the locked position to the release/load position allows the tool unit to be removed from the BCM nacelle 1256.

It should thus be appreciated that a further feature of this invention is that a single tool unit can be used to form different types of tool assemblies. Thus if a particular practitioner prefers working with a pencil shaped tool, the tool unit can be coupled to a BCM such as BCM 128. If another practitioner prefers working with a pistol shaped tool, the same tool unit can be attached to BCM 1200.

IV. Alternative Embodiments

It should be understood that the foregoing is directed to specific embodiments of the invention and that variations from the described embodiments are possible.

For example while in many versions of the invention, the battery and control module will contain sensors that both monitor a switch attached to the module and sensors that monitor at least one operating state or condition of the handpiece, this is not required in all versions of the invention. Some BCMs of this invention may only include one or more sensors that generate signals as a function of the user operated switch. The tool controller internal to these BCMs controls the sourcing/sinking of energization signals as a function of these sensor signals. Still other BCMs of this invention may only include one or more sensors that generate signals as a function of the sensed operating condition or state of the attached tool unit. The tool controller internal to these BCMs controls the sourcing/sinking of energization signal as a function of these sensor signals.

Further, in versions of the invention wherein the sensor or sensors internal to the tool generate signals based on switch state, the switch may not always be attached to the BCM. In some versions of the invention the user actuated switch may be attached to the tool unit.

As mentioned above the user control may come from a foot switch unit or a voice control module. In these versions of the invention, to ensure that the assembly of this invention remains cordless, the battery and control module includes receiver 780 (FIG. 45). The receiver 780 is configured to receive either the signals, which are typically RF or optical signals, from the remote control head. This head may be either a foot switch assembly a voice control box. Receiver 780, in response to the received signals, outputs signals similar to the ANA_TRG and PWM_TRG signals the tool unit sensor circuit 590 would otherwise output. In versions of the invention in which receiver 780 is present, the trigger unit sensor circuit 590 may be omitted. The structure of receiver 780 is not part of the present invention.

It is further understood that in alternative powered surgical tool assemblies of this invention, the tool power generating unit may not always be a motor let alone a brushless DC motor. In these versions of the invention signals other than magnetic flux may function as the signals that are emitted by the tool unit that are representative of the operating state or condition of the tool power generating unit. Light may be one such signal. For example, if the tool unit is a laser, a set of light pipes in the tool unit and the BCM may serve as the conduits through which a fraction of the light is transmitted through the tool unit housing and the BCM housing to a light sensitive sensor internal to the BCM housing. either transparent windows or exposed faces of these light pipes would serve as the components of these housing through which the signals are transmitted. If the tool unit is an ultrasonic vibrator, the signal may be a mechanical vibration. In these embodiments of the invention, the tool unit housing and the BCM housing may include cores that are flexibly mounted to the other components of the housings. These cores serves as the paths through which the ultrasonic vibrations are applied to a sensor internal to the BCM.

Alternatively RF signals could be emitted by the tool power generating unit. These signals would vary as a function of operating state or condition of the tool. In these versions of the invention, the tool unit housing and BCM housing would both include at least components through which these signals would not be attenuated or distorted to the level at which operating of the BCM sensor/sensors would be adversely affected.

Likewise, even in versions of the invention in which the tool unit power generating unit is a motor, the signals emitted by the motor representative of motor state may not be magnetic fields. In some versions of the invention, an optical encoder may emit light that represents rotor position. Again, in these versions of the invention the tool unit housing and BCM housing would both include a component that is essentially transparent to the wavelength of light emitted or reflected by the motor.

In versions of the invention in which Hall sensors or other sensors sensitive to magnetic field strength such as magnetic-field sensitive resistors are used to provide an indication of rotor position, the sensor may not always be in the BCM housing. These sensors could be in the tool unit housing. It should be understood that these versions of the invention typically would require additional conductive links between the tool unit and the BCM in order to be able to forward the sensor signals to the drive controller 770.

In some versions of the invention in which the tool unit power generating unit is a motor, the tool unit controller 530 may not even use sensors to determine rotor position. Instead drive controller 770 could determine rotor position by measuring the back EMF signals developed across the one or more windings 594 through which the current is not be sourced. Alternatively, rotor position could be determined based on inductance sensing of rotor position. These methods of determining rotor position rely on measurements of the currents through or voltages across the motor windings 594. Applicant's U.S. Pat. No. 7,422,582/PCT Pub. No. WO 2006/039331, the contents of which are incorporated herein by reference, discloses how back EMF and inductance sensing can be used to determine rotor position.

The type of drive circuit internal to the battery and control module is a function of the power generating unit to which the module applies energization signals. For example if the attached tool unit requires a variable potential DC energization signal, the drive circuit may have one or more bipolar transistors that establish the potential of this signal. Alternatively, for some applications, the energization signal is sourced from or is regulated by a voltage-controlled oscillator.

In versions of this invention wherein tool unit power generating unit is a motor, the motor need not always be a brushless DC motor or even a DC motor. Further, the motor may have one winding, two windings or four or more windings. It should be understood that the number of windings the motor has directly establishes the number of contact pins the BCM has that are connected to the windings. Generally the BCM will have at least two contact pins. However, should there be four or more windings, the BCM may have four or more windings over which energization signals are selectively sourced/sunk to the tool unit power generating unit. Similarly, the motor may have one, two, three or more than four magnets.

It should though be appreciated that in versions of the invention wherein the tool unit power generating unit is a brushless DC motor that the BCM may not include any sensors. In these versions of the invention, the driver integral with the tool controller will at least include a driver with an appropriate number of FETs or other switch to selectively tie the contact pins that extend to the motor to either the BAT+ terminal (source current) or the BAT− terminal (sink current).

There is no requirement that in all versions of the invention the BCM rely on calibration data from a memory integral with the tool unit. Similarly, there is no requirement that in all versions of the invention the BCM write tool use data into a memory integral with the tool unit.

In some versions of this invention, the tool unit may include both the power generating unit and the energy applicator. In these versions of the invention there would be no need to provide the tool unit with a coupling assembly to releasably hold the energy applicator to the rest of the tool unit.

Further, the latch assembly is understood to be exemplary and not limiting. In alternative versions of the invention, the moving release components of the latch assembly may be part of the tool unit instead of part of the battery and control module. Still in other versions of the invention, the latch assembly may not have any manual actuated components. For example, the latch assembly could consist of complementary threading on the housings of the tool unit and battery and control module. Alternatively, these latch components may be components that form a releasable friction or compression fit between the tool unit and the battery and control module. Alternatively, spring loaded components attached to the tool unit or battery and control module are moved to a release state by a rotational movement of one or both the housings. In some versions of the invention, the electrical contacts that provide the conductive paths between the tool unit and battery and control module function as the latching components that hold the two units together.

The circuits of this invention may vary from what has been described. For example in versions of the invention in which there is only a single trigger switch, both described sensor 566 and 580 may be provided. In these versions of the invention the second sensor, typically but not always sensor 580 would provide a redundant sensor indicating the extent to which the switch was actuated. Further, there is no limit to the number of switch sensors incorporated into a BCM of this invention. For safety purposes it may be desirable to always provide two sensors to monitor the actuation of the on/off switch. One sensor each would be provided to monitor the states of the remaining switches.

Likewise it should be understood that the sensors that remotely monitor sensor actuation need not always be Halls sensors. For example, assuming the sensor includes a magnetized component, the sensor could be a magnetoresistive transducer.

Further in pencil shaped assemblies of this invention, it is desirable that the rechargeable cell 38 and tool unit partially overlap, this not need always be the case. In some versions of the invention, the tool unit and BCM may be arranged so that tool unit and cell are in a tandem arrangement.

Similarly, in alternative embodiments of the invention, alternative contacts may provide electrical connections between the tool unit and the battery and control unit. For example, the BCM contacts could simply be plates fixedly mounted to the BCM housing. In these versions of the invention, the tool unit may have spring biased or otherwise moveably contacts positioned to abut the BCM contacts.

Alternatively, one or both of the tool unit and BCM may have contacts that are flexible. For example, either the tool unit or BCM with flexible spring resilient contacts. The other of the BCM or tool unit would have static blade like contact. These static contacts press against the resilient contact to ensure good physical abutment between each pair of complementary contacts.

Further while the invention is described as being a powered tool assembly for use to perform medical and surgical procedures, including diagnostic procedures, its application is not so limited. Alternative embodiments of this invention may include tool units designed for purposes other than performing medical and surgical procedures.

Further in versions of the invention in which the BCM includes one or more sensor for monitoring switch state or the tool unit, the sensors may not be in the void space in which the cells and tool unit controller are located. Instead these sensors may be in their own cavities within the housing.

Likewise the dynamic seal of this invention that holds the contact pins 350 to the BCM housing that allows some pin movement while providing a barrier around the pins may have uses beyond that disclosed in this application.

Accordingly, it is an object of the appended claims to cover all such variations and modifications that come within the true spirit and scope of this invention.

What is claimed is:
1. A surgical tool system, said system comprising:
a tool unit, said tool unit including:
   a tool housing, said tool housing constructed so as to isolate components in said tool housing from effects of a sterilization process;
   a power generating unit disposed in said tool housing, wherein said power generating unit is configured to emit a signal representative of an operating state of said power generating unit and said tool housing is formed from material through which the signal emitted by said power generating unit can pass therethrough; and
   at least one tool contact mounted to said tool housing that is connected to said power generating unit over which energization currents are applied to said power generating unit to cause actuation of said power generating unit;
an energy applicator configured to perform a procedure on living tissue that is attached to said tool housing and connected to said power generating unit for actuation by said power generating unit; and
a battery and control module, said battery and control module including:
   a module housing separate from said tool housing, said module housing having a module void space, said module housing constructed so as to isolate components in the module void space from effects of the sterilization process and being shaped to be held by a hand;
   a latch feature integral with said module housing that cooperates with said tool housing to removably hold said tool housing to said module housing;
   at least one rechargeable cell disposed in the module void space;
   at least one module contact mounted to said module housing, said at least one module contact positioned to connect to said at least one tool contact when said tool housing is connected to the surgical tool unit power generating unit;
   a user actuated switch mounted to said module housing;
   at least one first sensor disposed in the module void space at a location wherein:
      said at least one first sensor is positioned in the module void space so that said at least one first sensor can receive the signal emitted by said power generating unit of said tool unit when said tool housing is held to said module housing;
      said at least one first sensor is configured to output a first sensor signal based on the monitored signal; and
      said module housing, in the vicinity of said first sensor, is formed from material through which the signals from said power generating unit can pass therethrough without being distorted to a level that results in operation of said at least one first sensor being adversely affected;
   at least one second sensor disposed in the module void space, said at least one second sensor configured to monitor a state of said switch and to, based on a state of said switch, output a second sensor signal; and
   a controller disposed in the module void space wherein said controller receives the first sensor signal and the second sensor signal and selectively connects said at least one rechargeable cell to said at least one module contact so as to regulate outputting of energization currents from said at least one rechargeable cell through said at least one module contact to said power generating unit, said controller being configured to, based on the first sensor signal and the second sensor signal, regulate the outputting of the energization currents.

2. The surgical tool system of claim 1, wherein said module housing is shaped to define a bore for receiving said tool housing.

3. The surgical tool system of claim 1, wherein:
said power generating unit emits a magnetic field through and outside of said tool housing as a function of an operating state of said power generating unit;
said at least one first sensor is configured to monitor the magnetic field emitted by said power generating unit and, based on the monitored magnetic field, output the first sensor signal; and
at least adjacent said at least one first sensor, said module housing is formed from material that allows magnetic fields emitted by said power generating unit to pass therethrough without adversely affecting the ability of said at least one first sensor to, based on the magnetic field, output the first sensor signal.

4. The surgical tool system of claim 1, wherein:
said switch is moveably mounted to said module housing and a magnet is attached to said switch to move with said switch;
said at least one second sensor is configured to monitor a magnetic field emitted by said switch magnet and to, based on the monitored magnetic field, output the second sensor signal; and
at least adjacent said at least one second sensor, said module housing is formed from material that allows magnetic fields emitted by said switch magnet to pass therethrough without adversely affecting the ability of said at least one second sensor to, based on the magnetic field, output the second sensor signal.

5. The surgical tool system of claim 1, wherein:
said tool unit includes at least one additional said tool contact for a total of two or more of said tool contacts that are connected to said power generating unit of said tool unit;
said at least one module contact includes a plurality of said module contacts that are mounted to said module housing, each of said module contacts being adapted to connect to a complementary one of said tool contacts; and
said controller includes a driver capable of connecting each of said plurality of said module contacts to either said at least one rechargeable cell or a ground.

6. The surgical tool system of claim 1, wherein said latch feature includes a component that is moveably mounted to said module housing for removably holding said tool housing to said module housing.

7. The surgical tool system of claim 1, wherein said at least one rechargeable cell includes a plurality of rechargeable cells that are disposed in said module housing and said plurality of rechargeable cells source the energization currents that are outputted to said power generating unit of said tool unit.

8. The surgical tool system of claim 1, wherein said at least one rechargeable cell is mounted in the module void space so that, when said tool housing is attached to said module housing, at least a portion of said at least one rechargeable cell is disposed distal of a proximal end of said tool housing.

9. The surgical tool system of claim 1, wherein:
said battery and control module includes at least one additional said first sensor for a total of two or more of said first sensors that are disposed in the module void space and each of said first sensors outputs a first sensor signal; and
said controller is further configured to, based on the plural first sensor signals received from said two or more of said first sensors, regulate the outputting of the energization currents from said at least one rechargeable cell to said power generating unit.

10. The surgical tool system of claim 1, wherein:
said tool housing is formed with a cannula; and
said module housing is further formed with a bore-defining component that is positioned so that, when said tool housing is held to said module housing, the bore defined by said housing component extends to the cannula internal to said tool housing.

11. The surgical tool system of claim 1, further including a coupling assembly attached to said tool housing for releasably holding said energy applicator to said tool housing and releasably connecting said energy applicator to said power generating unit.

12. A surgical tool system, said system comprising:
a tool unit, said tool unit including:
a tool housing, said tool housing having a proximal end and being constructed so as to isolate components therein from effects of a sterilization process;
a power generating unit disposed in said tool housing, wherein; said power generating unit is configured to emit a signal representative of an operating state of said power generating unit and said tool housing is formed from material through which the signal emitted by said power generating unit can pass therethrough; and
at least one tool contact mounted to said tool housing that is connected to said power generating unit over which energization currents are applied to said power generating unit to cause actuation of said power generating unit;
an energy applicator configured to perform a procedure on living tissue that is attached to said tool housing and connected to said power generating unit for actuation by said power generating unit; and
a battery and control module, said battery and control module including:
a module housing separate from said tool housing, said module housing having a module void space, said module housing constructed to isolate the module void space from effects of the sterilization process and being shaped to be held by a hand;
a latch feature integral with said module housing that cooperates with said tool housing to removably hold said tool housing to said module housing;
at least one rechargeable cell disposed in the module void space, said at least one rechargeable cell being positioned within the module void space so that, when said tool housing is held to said module housing, said at least one rechargeable cell is at least partially distal to the proximal end of said tool housing;
at least one module contact mounted to said module housing, said at least one module contact positioned to connect to said at least one tool contact;
a user actuated switch mounted to said module housing;
at least one first sensor disposed in the module void space, said at least one first sensor configured to: monitor a signal emitted by said power generating unit of said tool unit and output a first sensor signal based on the monitored signal;
said module housing, in the vicinity of said first sensor, is formed from material through which the signals from said power generating unit can pass therethrough without being distorted to a level that results in operation of said at least one first sensor being adversely affected;
at least one second sensor disposed in the module void space, said at least one second sensor configured to monitor a state of said switch and to, based on the state of said switch, output a second sensor signal; and
a controller disposed in the module void space wherein said controller receives the first sensor signal and the second signal and that selectively connects said at least one rechargeable cell to said at least one module contact so as to regulate outputting of energization currents from said at least one rechargeable cell through said at least one module contact to said power generating unit, said controller being configured to, based on the first sensor signal and the second sensor signal, regulate the outputting of the energization signals from said at least one rechargeable cell to said power generating unit.

13. The surgical tool system of claim 12, wherein said module housing is shaped to define a bore for receiving said tool housing.

14. The surgical tool system of claim 12, wherein:
said module housing is shaped to define a bore for receiving said tool housing, and said module housing includes a structural member that defines a proximal end of the bore; and
said at least one module contact is mounted to the structural member that defines the proximal end of the bore.

15. The surgical tool system of claim 12, wherein:
said power generating unit emits a magnetic field through and outside of said tool housing as a function of an operating state of said power generating unit;
said at least one first sensor is configured to monitor the magnetic field emitted by said power generating unit and, based on the monitored magnetic field, output the first sensor signal; and
at least adjacent said at least one first sensor, said module housing is formed from material that allows magnetic fields emitted by said surgical tool unit to pass therethrough without adversely affecting the ability of said at least one first sensor to, based on the magnetic field, output the first sensor signal.

16. The surgical tool unit of claim 12, wherein:
said switch is moveably mounted to said module housing and a magnet is attached to said switch to move with said switch;
said at least one second sensor is configured to monitor a magnetic field emitted by said switch magnet and to, based on the monitored magnetic field, output the second sensor signal; and
at least adjacent said at least one second sensor, said module housing is formed from material that allows magnetic fields emitted by said switch magnet to pass therethrough without adversely affecting the ability of said at least one second sensor to, based on the magnetic field, output the second sensor signal.

17. The surgical tool system of claim 12, wherein said battery and control module includes at least one additional rechargeable cell for a total of two or more of said rechargeable cells that are disposed in said module housing and said two or more rechargeable cells source the energization currents that are outputted to said power generating unit.

18. The surgical tool system of claim 12, wherein:
said battery and control module includes at least one additional rechargeable cell for a total of two or more of said rechargeable cells that are disposed in the module void space and said plurality of rechargeable cells source the energization currents that are outputted to the tool power generating unit; and said two or more of rechargeable cells are disposed in the module void space so that when said tool housing is held to said module housing, at least one of said plurality of rechargeable cells is located at least partially distal to the proximal end of said tool housing and at least another one of said plurality of rechargeable cells is located proximal to the proximal end of said tool housing.

19. The surgical tool unit of claim 12, wherein:
said tool unit includes at least one additional said tool contact for a total of two or more of said tool contacts that are connected to said power generating unit of said tool unit;
said battery and control module includes at least one additional said module contact for a total of two or more of said module contacts that are mounted to said module housing, each of said two or more of module contacts being adapted to connect to a complementary one of said tool contacts; and
said controller includes a driver capable of individually connecting said plurality of module contacts to either said at least one rechargeable cell or a ground.

20. The surgical tool system of claim 12, wherein:
said battery and control module includes at least one additional said first sensor for a total of two or more of said first sensors that are disposed in the module void space and each of said first sensors outputs a first sensor signal; and
said controller is further configured to, based on the plural first sensor signals received from the two or more of said first sensors, regulate the outputting of the energization signals from said at least one rechargeable cell to the tool unit power generating unit.

21. The surgical tool system of claim 12, wherein at least a portion of said module housing is formed from material through which the signal emitted by said power generating unit can pass wirelessly therethrough without being distorted to level that results in operation of said at least one first sensor being adversely affected.

22. The surgical tool system of claim 12, wherein said latch feature includes a component that is moveably mounted to said module housing for removably holding said tool housing to said module housing.

23. The surgical tool system of claim 12, wherein said module housing is shaped and said at least one rechargeable cell is disposed in the module void space so that, when said module housing and said tool housing are held so that said energy applicator is normally directed to tissue, said at least one rechargeable cell is disposed above said tool unit.

24. The surgical tool system of claim 12, further including a coupling assembly attached to said tool housing for releasably holding said energy applicator to said tool housing and releasably connecting said energy applicator to said power generating unit.

* * * * *